US012624106B2

(12) United States Patent
Yu et al.

(10) Patent No.: US 12,624,106 B2
(45) Date of Patent: May 12, 2026

(54) COMBINATION OF LILRB1/2 PATHWAY INHIBITORS AND PD-1 PATHWAY INHIBITORS

(71) Applicant: AMGEN INC., Thousand Oaks, CA (US)

(72) Inventors: Xin Yu, Foster City, CA (US); Wenjun Ouyang, Foster City, CA (US); Chi-Ming Kevin Li, Thousand Oaks, CA (US); Jackson Graeme Egen, San Mateo, CA (US); Oh Kyu Yoon, Pacifica, CA (US); Ian Halsey Driver, San Francisco, CA (US); Shunsuke Takenaka, Burnaby (CA); Christy Ann Thomson, Port Moody (CA); Hongyu Wang, Coquitlam (CA)

(73) Assignee: AMGEN INC., Thousand Oaks, CA (US)

( * ) Notice: Subject to any disclaimer, the term of this patent is extended or adjusted under 35 U.S.C. 154(b) by 1120 days.

(21) Appl. No.: 17/262,339

(22) PCT Filed: Jul. 17, 2019

(86) PCT No.: PCT/US2019/042234
§ 371 (c)(1),
(2) Date: Jan. 22, 2021

(87) PCT Pub. No.: WO2020/023268
PCT Pub. Date: Jan. 30, 2020

(65) Prior Publication Data
US 2021/0301020 A1      Sep. 30, 2021

Related U.S. Application Data

(60) Provisional application No. 62/872,431, filed on Jul. 10, 2019, provisional application No. 62/702,493, filed on Jul. 24, 2018.

(51) Int. Cl.
C07K 16/28      (2006.01)
A61K 39/00      (2006.01)
A61P 35/00      (2006.01)

(52) U.S. Cl.
CPC .......... *C07K 16/2818* (2013.01); *A61P 35/00* (2018.01); *C07K 16/2803* (2013.01); *C07K 16/2827* (2013.01); *C07K 16/2833* (2013.01); *A61K 2039/507* (2013.01); *C07K 2317/34* (2013.01); *C07K 2317/565* (2013.01); *C07K 2317/73* (2013.01); *C07K 2317/76* (2013.01); *C07K 2317/92* (2013.01)

(58) Field of Classification Search
CPC . A61P 35/00; C07K 16/2827; C07K 16/2833; C07K 2317/565; A61K 2039/507
See application file for complete search history.

(56) References Cited

U.S. PATENT DOCUMENTS

| | | | |
|---|---|---|---|
| 5,595,756 A * | 1/1997 | Bally | A61K 9/1272 |
| | | | 264/4.1 |
| 6,140,076 A | 10/2000 | Adema | |
| 7,943,329 B2 | 5/2011 | Atwal | |
| 11,518,808 B2 * | 12/2022 | Ali | C12N 15/85 |
| 11,530,274 B2 * | 12/2022 | Nolan-Stevaux | A61P 13/08 |
| 2012/0121606 A1 * | 5/2012 | Ruben | A61P 37/06 |
| | | | 424/139.1 |
| 2015/0174203 A1 | 6/2015 | Chen | |
| 2016/0200815 A1 | 7/2016 | Feldman | |
| 2017/0274003 A1 | 9/2017 | Shatz | |
| 2017/0360932 A1 | 12/2017 | Parry | |
| 2018/0118823 A1 | 5/2018 | Thompson | |

FOREIGN PATENT DOCUMENTS

| | | | |
|---|---|---|---|
| WO | 2014116846 A2 | 7/2014 | |
| WO | WO-2016065329 A1 * | 4/2016 | ......... C07K 16/2803 |
| WO | 2016127247 A1 | 8/2016 | |
| WO | 20160144728 W | 9/2016 | |
| WO | 2016179194 A1 | 11/2016 | |
| WO | 2018022881 A2 | 2/2018 | |
| WO | 2018027197 A1 | 2/2018 | |
| WO | 2018187518 | 10/2018 | |
| WO | 2019126514 | 6/2019 | |
| WO | WO-2019140196 A1 * | 7/2019 | ........... A61K 39/395 |

OTHER PUBLICATIONS

Heppner et al., Tumor heterogeneity: biological implications and therapeutic consequences, 1983, Cancer Metastasis Reviews 2: 5-23 (Year: 1983).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Jain RK, Barriers to Drug Delivery in Solid Tumors, 1994, Scientific American, pp. 58-645 (Year: 1994).*
Brown et al., J Immunol. May 1996; 156(9):3285-91 (Year: 1996).*
Gura T, Systems for Identifying New Drugs are Often Faulty, Science, 1997, 278(5340): 1041-1042 (Year: 1997).*
Greenspan et al. 1999 Defining epitopes: It's not as easy as it seems; Nature Biotechnology, 17:936-937 (Year: 1999).*
Sporn et al. Chemoprevention of Cancer, Carcinogenesis, vol. 21 (2000), 525-530 (Year: 2000).*

(Continued)

*Primary Examiner* — Vanessa L. Ford
*Assistant Examiner* — Danaya L Middleton
(74) *Attorney, Agent, or Firm* — Cynthia T. Chen

(57)      ABSTRACT

This invention relates to combination therapies comprising a Programmed Death 1 receptor (PD-1) pathway inhibitor, and a Leukocyte Immunoglobulin Like Receptor B (LILRB) signaling inhibitor, and the use of the combination therapies for the treatment of cancer. The invention also relates to the treatment of cancer patients who are refractory to monotherapy with a PD-1 pathway inhibitor.

27 Claims, 10 Drawing Sheets

Specification includes a Sequence Listing.

(56) References Cited

OTHER PUBLICATIONS

Auerbach et al, Angiogenesis assays: Problems and pitfalls, Cancer and Metastasis Reviews, 2000, 19: 167-172 (Year: 2000).*

Bork. Powers and Pitfalls in Sequence Analysis: The 70% Hurdle. Genome Research, 2000, 10:398-400 (Year: 2000).*

Skolnick et al., Trends Biotechnol. Jan. 2000;18(1):34-9 (Year: 2000).*

Vajdos et al., J Mol Biol. Jul. 5, 2002;320(2):415-28 at 416 (Year: 2002).*

Hait., Anticancer drug development: the grand challenges, Nature Reviews/Drug Discovery, 2010, 9, pp. 253-254 (Year: 2010).*

Gravanis et al., The changing world of cancer drug development: the regulatory bodies' perspective, Chin Clin Oncol, 2014, 3, pp. 1-5 (Year: 2014).*

Miosge, Proc Natl Acad Sci U S A. Sep. 15, 2015;112(37): E5189-98 (Year: 2015).*

Lin et al., Mol Med 21: 782-791, 2015 (Year: 2015).*

Boshoff, www.onclive.com/view/avelumab-falls-short-in-phase-iii-gastric-cancer-trial; published online Nov. 28, 2017 (Year: 2017).*

Rouas-Freiss et al., Oncoimmunology 2017, vol. 6, No. 9, e1342023 (Year: 2017).*

Ayers et al., Clin Invest. 2017;127(8):2930-2940 (Year: 2017).*

Beans, Targeting metastasis to halt cancer's spread, PNAS 2018; 115(50): 12539-12543 (Year: 2018).*

Kulmanov et al., Bioinformatics, 34(4), 2018, 660-668 (Year: 2018).*

Siu et al, Clin Cancer Res 2022; 28(1): 57-70 (Year: 2022).*

Mandel et al, Journal for Immuno Therapy of Cancer 2022;10:e004859 (Year: 2022).*

Sun et al, Signal Transduction and Targeted Therapy (2023) 8:320 (Year: 2023).*

Cella et al. J Exp Med. May 19, 1997;185(10):1743-51.

International Preliminary Report and Written Opinion for corresponding applicaton No. PCT/US2019/042234, issued Jan. 26, 2021.

International Search Report for corresponding applicaton No. PCT/US2019/042234, mailed Dec. 26, 2019.

Samaridis and Colonna, Eur. J. Immunol. 27 (3), 660-665, 1997.

Chen et al., "Blocking immunoinhibitory receptor LILRB2 reprograms tumor-associated myeloid cells and promotes antitumor immunity", Journal of Clinical Investigation, vol. 128, No. 12, pp. 5647, Oct. 22, 2018.

* cited by examiner

FIG. 1A
FIG. 1B
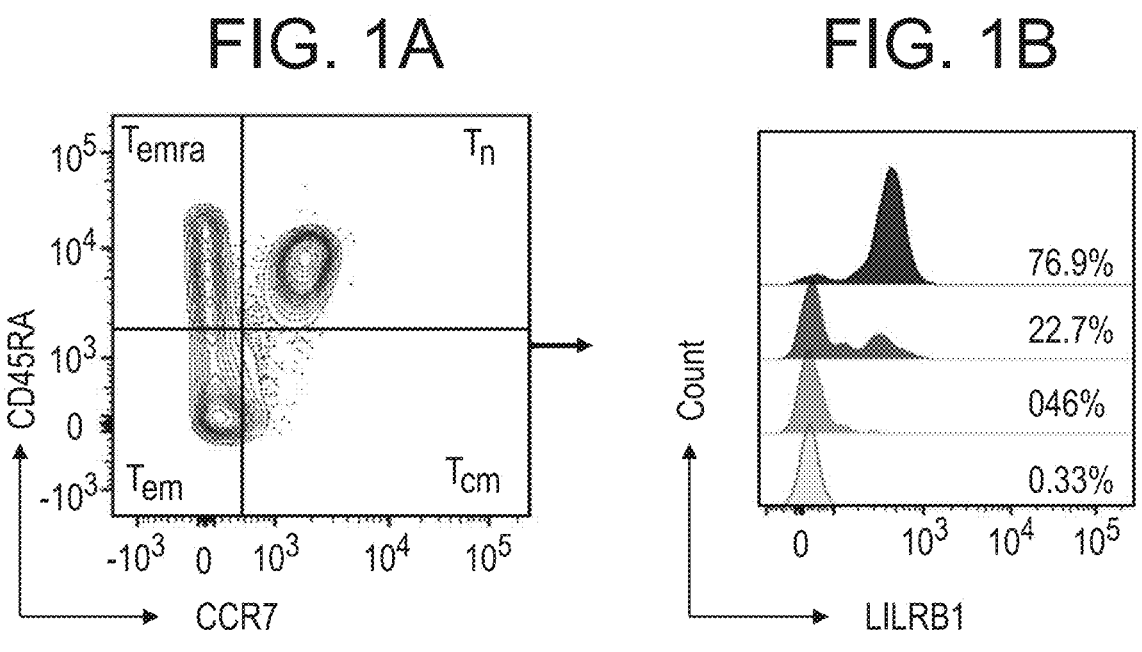
FIG. 1C
FIG. 1D
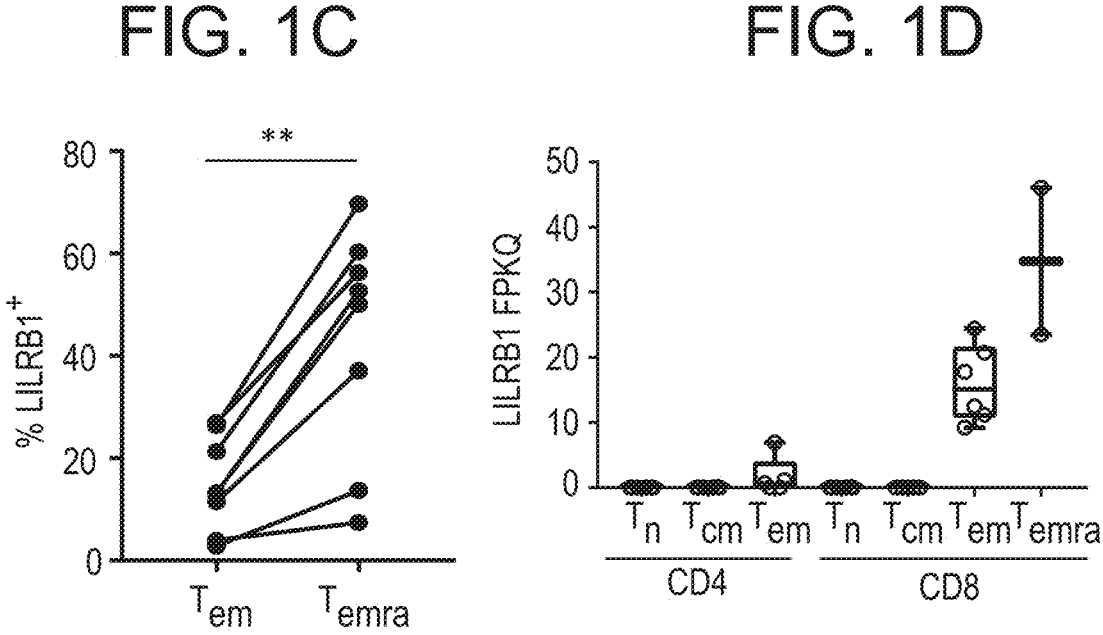

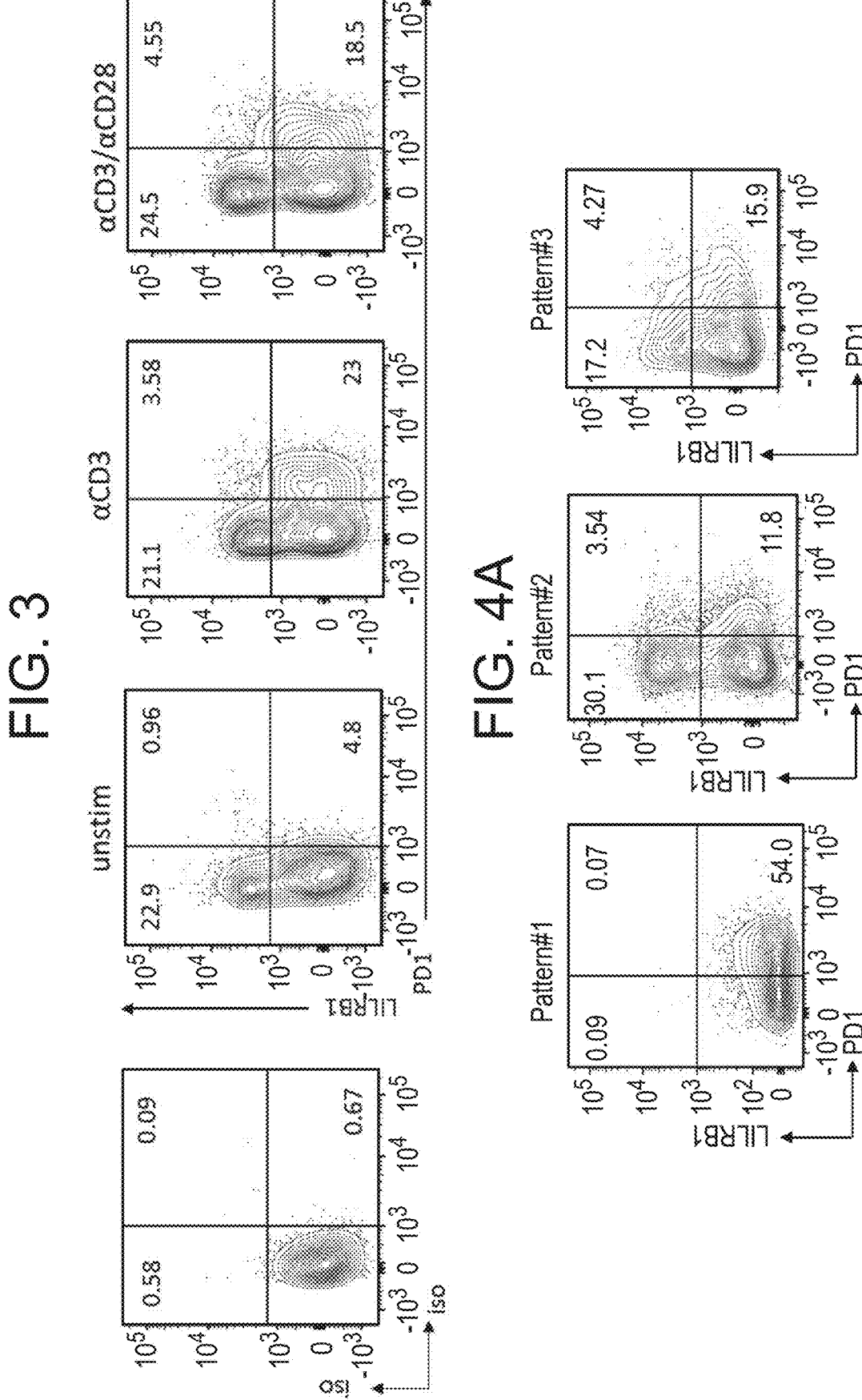

FIG. 5A

| T cell immune receptors | | Checkpoint inhibitors | | | | Co-inhibitory receptors on CD8 | | | Co-stimulatory receptors | | | | | |
|---|---|---|---|---|---|---|---|---|---|---|---|---|---|---|
| | | CTLA4 | TIM3 | TIGIT | LAG3 | CD160 | NKG2A | KIRs | CD28 | ICOS | 4-1BB | CD27 | OX40 | GITR |
| CD8 | LILRB1+ | 6 | 10 | 35 | 17 | 15 | 9 | 4-8 | 11 | 14 | 6 | 21 | 4 | 4 |
| | PD1+ | 40 | 56 | 75 | 59 | 20 | 25 | 2-21 | 51 | 50 | 38 | 74 | 9 | 12 |

FIG. 5B

| T cell immune receptors | | Checkpoint inhibitors | | | | Co-inhibitory receptors on CD8 | | | Co-stimulatory receptors | | | | | |
|---|---|---|---|---|---|---|---|---|---|---|---|---|---|---|
| | | CTLA4 | TIM3 | TIGIT | LAG3 | CD160 | NKG2A | KIRs | CD28 | ICOS | 4-1BB | CD27 | OX40 | GITR |
| CD8 | LILRB1+ | 9 | 9 | 4 | 9 | 0 | 0 | 4 | 0 | 4 | 0 | 0 | 0 | 0 |
| | PD1+ | 20 | 17 | 10 | 37 | 0 | 0 | 0-6 | 0 | 3 | 0 | 30 | 0 | 0 |

Pair#1

Pair#2

FIG. 8A
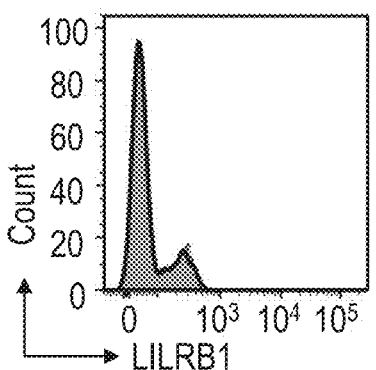
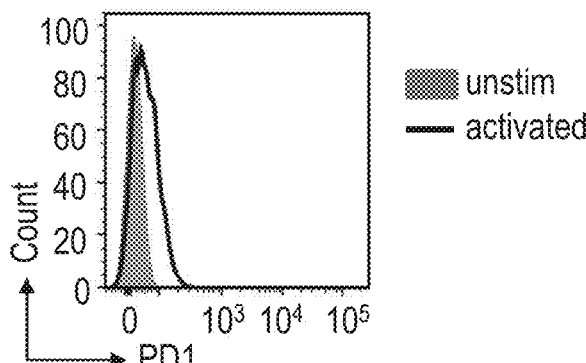
FIG. 8B
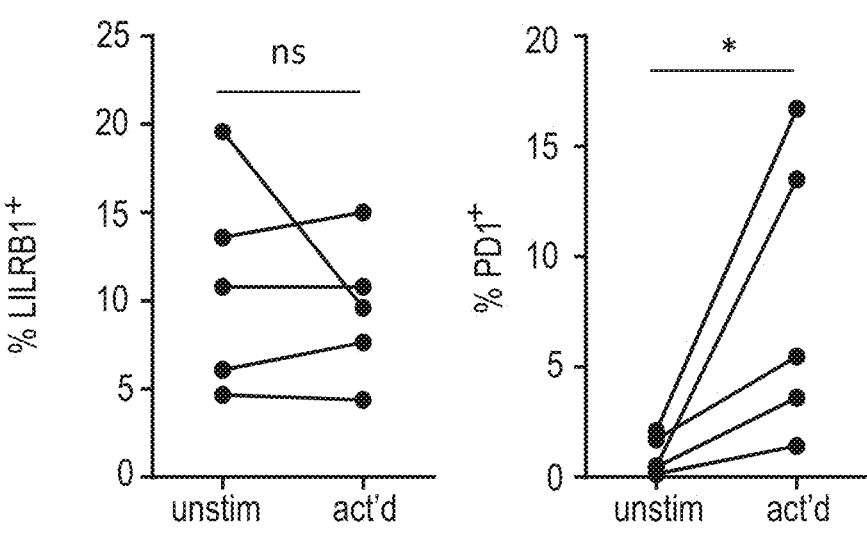

FIG. 8C
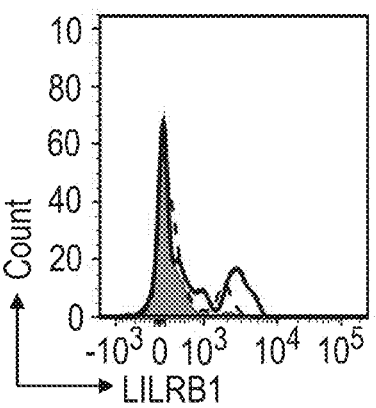
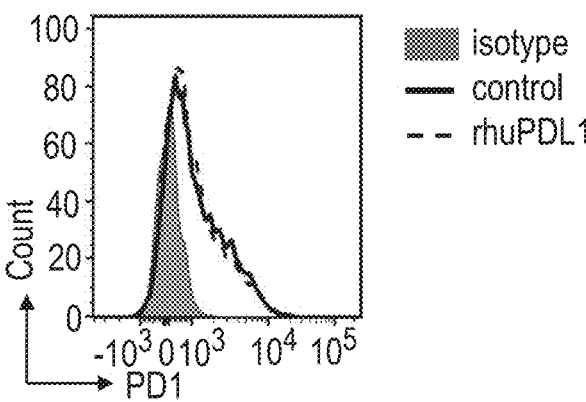
FIG. 8D
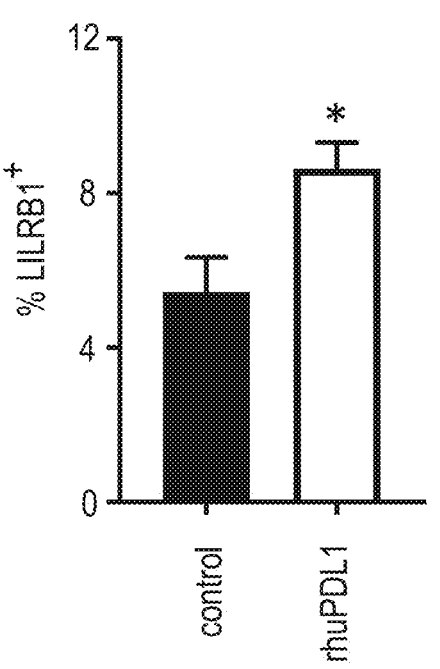
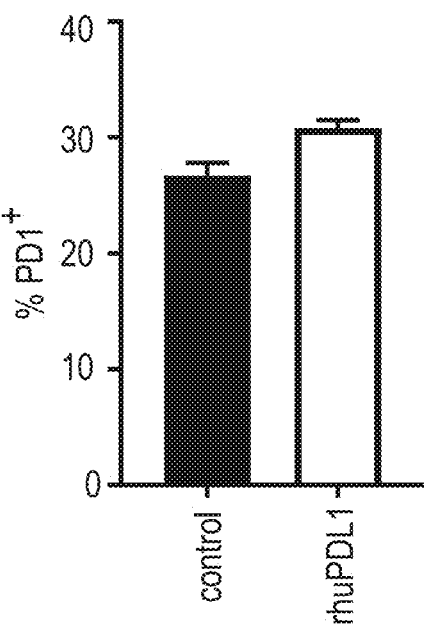

COMBINATION OF LILRB1/2 PATHWAY INHIBITORS AND PD-1 PATHWAY INHIBITORS

RELATED APPLICATIONS

This application is the U.S. National Phase of International Application No. PCT/US2019/042234, filed Jul. 17, 2019 and published in English, which claims the benefit under 35 U.S.C. § 119(e) to U.S. Provisional Application No. 62/702,493, filed Jul. 24, 2018, and U.S. Provisional Application No. 62/872,431, filed Jul. 10, 2019. The complete contents of the aforementioned applications are incorporated herein by reference for all purposes.

SEQUENCE LISTING

The instant application contains a Sequence Listing which has been submitted electronically in ASCII format and is hereby incorporated by reference in its entirety. Said ASCII copy, created on Jan. 21, 2021, is named A-2271-US-PCT_SL.txt and is 122,949 bytes in size.

FIELD OF THE INVENTION

The present invention relates to combination therapies useful for the treatment of cancer.

BACKGROUND OF THE INVENTION

In the two-signal model T-cell activation is regulated by both positive and negative secondary co-stimulatory signals that function to maximize the host's protective immune responses, while maintaining immune tolerance and preventing autoimmunity. While the two-signal model was originally developed to describe the regulation of naive lymphocyte activation, a host's immune response is a multi-step and dynamic process and a similar paradigm of regulation by co-stimulatory signals applies to antigen-experienced T-cells. The positive and negative co-stimulatory signals regulating both naive and antigen-experienced T cell activation are of therapeutic interest as manipulation of these signals provides a means to either enhance or terminate cell-based immune response. For example, the inhibitory receptor programmed cell death 1 (PD-1) is upregulated on chronically stimulated T cells and its sustained expression correlates with T cell dysfunction or anergy. As a result, therapeutics aimed at enhancing T cell activation by targeting of PD-1 or other molecules which signal through interactions with PD-1, such as programmed death ligand 1 (PD-L1) and programmed death ligand 2 (PD-L2), have generated great interest.

PD-L1 is overexpressed in many cancers and is often associated with poor prognosis (Okazaki T et al., Intern. Immun. 2007 19(7):813; Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes, indicating that up-regulation of PD-1 on tumor-reactive T cells can contribute to impaired antitumor immune responses (Blood 2009 114(8):1537). This may be due to exploitation of PD-L1 signaling, mediated by PD-L1 expressing tumor cells interacting with PD-1 expressing T cells, resulting in attenuation of T cell activation and evasion of immune surveillance (Sharpe et al., Nat Rev 2002, Keir M E et al., 2008 Annu. Rev. Immunol.

26:677). Therefore, inhibition of the PD-L1/PD-1 interaction may enhance CD8+ T cell-mediated killing of tumors.

Therapeutic approach of blocking the PD-1/PD-L1 immune checkpoint proteins as anticancer agents has been successful in treating melanoma and NSCLC patients. However, overall more than 70% of cancer patients do not respond to PD-1 blockade. This may be because additional inhibitory mechanisms function to inhibit the activity of CD8+ T cells within the tumor microenvironment. For instance, CD8+ T cells can express other inhibitory receptors in addition to PD-1. Therefore, combination of therapeutic drugs that target different immune regulatory pathways may increase efficacy in cancer treatment. For example, clinical trial data of anti-PD-1 combined with anti-CTLA4, another checkpoint receptor on T cells, has shown improved efficacy in melanoma patients.

There is a need for improved therapies for the treatment of cancer, in particular in patients who are poor responders to anti-PD-1/anti-PD-L1 treatment.

SUMMARY OF THE INVENTION

Based on the disclosure provided herein, those skilled in the art will recognize, or be able to ascertain using no more than routine experimentation, many equivalents to the specific embodiments of the invention described herein. Such equivalents are intended to be encompassed by the following embodiments (E).

E1. A method for increasing IFN-$\gamma$ expression level in a subject that has cancer, comprising administering to the subject a therapeutically effective amount of (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E2. The method of E1, wherein said first antibody, or antigen-binding fragment thereof, binds PD-1.

E3. The method of E1 or E2, wherein said first antibody, or antigen-binding fragment thereof, binds human PD-1.

E4. The method of any one of E1-E3, wherein said first antibody is nivolumab, pembrolizumab, pidilizumab, or an antigen binding fragment thereof.

E5. The method of E1, wherein said first antibody, or antigen-binding fragment thereof, binds PD-L1, PD-L2, or both.

E6. The method of E1 or E5, wherein said first antibody, or antigen-binding fragment thereof, binds human PD-L1, PD-L2, or both.

E7. The method of any one of E1 and E5-E6, wherein said first antibody is avelumab, atezolizumab, durvalumab or an antigen binding fragment thereof.

E8. The method of any one of E1-E7, wherein said second antibody, or antigen-binding fragment thereof, binds LILRB1, LILRB2, or both.

E9. The method of any one of E1-E8, wherein said second antibody, or antigen-binding fragment thereof, binds human LILRB1, human LILRB2, or both.

E10. The method of any one of E1-E9, wherein said second antibody, or antigen-binding fragment thereof, binds both human LILRB1 and human LILRB2.

E11. The method of any one of E1-E7, wherein said second antibody, or antigen-binding fragment thereof, binds HLA-G.

E12. The method of any one of E1-E7 and E11, wherein said second antibody, or antigen-binding fragment thereof, binds human HLA-G.

E13. The method of any one of E1-E12, wherein said first antibody, or antigen-binding fragment thereof, and said second antibody, or antigen-binding fragment thereof, are administered concurrently.

E14. The method of any one of E1-E12, wherein said first antibody, or antigen-binding fragment thereof, and said second antibody, or antigen-binding fragment thereof, are administered sequentially.

E15. The method of E14, wherein one or more doses of said first antibody, or antigen-binding fragment thereof, are administered prior to administering said second antibody, or antigen-binding fragment thereof.

E16. The method of E14, wherein one or more doses of said second antibody, or antigen-binding fragment thereof, are administered prior to administering said first antibody, or antigen-binding fragment thereof.

E17. A method for increasing IFN-γ expression level in a subject that has cancer, comprising administering to the subject a therapeutically effective amount of (i) an antibody, or antigen-binding fragment thereof, that binds PD-1, PD-L1, or PD-L2; and (ii) a short interfering RNA (siRNA) that reduces the expression level of HLA-G, as compared to a control.

E18. The method of E17, wherein said siRNA comprises the nucleotide sequence of SEQ ID NO: 31.

E19. The method of any one of E1-E18, wherein said subject is a human.

E20. The method of any one of E1-E19, wherein said cancer is a solid tumor.

E21. The method of any one of E1-E20, wherein the cancer is brain cancer, bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, colorectal cancer, or gastric cancer.

E22. The method of any one of E1-E21, wherein said subject is refractory to treatment with an anti-PD-1 antibody or antigen-binding fragment thereof, or with an anti-PD-L1 antibody or antigen-binding fragment thereof.

E23. The method of any one of E1-E22, wherein said subject is refractory to treatment with an anti-PD-1 antibody or antigen-binding fragment thereof.

E24. The method of any one of E1-E23, wherein said subject is refractory to treatment with an anti-LILRB1 antibody or antigen-binding fragment thereof, an anti-LILRB2 antibody or antigen-binding fragment thereof, or an anti-HLA-G antibody or antigen-binding fragment thereof.

E25. The method of any one of E1-E24, wherein said subject is refractory to treatment with an anti-LILRB1 antibody or antigen-binding fragment thereof.

E26. A method for increasing CD8+ T-cell mediated cytotoxicity in a subject that has cancer, comprising administering to the subject a therapeutically effective amount of (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E27 The method of E26, wherein said first antibody, or antigen-binding fragment thereof, binds PD-1.

E28. The method of E26 or E27, wherein said first antibody, or antigen-binding fragment thereof, binds human PD-1.

E29. The method of any one of E26-E28, wherein said first antibody is nivolumab, pembrolizumab, pidilizumab or an antigen binding fragment thereof.

E30. The method of E26, wherein said first antibody, or antigen-binding fragment thereof, binds PD-L1, PD-L2, or both.

E30. The method of E26 or E30, wherein said first antibody, or antigen-binding fragment thereof, binds human PD-L1, PD-L2, or both.

E32. The method of any one of E26 and E30-E31, wherein said first antibody is avelumab, atezolizumab, durvalumab or an antigen binding fragment thereof.

E33. The method of any one of E26-E32, wherein said second antibody, or antigen-binding fragment thereof, binds LILRB1, LILRB2, or both.

E34. The method of any one of E26-E33, wherein said second antibody, or antigen-binding fragment thereof, binds human LILRB1, human LILRB2, or both.

E35. The method of any one of E26-E34, wherein said second antibody, or antigen-binding fragment thereof, binds both human LILRB1 and human LILRB2.

E36. The method of any one of E26-E32, wherein said second antibody, or antigen-binding fragment thereof, binds HLA-G.

E37. The method of any one of E26-E32 and E36, wherein said second antibody, or antigen-binding fragment thereof, binds human HLA-G.

E38. The method of any one of E26-E37, wherein said first antibody, or antigen-binding fragment thereof, and said second antibody, or antigen-binding fragment thereof, are administered concurrently.

E39. The method of any one of E26-E37, wherein said first antibody, or antigen-binding fragment thereof, and said second antibody, or antigen-binding fragment thereof, are administered sequentially.

E40. The method of E39, wherein one or more doses of said first antibody, or antigen-binding fragment thereof, are administered prior to administering said second antibody, or antigen-binding fragment thereof.

E41. The method of E39, wherein one or more doses of said second antibody, or antigen-binding fragment thereof, are administered prior to administering said first antibody, or antigen-binding fragment thereof.

E42. A method for increasing CD8+ T-cell mediated cytotoxicity in a subject that has cancer, comprising administering to the subject a therapeutically effective amount of (i) an antibody, or antigen-binding fragment thereof, that binds PD-1, PD-L1, or PD-L2; and (ii) a short interfering RNA (siRNA) that reduces the expression level of HLA-G, as compared to a control.

E43. The method of E42, wherein said siRNA comprises the nucleotide sequence of SEQ ID NO: 31.

E44. The method of any one of E26-E43, wherein said subject is a human.

E45. The method of any one of E26-E44, wherein said cancer is a solid tumor.

E46. The method of any one of E26-E45, wherein the cancer is brain cancer, bladder cancer, breast cancer, clear cell kidney cancer, head/neck squamous cell carcinoma, lung squamous cell carcinoma, malignant melanoma, non-smallcell lung cancer (NSCLC), ovarian cancer, pancreatic cancer, prostate cancer, renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, colorectal cancer, or gastric cancer.

E47. The method of any one of E26-E46, wherein said CD8+ T-cell mediated cytotoxicity is assessed by IFN-γ expression level in said subject.

E48. The method of any one of E26-E47, wherein said subject is refractory to treatment with an anti-PD-1 antibody or antigen-binding fragment thereof, or with an anti-PD-L1 antibody or antigen-binding fragment thereof.

E49. The method of any one of E26-E48, wherein said subject is refractory to treatment with an anti-PD-1 antibody or antigen-binding fragment thereof.

E50. The method of any one of E26-E49, wherein said subject is refractory to treatment with an anti-LILRB1 antibody or antigen-binding fragment thereof, an anti-LILRB2 antibody or antigen-binding fragment thereof, or an anti-HLA-G antibody or antigen-binding fragment thereof.

E51. The method of any one of E26-E50, wherein said subject is refractory to treatment with an anti-LILRB1 antibody or antigen-binding fragment thereof.

E52. A method for treating a subject that has a tumor, wherein said subject is refractory to treatment with an anti-PD-1 antibody or antigen-binding fragment thereof, or with an anti-PD-L1 antibody or antigen-binding fragment thereof, comprising: administering to the subject a therapeutically effective amount of (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E53. The method of E52, wherein said subject is also refractory to treatment with an anti-LILRB1 antibody or antigen-binding fragment thereof, an anti-LILRB2 antibody or antigen-binding fragment thereof, or an anti-HLA-G antibody or antigen-binding fragment thereof.

E54. The method of E52 or E53, wherein said first antibody, or antigen-binding fragment thereof, binds PD-1.

E55. The method of any one of E52-E54, wherein said first antibody, or antigen-binding fragment thereof, binds human PD-1.

E56. The method of any one of E52-E55, wherein said first antibody is nivolumab, pembrolizumab, pidilizumab, or an antigen binding fragment thereof.

E57. The method of E52 or E53, wherein said first antibody, or antigen-binding fragment thereof, binds PD-L1, PD-L2, or both.

E58. The method of any one of E52-E53 and E57, wherein said first antibody, or antigen-binding fragment thereof, binds human PD-L1, PD-L2, or both.

E59. The method of any one of E52-E53 and E57-E58, wherein said first antibody is avelumab, atezolizumab, durvalumab, or an antigen binding fragment thereof.

E60. The method of any one of E52-E59, wherein said second antibody, or antigen-binding fragment thereof, binds LILRB1, LILRB2, or both.

E61. The method of any one of E52-E60, wherein said second antibody, or antigen-binding fragment thereof, binds human LILRB1, human LILRB2, or both.

E62. The method of any one of E52-E61, wherein said second antibody, or antigen-binding fragment thereof, binds both human LILRB1 and human LILRB2.

E63. The method of any one of E52-E59, wherein said second antibody, or antigen-binding fragment thereof, binds HLA-G.

E64. The method of any one of E52-E59 and E63, wherein said second antibody, or antigen-binding fragment thereof, binds human HLA-G.

E65. The method of any one of E52-E64, wherein said first antibody, or antigen-binding fragment thereof, and said second antibody, or antigen-binding fragment thereof, are administered concurrently.

E66. The method of any one of E52-E64, wherein said first antibody, or antigen-binding fragment thereof, and said second antibody, or antigen-binding fragment thereof, are administered sequentially.

E67. The method of E66, wherein one or more doses of said first antibody, or antigen-binding fragment thereof, are administered prior to administering said second antibody, or antigen-binding fragment thereof.

E58. The method of E66, wherein one or more doses of said second antibody, or antigen-binding fragment thereof, are administered prior to administering said first antibody, or antigen-binding fragment thereof.

E69. A method for treating a subject that has a tumor, wherein said subject is refractory to treatment with an anti-PD-1 antibody or antigen-binding fragment thereof, or an anti-PD-L1 antibody or antigen-binding fragment thereof, comprising: administering to the subject a therapeutically effective amount of (i) an antibody, or antigen-binding fragment thereof, that binds PD-1, PD-L1, or PD-L2; and (ii) a short interfering RNA (siRNA) that reduces the expression level of HLA-G, as compared to a control.

E70. The method of E69, wherein said subject is also refractory to treatment with an anti-LILRB1 antibody or antigen-binding fragment thereof, an anti-LILRB2 antibody or antigen-binding fragment thereof, an anti-HLA-G antibody or antigen-binding fragment thereof, or a short interfering RNA (siRNA) that reduces the expression level of HLA-G as compared to a control.

E71. The method of E70, wherein said siRNA comprises the nucleotide sequence of SEQ ID NO: 31.

E72. The method of any one of E52-E71, wherein said subject is a human.

E73. The method of any one of E52-E72, wherein the cancer is a solid tumor.

E74. The method of any one of E52-E73, wherein the cancer is brain cancer, bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, colorectal cancer, or gastric cancer.

E75. The method of any one of E52-E74, wherein said subject is refractory to treatment with an anti-PD-1 antibody or antigen-binding fragment thereof.

E76. The method of any one of E52-E75, wherein said subject is refractory to treatment with an anti-LILRB1 antibody or antigen-binding fragment thereof.

E77. The method of any one of E1-E3, E8-E28, E33-E55, and E60-E76, wherein said first antibody, or antigen-binding fragment thereof, binds PD-1 and comprises:

(i) a heavy chain variable region (VH) that comprises:
   (a) a VH complementarity determining region one (CDR-H1) comprising the amino acid sequence of SEQ ID NO: 19,
   (b) a VH CDR-H2 comprising the amino acid sequence of SEQ ID NO: 20; and
   (c) a VH CDR-H3 comprising the amino acid sequence of SEQ ID NO: 21; and
(ii) a light chain variable region (VL) that comprises:
   (a) a VL complementarity determining region one (CDR-L1) comprising the amino acid sequence of SEQ ID NO: 22,
   (b) a VL CDR-L2 comprising the amino acid sequence of SEQ ID NO: 23; and
   (c) a VL CDR-L3 comprising the amino acid sequence of SEQ ID NO: 24.

E78. The method of any one of E1-E3, E8-E28, E33-E55, and E60-E77, wherein said first antibody, or antigen-binding fragment thereof, comprises a VH that comprises the amino acid sequence of SEQ ID NO: 25.

E79. The method of any one of E1-E3, E8-E28, E33-E55, and E60-E78, wherein said first antibody, or antigen-binding fragment thereof, comprises a heavy chain constant region (CH) that comprises the amino acid sequence of SEQ ID NO: 29.

E80. The method of any one of E1-E3, E8-E28, E33-E55, and E60-E79, wherein said first antibody, or antigen-binding fragment thereof, comprises a VL that comprises the amino acid sequence of SEQ ID NO: 26.

E81. The method of any one of E1-E3, E8-E28, E33-E55, and E60-E80, wherein said first antibody, or antigen-binding fragment thereof, comprises a light chain constant region (CL) that comprises the amino acid sequence of SEQ ID NO: 30.

E82. The method of any one of E1-E3, E8-E28, E33-E55, and E60-E81, wherein said first antibody, or antigen-binding fragment thereof, comprises a heavy chain that comprises the amino acid sequence of SEQ ID NO: 27.

E83. The method of any one of E1-E3, E8-E28, E33-E55, and E60-E82, wherein said first antibody, or antigen-binding fragment thereof, comprises a light chain that comprises the amino acid sequence of SEQ ID NO: 28.

E84a. The method of any one of E1-E10, E13-E16, E19-E35, E38-E41, E44-E62, E65-E69, and E72-E83, wherein said second antibody, or antigen-binding fragment thereof, binds LILRB1 and comprises:

(i) a heavy chain variable region (VH) that comprises:
   (a) a VH complementarity determining region one (CDR-H1) comprising the amino acid sequence of SEQ ID NO: 36,
   (b) a VH CDR-H2 comprising the amino acid sequence of SEQ ID NO: 37; and
   (c) a VH CDR-H3 comprising the amino acid sequence of SEQ ID NO: 38; and (ii) a light chain variable region (VL) that comprises:
   (a) a VL complementarity determining region one (CDR-L1) comprising the amino acid sequence of SEQ ID NO: 39,
   (b) a VL CDR-L2 comprising the amino acid sequence of SEQ ID NO: 40; and
   (c) a VL CDR-L3 comprising the amino acid sequence of SEQ ID NO: 41.

E84b. The method of any one of E1-E10, E13-E16, E19-E35, E38-E41, E44-E62, E65-E69, E72-E83, and E84a, wherein said second antibody, or antigen-binding fragment thereof, comprises a VH that comprises the amino acid sequence of SEQ ID NO: 42.

E84c. The method of any one of E1-E10, E13-E16, E19-E35, E38-E41, E44-E62, E65-E69, E72-E83, and E84a-E84b, wherein said second antibody, or antigen-binding fragment thereof, comprises a heavy chain constant region (CH) that comprises the amino acid sequence of SEQ ID NO: 46.

E84d. The method of any one of E1-E10, E13-E16, E19-E35, E38-E41, E44-E62, E65-E69, E72-E83, and E84a-E84c, wherein said second antibody, or antigen-binding fragment thereof, comprises a VL that comprises the amino acid sequence of SEQ ID NO: 43.

E84e. The method of any one of E1-E10, E13-E16, E19-E35, E38-E41, E44-E62, E65-E69, E72-E83, and E84a-E84d, wherein said second antibody, or antigen-binding fragment thereof, comprises a light chain constant region (CL) that comprises the amino acid sequence of SEQ ID NO: 47.

E84f. The method of any one of E1-E10, E13-E16, E19-E35, E38-E41, E44-E62, E65-E69, E72-E83, and E84a-E84e, wherein said second antibody, or antigen-binding fragment thereof, comprises a heavy chain that comprises the amino acid sequence of SEQ ID NO: 44.

E84g. The method of any one of E1-E10, E13-E16, E19-E35, E38-E41, E44-E62, E65-E69, E72-E83, and E84a-E84f, wherein said second antibody, or antigen-binding fragment thereof, comprises a light chain that comprises the amino acid sequence of SEQ ID NO: 45.

E84h. The method of any one of E1-E10, E13-E16, E19-E35, E38-E41, E44-E62, E65-E69, and E72-E83, wherein said second antibody, or antigen-binding fragment thereof, binds LILRB1, and competes for binding to LILRB1 with an antibody or antigen-binding fragment thereof of any one of E84a-E84g.

E85a. The method of any one of E1-E10, E13-E16, E19-E35, E38-E41, E44-E62, E65-E69, and E72-E83, wherein said second antibody, or antigen-binding fragment thereof, binds LILRB1 and comprises:

(i) a heavy chain variable region (VH) that comprises:
   (a) a VH complementarity determining region one (CDR-H1) comprising the amino acid sequence of SEQ ID NO: 48,
   (b) a VH CDR-H2 comprising the amino acid sequence of SEQ ID NO: 49; and
   (c) a VH CDR-H3 comprising the amino acid sequence of SEQ ID NO: 50; and
(ii) a light chain variable region (VL) that comprises:
   (a) a VL complementarity determining region one (CDR-L1) comprising the amino acid sequence of SEQ ID NO: 51,
   (b) a VL CDR-L2 comprising the amino acid sequence of SEQ ID NO: 52; and
   (c) a VL CDR-L3 comprising the amino acid sequence of SEQ ID NO: 53.

E85b. The method of any one of E1-E10, E13-E16, E19-E35, E38-E41, E44-E62, E65-E69, E72-E83, and E85a, wherein said second antibody, or antigen-binding fragment thereof, comprises a VH that comprises the amino acid sequence of SEQ ID NO: 54.

E85c. The method of any one of E1-E10, E13-E16, E19-E35, E38-E41, E44-E62, E65-E69, E72-E83, and E85a-E85b, wherein said second antibody, or antigen-binding fragment thereof, comprises a heavy chain constant region (CH) that comprises the amino acid sequence of SEQ ID NO: 46.

E85d. The method of any one of E1-E10, E13-E16, E19-E35, E38-E41, E44-E62, E65-E69, E72-E83, and E85a-E85c, wherein said second antibody, or antigen-binding fragment thereof, comprises a VL that comprises the amino acid sequence of SEQ ID NO: 55.

E85e. The method of any one of E1-E10, E13-E16, E19-E35, E38-E41, E44-E62, E65-E69, E72-E83, and E85a-E85d, wherein said second antibody, or antigen-binding fragment thereof, comprises a light chain constant region (CL) that comprises the amino acid sequence of SEQ ID NO: 30.

E85f. The method of any one of E1-E10, E13-E16, E19-E35, E38-E41, E44-E62, E65-E69, E72-E83, and E85a-E85e, wherein said second antibody, or antigen-binding fragment thereof, comprises a heavy chain that comprises the amino acid sequence of SEQ ID NO: 56.

E85g. The method of any one of E1-E10, E13-E16, E19-E35, E38-E41, E44-E62, E65-E69, E72-E83, and E85a-E85f, wherein said second antibody, or antigen-binding fragment thereof, comprises a light chain that comprises the amino acid sequence of SEQ ID NO: 57.

E85h. The method of any one of E1-E10, E13-E16, E19-E35, E38-E41, E44-E62, E65-E69, and E72-E83, wherein said second antibody, or antigen-binding fragment thereof, binds LILRB1, and competes for binding to LILRB1 with an antibody or antigen-binding fragment thereof of any one of E85a-E85g.

E86a. The method of any one of E1-E10, E13-E16, E19-E35, E38-E41, E44-E62, E65-E69, and E72-E83, wherein said second antibody, or antigen-binding fragment thereof, binds LILRB1 and comprises:
  (i) a heavy chain variable region (VH) that comprises:
    (a) a VH complementarity determining region one (CDR-H1) comprising the amino acid sequence of SEQ ID NO: 58,
    (b) a VH CDR-H2 comprising the amino acid sequence of SEQ ID NO: 59; and
    (c) a VH CDR-H3 comprising the amino acid sequence of SEQ ID NO: 60; and
  (ii) a light chain variable region (VL) that comprises:
    (a) a VL complementarity determining region one (CDR-L1) comprising the amino acid sequence of SEQ ID NO: 61,
    (b) a VL CDR-L2 comprising the amino acid sequence of SEQ ID NO: 62; and
    (c) a VL CDR-L3 comprising the amino acid sequence of SEQ ID NO: 63.

E86b. The method of any one of E1-E10, E13-E16, E19-E35, E38-E41, E44-E62, E65-E69, E72-E83, and E86a, wherein said second antibody, or antigen-binding fragment thereof, comprises a VH that comprises the amino acid sequence of SEQ ID NO: 64.

E86c. The method of any one of E1-E10, E13-E16, E19-E35, E38-E41, E44-E62, E65-E69, E72-E83, and E86a-E86b, wherein said second antibody, or antigen-binding fragment thereof, comprises a heavy chain constant region (CH) that comprises the amino acid sequence of SEQ ID NO: 46.

E86d. The method of any one of E1-E10, E13-E16, E19-E35, E38-E41, E44-E62, E65-E69, E72-E83, and E86a-E86c, wherein said second antibody, or antigen-binding fragment thereof, comprises a VL that comprises the amino acid sequence of SEQ ID NO: 65.

E86e. The method of any one of E1-E10, E13-E16, E19-E35, E38-E41, E44-E62, E65-E69, E72-E83, and E86a-E86d, wherein said second antibody, or antigen-binding fragment thereof, comprises a light chain constant region (CL) that comprises the amino acid sequence of SEQ ID NO: 47.

E86f. The method of any one of E1-E10, E13-E16, E19-E35, E38-E41, E44-E62, E65-E69, E72-E83, and E86a-E86e, wherein said second antibody, or antigen-binding fragment thereof, comprises a heavy chain that comprises the amino acid sequence of SEQ ID NO: 66.

E86g. The method of any one of E1-E10, E13-E16, E19-E35, E38-E41, E44-E62, E65-E69, E72-E83, and E86a-E86f, wherein said second antibody, or antigen-binding fragment thereof, comprises a light chain that comprises the amino acid sequence of SEQ ID NO: 67.

E86h. The method of any one of E1-E10, E13-E16, E19-E35, E38-E41, E44-E62, E65-E69, and E72-E83, wherein said second antibody, or antigen-binding fragment thereof, binds LILRB1, and competes for binding to LILRB1 with an antibody or antigen-binding fragment thereof of any one of E86a-E86g.

E87a. An antibody, or antigen-binding fragment thereof, that binds LILRB1 and comprises:
  (i) a heavy chain variable region (VH) that comprises:
    (a) a VH complementarity determining region one (CDR-H1) comprising the amino acid sequence of SEQ ID NO: 36,
    (b) a VH CDR-H2 comprising the amino acid sequence of SEQ ID NO: 37; and
    (c) a VH CDR-H3 comprising the amino acid sequence of SEQ ID NO: 38; and
  (ii) a light chain variable region (VL) that comprises:
    (a) a VL complementarity determining region one (CDR-L1) comprising the amino acid sequence of SEQ ID NO: 39,
    (b) a VL CDR-L2 comprising the amino acid sequence of SEQ ID NO: 40; and
    (c) a VL CDR-L3 comprising the amino acid sequence of SEQ ID NO: 41.

E87b. The antibody, or antigen-binding fragment thereof, of E87a, comprising a VH that comprises the amino acid sequence of SEQ ID NO: 42.

E87c. The antibody, or antigen-binding fragment thereof, of E87a or E87b, comprising a heavy chain constant region (CH) that comprises the amino acid sequence of SEQ ID NO: 46.

E87d. The antibody, or antigen-binding fragment thereof, of any one of E87a-E87c, comprising a VL that comprises the amino acid sequence of SEQ ID NO: 43.

E87e. The antibody, or antigen-binding fragment thereof, of any one of E87a-E87d comprising a light chain constant region (CL) that comprises the amino acid sequence of SEQ ID NO: 47.

E87f. The antibody, or antigen-binding fragment thereof, of any one of E87a-E87e, comprising a heavy chain that comprises the amino acid sequence of SEQ ID NO: 44.

E87g. The antibody, or antigen-binding fragment thereof, of any one of E87a-E87f, comprising a light chain that comprises the amino acid sequence of SEQ ID NO: 45.

E87h. An antibody, or antigen-binding fragment thereof, that binds LILRB1, and competes for binding to LILRB1 with an antibody or antigen-binding fragment thereof of any one of E87a-E87g.

E87i. An antibody, or antigen-binding fragment thereof, that binds the D4 domain of LILRB1, wherein said D4 domain comprises residues 313-409 of SEQ ID NO: 3.

E87j. The antibody, or antigen-binding fragment thereof, of E87a-87i, wherein the antibody, or antigen binding fragment thereof, binds LILRB1 with a $K_D$ value of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E87k. The antibody, or antigen-binding fragment thereof, of E87j, wherein said $K_D$ value is measured by surface plasmon resonance (SPR), optionally using a Biacore® T200 instrument.

E87l. The antibody, or antigen-binding fragment thereof, of E87j, wherein said $K_D$ value is measured by bio-layer interferometry (BLI), optionally using a ForteBio Octet instrument.

E88a. An antibody, or antigen-binding fragment thereof, that binds LILRB1 and comprises:
- (i) a heavy chain variable region (VH) that comprises:
  - (a) a VH complementarity determining region one (CDR-H1) comprising the amino acid sequence of SEQ ID NO: 48,
  - (b) a VH CDR-H2 comprising the amino acid sequence of SEQ ID NO: 49; and
  - (c) a VH CDR-H3 comprising the amino acid sequence of SEQ ID NO: 50; and
- (ii) a light chain variable region (VL) that comprises:
  - (a) a VL complementarity determining region one (CDR-L1) comprising the amino acid sequence of SEQ ID NO: 51,
  - (b) a VL CDR-L2 comprising the amino acid sequence of SEQ ID NO: 52; and
  - (c) a VL CDR-L3 comprising the amino acid sequence of SEQ ID NO: 53.

E88b. The antibody, or antigen-binding fragment thereof, of E88a, comprising a VH that comprises the amino acid sequence of SEQ ID NO: 54.

E88c. The antibody, or antigen-binding fragment thereof, of E88a or E88b, comprising a heavy chain constant region (CH) that comprises the amino acid sequence of SEQ ID NO: 46.

E88d. The antibody, or antigen-binding fragment thereof, of any one of E88a-E88c, comprising a VL that comprises the amino acid sequence of SEQ ID NO: 55.

E88e. The antibody, or antigen-binding fragment thereof, of any one of E88a-E88d comprising a light chain constant region (CL) that comprises the amino acid sequence of SEQ ID NO: 30.

E88f. The antibody, or antigen-binding fragment thereof, of any one of E88a-E88e, comprising a heavy chain that comprises the amino acid sequence of SEQ ID NO: 56.

E88g. The antibody, or antigen-binding fragment thereof, of any one of E88a-E88f, comprising a light chain that comprises the amino acid sequence of SEQ ID NO: 57.

E88h. An antibody, or antigen-binding fragment thereof, that binds LILRB1, and competes for binding to LILRB1 with an antibody or antigen-binding fragment thereof of any one of E88a-E88g.

E88i. An antibody, or antigen-binding fragment thereof, that binds the D3 domain of LILRB1, wherein said D3 domain comprises residues 222-312 of SEQ ID NO: 3.

E88j. The antibody, or antigen-binding fragment thereof, of E88a-88i, wherein the antibody, or antigen binding fragment thereof, binds LILRB1 with a $K_D$ value of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E88k. The antibody, or antigen-binding fragment thereof, of E88j, wherein said $K_D$ value is measured by surface plasmon resonance (SPR), optionally using a Biacore T200 instrument.

E88l. The antibody, or antigen-binding fragment thereof, of E88j, wherein said $K_D$ value is measured by bio-layer interferometry (BLI), optionally using a ForteBio Octet instrument.

E89a. An antibody, or antigen-binding fragment thereof, that binds LILRB1 and comprises:
- (i) a heavy chain variable region (VH) that comprises:
  - (a) a VH complementarity determining region one (CDR-H1) comprising the amino acid sequence of SEQ ID NO: 58,
  - (b) a VH CDR-H2 comprising the amino acid sequence of SEQ ID NO: 59; and
  - (c) a VH CDR-H3 comprising the amino acid sequence of SEQ ID NO: 60; and
- (ii) a light chain variable region (VL) that comprises:
  - (a) a VL complementarity determining region one (CDR-L1) comprising the amino acid sequence of SEQ ID NO: 61,
  - (b) a VL CDR-L2 comprising the amino acid sequence of SEQ ID NO: 62; and
  - (c) a VL CDR-L3 comprising the amino acid sequence of SEQ ID NO: 63.

E89b. The antibody, or antigen-binding fragment thereof, of E89a, comprising a VH that comprises the amino acid sequence of SEQ ID NO: 64.

E89c. The antibody, or antigen-binding fragment thereof, of E89a or E89b, comprising a heavy chain constant region (CH) that comprises the amino acid sequence of SEQ ID NO: 46.

E89d. The antibody, or antigen-binding fragment thereof, of any one of E89a-E89c, comprising a VL that comprises the amino acid sequence of SEQ ID NO: 65.

E89e. The antibody, or antigen-binding fragment thereof, of any one of E89a-E89d comprising a light chain constant region (CL) that comprises the amino acid sequence of SEQ ID NO: 47.

E89f. The antibody, or antigen-binding fragment thereof, of any one of E89a-E89e, comprising a heavy chain that comprises the amino acid sequence of SEQ ID NO: 66.

E89g. The antibody, or antigen-binding fragment thereof, of any one of E89a-E89f, comprising a light chain that comprises the amino acid sequence of SEQ ID NO: 67.

E89h. An antibody, or antigen-binding fragment thereof, that binds LILRB1, and competes for binding to LILRB1 with an antibody or antigen-binding fragment thereof of any one of E89a-E89g.

E89i. An antibody, or antigen-binding fragment thereof, that binds the D4 domain of LILRB1, wherein said D4 domain comprises residues 313-409 of SEQ ID NO: 3.

E89j. The antibody, or antigen-binding fragment thereof, of E89a-89i, wherein the antibody, or antigen binding fragment thereof, binds LILRB1 with a $K_D$ value of or less than: about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM.

E89k. The antibody, or antigen-binding fragment thereof, of E89j, wherein said $K_D$ value is measured by surface plasmon resonance (SPR), optionally using a Biacore T200 instrument.

E89l. The antibody, or antigen-binding fragment thereof, of E89j, wherein said $K_D$ value is measured by bio-layer interferometry (BLI), optionally using a ForteBio Octet instrument.

E90. A composition for use in increasing IFN-γ expression level in a subject that has cancer, comprising (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E91. Use of a composition for increasing IFN-γ expression level in a subject that has cancer, said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E92. Use of a composition in the manufacture of a medicament for increasing IFN-γ expression level in a subject that has cancer, said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E93. A composition for use in increasing IFN-γ expression level in a subject that has cancer, comprising (i) an antibody, or antigen-binding fragment thereof, that binds PD-1, PD-L1, or PD-L2; and (ii) a short interfering RNA (siRNA) that reduces the expression level of HLA-G, as compared to a control.

E94. Use of a composition for increasing IFN-γ expression level in a subject that has cancer, said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E95. Use of a composition in the manufacture of a medicament for increasing IFN-γ expression level in a subject that has cancer, said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E96. A composition for use in increasing CD8+ T-cell mediated cytotoxicity in a subject that has cancer, comprising (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E97. Use of a composition for increasing CD8+ T-cell mediated cytotoxicity in a subject that has cancer, said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E98. Use of a composition in the manufacture of a medicament for increasing CD8+ T-cell mediated cytotoxicity in a subject that has cancer, said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E99. A composition for use in increasing CD8+ T-cell mediated cytotoxicity in a subject that has cancer, comprising (i) an antibody, or antigen-binding fragment thereof, that binds PD-1, PD-L1, or PD-L2; and (ii) a short interfering RNA (siRNA) that reduces the expression level of HLA-G, as compared to a control.

E100. Use of a composition for increasing CD8+ T-cell mediated cytotoxicity in a subject that has cancer, said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E101. Use of a composition in the manufacture of a medicament for increasing CD8+ T-cell mediated cytotoxicity in a subject that has cancer, said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E102. A composition for use in treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E103. Use of a composition for treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E104. Use of a composition in the manufacture of a medicament for treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) a first antibody, or antigen-binding fragment thereof, that binds PD-1, PD-L1, or PD-L2; and (ii) a second antibody, or antigen-binding fragment thereof, that binds LILRB1, LILRB2, or HLA-G.

E105. A composition for use in treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E106. Use of a composition for treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E107. Use of a composition in the manufacture of a medicament for treating cancer in a subject, wherein said subject is refractory to treatment with an anti-PD-1 antibody or antigen-binding fragment thereof, or with an anti-PD-L1 antibody or antigen-binding fragment thereof, and wherein said composition comprises (i) an antibody, or antigen-binding fragment thereof, that binds PD-1, PD-L1, or PD-L2; and (ii) a short interfering RNA (siRNA) that reduces the expression level of HLA-G, as compared to a control.

E108. A method of enhancing the T-cell mediated cytotoxicity against a cancer cell in a subject, comprising administering to the subject a therapeutically effective amount of (i) a Bi-specific T-cell engager (BiTE®) molecule; and (ii) an antibody, or antigen-binding fragment thereof, that binds LILRB1, LILRB2, or HLA-G.

E109. The method of E108, wherein said antibody, or antigen-binding fragment thereof, binds LILRB1.

E110. A method for treating a subject that has a tumor, wherein said subject is refractory to treatment with an anti-PD-1 antibody or antigen-binding fragment thereof, or with an anti-PD-L1 antibody or antigen-binding fragment thereof, comprising: administering to the subject a therapeutically effective amount of an antibody, or antigen-binding fragment thereof, that binds LILRB1, LILRB2, or HLA-G.

E111. The method of E110, wherein said antibody, or antigen-binding fragment thereof, binds LILRB1.

BRIEF DESCRIPTION OF THE FIGURES

FIGS. 1A-1D are graphs showing FACS analysis or RNA expression analysis of human CD8+ T cells from healthy donor PBMCs. FIGS. 1A-1B are representative FACS plots showing CD8+ T cell subsets, as defined by CD45RA and CCR7 expression, and their corresponding LILRB1 expression levels. Results from multiple donors were quantitated in FIG. 1C, which summarizes the quantitation of LILRB1 expression in Tem and Temra CD8+ T cells, as determined by FACS analysis (n=8). **P<0.01 with paired students' t-test. FIG. 1D shows LILRB1 mRNA expression levels in Tn, Tem and Temra subsets from both CD4+ and CD8+ T cells, as determined by RNA-sequencing analysis (n=2-6).

FIG. 2A is a representative FACS plot showing HLA-G expression on SK-MEL-2 cells (SK2, dotted line) and HLA-G transfected SK2 cells (SK2.HLA-G, solid line). Gray-filled histogram is isotype control. FIG. 2B shows representative histograms for CD69 expression on Temra cells co-cultured with SK2 cells (line histograms) or SK2.HLA-G cells (gray-filled histograms) for 45 h in the presence of 0.4 nM BiTE® molecule (right panel) or without BiTE® molecule (left panel). FIG. 2C shows the percentage CD8+ Temra cells that upregulate CD69 following co-culture with the indicated tumor cells for 18 h (left panel) or 45 h (right panel) in the presence of 0.4 nM BiTE® molecule. Percentage of CD69+ cells (mean±SD) were determined by FACS analysis. Data is representative of three independent experiments with two individual donors as T cell source. * p<0.05 with students' t-test. FIG. 2D shows BiTE® molecule-mediated cytotoxicity of isolated CD8+ Temra cells to indicated target cells in the presence of anti-LILRB1 blocking antibody (filled bars) or isotype control antibody (open bars). T cell and tumor cell co-culture with no BiTE® molecule was used as baseline to calculate specific lysis. Results shown as mean±SEM of T cells isolated from three donors (n=3).* p<0.05 with students' t-test.

FIG. 3 shows representative FACS plots of LILRB1 and PD-1 expression on CD8+ T cells isolated from the blood of healthy individuals after 48 hours of treatment with the indicated conditions. Histogram on the left shows isotype control staining of unstimulated CD8+ T cells. Results are representative of 5 donors analyzed across 3 experiments.

FIGS. 4A-4D show that LILRB1 and PD-1 are expressed by distinct CD8+ T cell subsets in tumor. FIG. 4A shows representative FACS plots of LILRB1 and PD-1 expression patterns on tumor infiltrated CD8+ T cells across three individual NSCLC patient tumor samples. Numbers represent percentage of cells in a given quadrant. FIG. 4B summarizes the quantitation of FIG. 4A from twelve NSCLC tumor patients. Percentage of total tumor CD8+ T cells that expressing LILRB1 (black filled), PD-1 (gray filled), or both (open) in each tumor is plotted. FIG. 4C shows the expression of CD69 from isolated tumor CD8+ T cells that were added to SK2 or SK2.HLA-G cell cultures together with BiTE® molecule for 45 h. Expression of CD69 measured as mean florescence intensity (MFI) on CD8+ T cells was determined by FACS analysis. Each type of symbols represented data obtained from a given individual. Data from each individual and mean±SEM shown in plot. **p<0.01 with paired students' t-test. FIG. 4D shows BiTE® molecule-mediated cytotoxicity of isolated tumor CD8+ cells to indicated target cells in the presence of anti-LILRB1 blocking antibody (gray-filled bars) or isotype control antibody (open bars). Individual symbols represent data obtained from a given individual. Data from each individual and mean±SEM are shown. * p<0.05 with paired students' t-test. ns, not significant.

FIGS. 5A-5B show the pattern of co-expression of various immune checkpoint proteins. FIG. 5A summarizes data based on published hepatocellular carcinoma (HCC) tumor infiltrating CD8+ T cells; numbers refer to % of LILRB1+ CD8+ cells (378 cells) or % of PD1+CD8+ cells (709 cells) that co-express indicated markers. FIG. 5B summarizes data from NSCLC tumor infiltrating CD8+ T cells; numbers refer to % of LILRB1+ CD8+ cells (22 cells) or % of PD1+ CD8+ cells (30 cells) that co-express indicated markers.

FIG. 6A shows the result of an MLR assay with isolated human CD8+ T cells and allogenic MDDCs in the presence of the indicated blocking antibodies. IFNγ in day 5 supernatants were measured by ELISA. Each group of bars represents results from T cells derived from an individual donor. FIG. 6B-6D shows the result of an MLR assay with isolated total human T cells and allogenic MDDCs in the presence of indicated blocking antibodies. IFNγ in day 5 supernatants were measured by ELISA. Each group of bars represents results from T cells derived from an individual donor. FIG. 6B shows MLR results from donors that responded to anti-PD-1 treatment. FIG. 6C shows MLR results from anti-PD-1 non-responding donors that responded to anti-LILRB1 treatment. FIG. 6D shows MLR result of a given donor pair that responded to both anti-PD-1 and anti-LILRB1 treatments.

**p<0.01 with students' t-test. Results are representative of three independent experiments with T cells from two individual donors.

FIGS. 8A-8D show that LILRB1 expression on the surface of CD8+ T cells is upregulated by effector cytokines and anti-PD1 blockade. FIG. 8A shows representative FACS plots of LILRB1 (left panel) and PD1 (right panel) expression on the surface of purified human CD8+ T cells upon TCR stimulation. Gray-filled histograms are control CD8+ T cells without stimulation. FIG. 8B shows quantitation from FIG. 8A (n=5 individual donors). *p<0.05 with students' t-test. ns, not significant. FIG. 8C shows representative FACS plots from purified human CD8+ Tem cells were activated with anti-CD3 plus anti-CD28 in the presence of 10 μg/ml recombinant human PDL1 (rhuPDL1, dashed lines) or human IgG1 (control, solid line). After 48 h, LILRB1 (left panel) and PD1 (right panel) expression was determined by FACS analysis. Gray-filled histograms are isotype staining controls. FIG. 8D shows quantitation of FIG. 8C. Representative data shown as mean±SD *p<0.05 with students' t-test. Three independent experiments were conducted with Tem cells isolated from three individual donors (n=3).

Figure 9A:
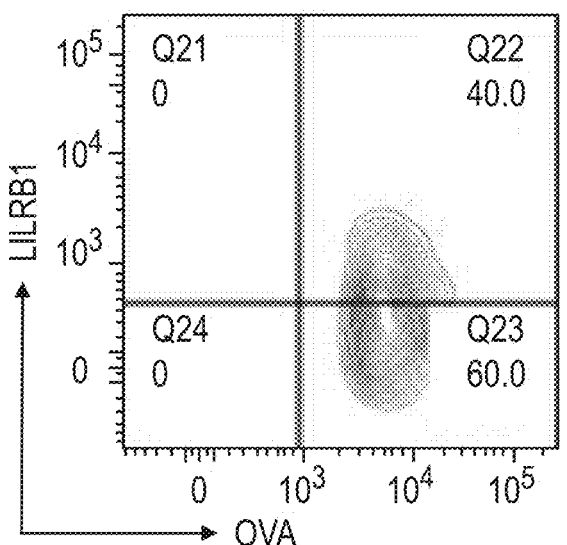
Figure 9B:
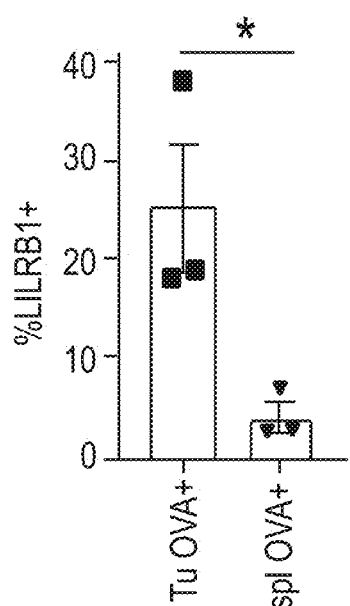

FIGS. 9A-9B show LILRB1 expression in tumor antigen (OVA)-specific CD8$^+$ T cells. FIG. 9A is a representative FACS plot showing LILRB1 expression on MC38.OVA tumor infiltrating CD8$^+$ T cells that were stained positive for OVA tetramer. FIG. 9B shows LILRB1 level in OVA-specific CD8$^+$ T cells in tumor or spleen from MC38.OVA tumor-bearing mice (n=3). *p<0.05 by paired students' t-test.

Figure 10:
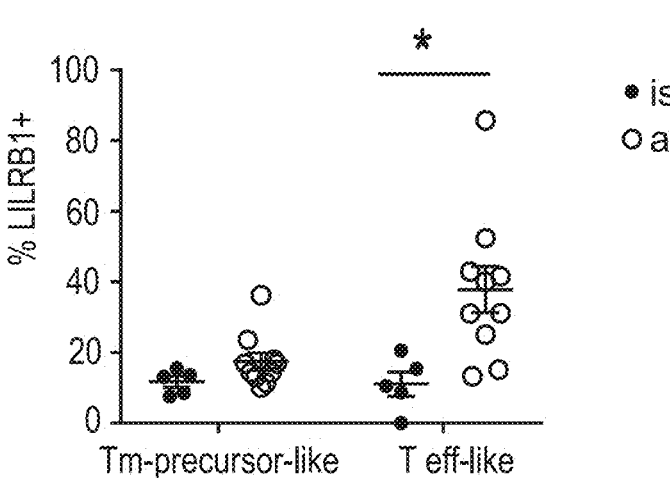

FIG. 10 shows that anti-PD1 increased LILRB1+ effector CD8 T cells in tumor. Tumor effector-like CD8+ T cells (Teff-like) were gated as PD1$^-$CD62L$^-$SLAMF7$^+$CX3CR1$^+$ and memory precursor-like CD8 T cells (Tm-precursor-like) were gated as PD1$^-$CD62L$^-$SLAMF7$^+$CX3CR1$^-$. LILRB1 expression was determined by FACS analysis (n=5-8). *p<0.05 by students' t-test.

DETAILED DESCRIPTION OF THE INVENTION

1. Overview

As disclosed and exemplified herein, the inventors discovered that the combination of (i) a PD-1 pathway inhibitor and (ii) a LILRB1/2 pathway inhibitor is surprisingly effective in increasing T-cell mediated cellular cytotoxicity against cancer cells, thereby providing a novel combination therapy for cancer treatment.

A number of immune checkpoint proteins, such as 4-1 BB and CTLA4, have been targeted in combination of PD-1. However, as disclosed and exemplified herein, these immune checkpoint proteins are generally co-expressed with PD-1 on the same population of dysfunctional T cells (see, e.g., FIGS. 5A-5B). Therefore, such combination therapy would be expected to modulate two different pathways on the same T cell. In general, combination therapy targeting two different pathways functioning on the same cell has the advantage of overcoming biological redundancy and avoiding the cancer cell developing drug resistance through mutation or upregulating expression of a single signaling pathway.

In contrast, the inventors discovered that the expression of PD-1 and LILRB1 is mutually exclusive. PD-1 is highly expressed in "effector memory T cells" (Tem), whereas LILRB1 is highly expressed in "effector T cells" (Teff).

Therefore, the combination of anti-PD-1 and anti-LILRB1 targets two different subtypes of CD8+ T cells, thereby mobilizing two different T cell subpopulations and significantly enhancing T-cell expression of effector cytokines, such as IFN-γ, and T-cell dependent cellular cytotoxicity against tumor cell targets. The combination is particularly effective in patients who may respond to anti-PD-1 treatment poorly. For certain patients (see, e.g., FIG. 7, Pair #1), mono-therapy using either anti-PD-1, or anti-LILRB1 failed to improve CD8+ T cell mediated cytotoxicity as compared to control. However, when anti-PD-1 and anti-LILRB1 are combined, the increase in CD8+ T cell cytotoxicity was more than doubled. Such synergistic effect of anti-PD-1 and anti-LILRB1 has not been observed in other combination therapies with PD-1.

Although not wishing to be bound by a particular theory, the inventors believe that by targeting LILBR1/2 signal pathway, the self-renewal of Teff, as well as the life-span of Teff, are both enhanced; by targeting PD-1 signaling pathway, the Tem exhaustion is reduced. The combined effect of targeting both pathways leads to expansion of two subsets of CD8+ T cells, thereby synergistically enhancing CD8−mediated anti-tumor activities.

2. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The term "antibody" refers to any form of immunoglobulin molecule that exhibits the desired biological or binding activity. Thus, it is used in the broadest sense and specifically covers, but is not limited to, monoclonal antibodies, polyclonal antibodies, multispecific antibodies (e.g., bispecific antibodies), humanized, fully human antibodies, chimeric antibodies and camelized single domain antibodies.

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibody and intrabody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al., Proc. Natl. Acad. Sci. USA 85:5879-5883 (1988)). Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al. Proc. Natl. Acad. Sci. USA 90:6444-6448 (1993); Poljak et al., 1994, Structure 2:1121-1123).

"Complementarity Determining Regions" (CDRs) can be identified according to the definitions of the Kabat, Chothia, the accumulation of both Kabat and Chothia, AbM, contact, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, Journal of Biological Chemistry, 283: 1 156-1 166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The CDR sequences of the exemplary PD-1 antibody (close 20C1) disclosed herein are defined according to Kabat (see, SEQ ID Nos. 19-24).

The term "treat," as well as words related thereto, do not necessarily imply 100% or complete cure. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of one or more conditions or symptoms or signs of the cancer being treated. Also, the treatment provided by the methods of the present disclosure can encompass slowing the progression of the cancer. For example, the methods can treat cancer by virtue of enhancing the T cell activity or an immune response against the cancer, reducing tumor or cancer growth, reducing metastasis of tumor cells, increasing cell death of tumor or cancer cells, and the like. In exemplary aspects, the methods treat by way of delaying the onset or recurrence of the cancer by 1 day, 2 days, 4 days, 6 days, 8 days, 10 days, 15 days, 30 days, two months, 4 months, 6 months, 1 year, 2 years, 4 years, or more. In exemplary aspects, the methods treat by way increasing the survival of the subject. The term "treatment" also includes prophylactic treatment.

3. Combination Therapy Inhibiting PD-1 Pathway and LILRB1/2 Pathway

Disclosed herein are combination therapy to inhibit PD-1 pathway and LILBR1/2 signaling pathway.

In one aspect, the invention provides a method for increasing IFN-γ expression level in a subject that has cancer, comprising administering to the subject a therapeutically effective amount of (i) a first antibody, or antigen-binding fragment thereof, that binds PD-1 or PD-L1; and (ii) a second antibody, or antigen-binding fragment thereof, that binds LILRB1, LILRB2, or HLA-G.

In another aspect, the invention provides a method for increasing IFN-γ expression level in a subject that has cancer, comprising administering to the subject a therapeutically effective amount of (i) a first antibody, or antigen-binding fragment thereof, that binds PD-1 or PD-L1; and (ii) a short interfering RNA (siRNA) that reduces the expression level of HLA-G, as compared to a control.

In another aspect, the invention provides a method for increasing CD8+ T-cell mediated cytotoxicity in a subject that has cancer, comprising administering to the subject a therapeutically effective amount of (i) a first antibody, or antigen-binding fragment thereof, that binds PD-1 or PD-L1; and (ii) a second antibody, or antigen-binding fragment thereof, that binds LILRB1, LILRB2, or HLA-G.

In another aspect, the invention provides a method for increasing CD8+ T-cell mediated cytotoxicity in a subject that has cancer, comprising administering to the subject a therapeutically effective amount of (i) a first antibody, or antigen-binding fragment thereof, that binds PD-1 or PD-L1; and (ii) a short interfering RNA (siRNA) that reduces the expression level of HLA-G, as compared to a control.

In another aspect, the invention provides a method for treating a subject that has a tumor, wherein said subject is refractory to treatment with an anti-PD-1 antibody or antigen-binding fragment thereof, or an anti-PD-L1 antibody or antigen-binding fragment thereof, comprising: administering to the subject a therapeutically effective amount of (i) a first antibody, or antigen-binding fragment thereof, that binds PD-1 or PD-L1; and (ii) a second antibody, or antigen-binding fragment thereof, that binds LILRB1, LILRB2, or HLA-G In another aspect, the invention provides a method for treating a subject that has a tumor, wherein said subject is refractory to treatment with an anti-PD-1 antibody or antigen-binding fragment thereof, or an anti-PD-L1 antibody or antigen-binding fragment thereof, comprising: administering to the subject a therapeutically effective amount of (i) a first antibody, or antigen-binding fragment thereof, that binds PD-1 or PD-L1; and (ii) a short interfering RNA (siRNA) that reduces the expression level of HLA-G, as compared to a control.

Also provided herein is a composition for use in increasing IFN-γ expression level in a subject that has cancer, said composition comprises (i) a first antibody, or antigen-binding fragment thereof, that binds PD-1 or PD-L1; and (ii) a second antibody, or antigen-binding fragment thereof, that binds LILRB1, LILRB2, or HLA-G.

Also provided herein is a composition for use in increasing IFN-γ expression level in a subject that has cancer, said composition comprises (i) a first antibody, or antigen-binding fragment thereof, that binds PD-1 or PD-L1; and (ii) a short interfering RNA (siRNA) that reduces the expression level of HLA-G, as compared to a control.

Also provided herein is a composition for use in increasing CD8+ T-cell mediated cytotoxicity in a subject that has cancer, said composition comprises (i) a first antibody, or antigen-binding fragment thereof, that binds PD-1 or PD-L1; and (ii) a second antibody, or antigen-binding fragment thereof, that binds LILRB1, LILRB2, or HLA-G.

Also provided herein is a composition for use in increasing CD8+ T-cell mediated cytotoxicity in a subject that has cancer, said composition comprises (i) a first antibody, or antigen-binding fragment thereof, that binds PD-1 or PD-L1; and (ii) a short interfering RNA (siRNA) that reduces the expression level of HLA-G, as compared to a control.

Also provided herein is a composition for use in treating a subject that has a tumor, wherein said subject is refractory to treatment with an anti-PD-1 antibody or antigen-binding fragment thereof, or an anti-PD-L1 antibody or antigen-binding fragment thereof, and wherein said composition comprises (i) a first antibody, or antigen-binding fragment thereof, that binds PD-1 or PD-L1; and (ii) a second antibody, or antigen-binding fragment thereof, that binds LILRB1, LILRB2, or HLA-G.

Also provided herein is a composition for use in treating a subject that has a tumor, wherein said subject is refractory to treatment with an anti-PD-1 antibody or antigen-binding fragment thereof, or an anti-PD-L1 antibody or antigen-binding fragment thereof, and wherein said composition comprises (i) a first antibody, or antigen-binding fragment thereof, that binds PD-1 or PD-L1; and (ii) a short interfering RNA (siRNA) that reduces the expression level of HLA-G, as compared to a control.

Also provided herein is a method for treating a subject that has a tumor, wherein said subject is refractory to treatment with an anti-PD-1 antibody or antigen-binding fragment thereof, or with an anti-PD-L1 antibody or antigen-binding fragment thereof, comprising: administering to the subject a therapeutically effective amount of an antibody, or antigen-binding fragment thereof, that binds LILRB1, LILRB2, or HLA-G. As exemplified herein, for cancer patients who are refractory to treatment with PD-1 pathway inhibitor, many are responsible to monotherapy using a LILRB1/2 pathway inhibitor (FIGS. 6A-6D). Therefore, the LILRB1/2 pathway inhibitors and their uses described herein are applicable to both monotherapy and combination therapy.

3.1 PD-1 Pathway Inhibitors

Programmed cell death protein 1, also known as PD-1 or CD279 (cluster of differentiation 279), is a cell surface receptor that plays an important role in down-regulating the immune system and promoting self-tolerance by suppressing T cell inflammatory activity. PD-1 is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells). Through these mechanisms, PD-1 inhibits the immune system. This prevents autoimmune diseases, but it can also prevent the immune system from killing cancer cells.

A new class of drugs that block PD-1 pathway (PD-1 pathway inhibitors) can activate the immune system to attack tumors, and are therefore used with varying success to treat some types of cancer. The PD-1 protein in humans is encoded by the PDCD1 gene. PD-1 is a cell surface receptor that belongs to the immunoglobulin superfamily and is expressed on T cells and pro-B cells. PD-1 binds two ligands, PD-L1 and PD-L2.

PD-1 pathway inhibitors disclosed herein include an antibody, or antigen binding fragment thereof, which specifically binds to PD-1 or PD-L1, in particular human PD-1 or human PD-L1. The antibody may be a human antibody, a humanized antibody, or a chimeric antibody. In some embodiments, the constant region of the antibody comprises the constant region from human IgG1, IgG2, IgG3, or IgG4.

The antigen binding fragment maybe, for example, Fab, Fab'-SH, F(ab')2, scFv and Fv fragments.

In certain embodiments, the antibody, or antigen-binding fragment thereof, binds to PD-1, such as human PD-1. Examples of antibodies that bind to human PD-1, are described, e.g., in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 antibodies useful for the invention described herein include, for example: K-3945 (Pembrolizumab, Keytruda®; U.S. Pat. No. 8,952,136); M-3475, a humanized IgG4 mAb with the structure described in WHO Drug Information, Vol. 27, No. 2, pages 161-162 (2013); nivolumab (BMS-936558), a human IgG4 mAb with the structure described in WHO Drug Information, Vol. 27, No. 1, pages 68-69 (2013); the humanized antibodies h409A11, h409A16 and h409A17, which are described in WO2008/156712; AMP-514, which is being developed by MedImmune; humanized antibody CT-011 (Pidilizumab) a monoclonal antibody being developed by Medivation, and anti-PD-1 antibodies disclosed in WO2015/119923 (the heavy and light chains comprise SEQ ID NO: 21 and SEQ ID NO: 22, respectively).

In certain embodiments, the anti-PD-1 antibody binds to cynomolgus PD-1. In exemplary embodiments, the anti-PD-1 antibody binds to both human PD-1 and cynomolgus PD-1.

In certain embodiments, the antibody, or antigen-binding fragment thereof, binds to PD-L1, such as human PD-L1. Examples of mAbs that bind to human PD-L1 are described, e.g., in WO2013/019906, WO2010/077634 and U.S. Pat. No. 8,383,796. Specific anti-human PD-L1 antibodies useful for the invention described herein include, for example, MPDL3280A (Atezolizumab), MEDI4736 (Durvalumab), SB0010718C (Avelumab), BMS-936559, and an antibody which comprises the heavy chain and light chain variable regions of SEQ ID NO: 24 and SEQ ID NO: 21, respectively, of WO2013/019906.

In certain embodiments, the anti-PD-1 antibody, or antigen-binding fragment thereof, binds to cynomolgus PD-L1. In exemplary embodiments, the anti-PD-L1 antibody, or antigen-binding fragment thereof, binds to both human PD-L1 and cynomolgus PD-L1.

In certain embodiments, the antibody or antigen-binding fragment thereof described herein inhibits the signal transduction resulting from the interaction of PD-1 with one or more of its binding partners, such as PD-L1, or PD-L2. In certain embodiments, the antibody, or antigen-binding fragment thereof, inhibits at least about 40%, at least about 50%, at least about 60%, at least about 70%, at least about 80%, or at least about 90% of the binding interactions between PD-1 and PD-L1 or PD-L2.

In an exemplary embodiment, the invention provides an antibody, or antigen-binding fragment thereof, that specifically binds human PD-1, comprising: (i) a heavy chain variable region (VH) that comprises: a VH complementarity determining region one (CDR-H1) comprising the amino acid sequence of SEQ ID NO: 19, a VH CDR-H2 comprising the amino acid sequence of SEQ ID NO: 20; and a VH CDR-H3 comprising the amino acid sequence of SEQ ID NO: 21; and (ii) a light chain variable region (VL) that comprises: a VL complementarity determining region one (CDR-L1) comprising the amino acid sequence of SEQ ID NO: 22, a VL CDR-L2 comprising the amino acid sequence of SEQ ID NO: 23; and (c) a VL CDR-L3 comprising the amino acid sequence of SEQ ID NO: 24.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO:19, a CDR-H2 sharing at least 90%, at least 91%, at least 92%, at least 93%, at least 94%, or at least 95% identity with SEQ ID NO: 20, and a CDR-H3 sharing at least 90%, at least 91%, at least 92%, at least 93%, at least 94%, or at least 95% identity with SEQ ID NO: 21; and/or (ii) the following light chain CDR sequences: a CDR-L1 sharing at least 90%, at least 91%, at least 92%, at least 93%, at least 94%, or at least 95% identity with SEQ ID NO: 22, a CDR-L2 sharing at least 90%, at least 91%, at least 92%, at least 93%, at least 94%, or at least 95% identity with SEQ ID NO: 23, and a CDR-L3 sharing at least 90%, at least 91%, at least 92%, at least 93%, at least 94%, or at least 95% identity with SEQ ID NO: 24.

In certain embodiments, no more than 5, no more than 4, no more than 3, no more than 3, no more than 2, or no more than one substitution is made in the sequence of CDR-L1, relative to SEQ ID NO. 22. In certain embodiments, no more than 4, no more than 3, no more than 3, no more than 2, or no more than one substitution is made in the sequence of CDR-L2, relative to SEQ ID NO. 23. In certain embodiments, no more than 5, no more than 4, no more than 3, no more than 3, no more than 2, or no more than one substitution is made in the sequence of CDR-L3, relative to SEQ ID NO. 24. In certain embodiments, no more than 3, no more than 2, or no more than one substitution is made in the sequence of CDR-H1, relative to SEQ ID NO. 19. In certain embodiments, no more than 10, no more than 9, no more than 8, no more than 7, no more than 6, no more than 5, no more than 4, no more than 3, no more than 3, no more than 2, or no more than one substitution is made in the sequence of CDR-H2, relative to SEQ ID NO. 20. In certain embodiments, no more than 5, no more than 4, no more than 3, no more than 3, no more than 2, or no more than one substitution is made in the sequence of CDR-H3, relative to SEQ ID NO. 21. In certain embodiments, the substitution does not change binding affinity ($K_D$) value by more than 3 orders of magnitude, more than 2 orders of magnitude, or 1 order of magnitude, as compared with the $K_D$ of the antibody, or antigen-binding fragment thereof, without the substitution.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 25, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 26. Any combination of these VL and VH sequences is also encompassed by the invention In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 29; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 30. Any combination of these CH and CL sequences is also encompassed by the invention.

In certain embodiments, the antibody or antigen-binding fragment thereof described herein comprises an Fc domain. The Fc domain can be derived from IgA (e.g., IgA1 or IgA2), IgG, IgE, or IgG (e.g., IgG1, IgG2, IgG3, or IgG4).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 27, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 28. Any combination of these heavy chain and light chain sequences is also encompassed by the invention.

Sometimes, the C-terminal lysine of an antibody heavy chain undergoes cleavage by carboxypeptidase during expression. Accordingly, in some aspects, the anti-PD-1 antibody comprises a heavy chain constant region lacking the C-terminal Lys. A heavy chain constant region lacking the C-terminal Lys advantageously prevents carboxypeptidase to act on the heavy chain of the anti-PD-1 antibody.

In certain embodiments, the anti-PD-1 antibody, antigen binding antibody fragment thereof, or anti-PD-1 antibody protein product comprises one or more amino acid modifications, relative to the naturally-occurring counterpart, in order to improve half-life/stability or to render the antibody more suitable for expression/manufacturability. In exemplary embodiments, the anti-PD-1 antibody is designed to prevent or reduce interaction between the anti-PD-1 antibody and Fc receptors. In exemplary instances, the anti-PD-1 antibody is a Stable Effector Functionless (SEFL) antibody comprising a constant region that lacks the ability to interact with Fcγ receptors. SEFL antibodies are known in the art. See, e.g., Liu et al., J Biol Chem 292: 1876-1883 (2016); and Jacobsen et al., J. Biol. Chem. 292: 1865-1875 (2017). In exemplary aspects, the SEFL antibody comprises one or more of the following mutations, numbered according to the EU system: L242C, A287C, R292C, N297G, V302C, L306C, and/or K334C. In exemplary aspects, the SEFL antibody comprises N297G. In exemplary aspects, the SEFL antibody comprises A287C, N297G, and L306C. In other exemplary aspects, the SEFL antibody comprises R292C, N297G, and V302C (i.e., SEFL2-2).

Additional antibodies, or antigen-binding fragment thereof, of the invention can be obtained using PD-1 or PD-L1 (or antigenic fragment thereof) as an antigen. Exemplary sequences of human PD-1 and PD-L1 are provided herein as SEQ ID Nos. 1 and 2, respectively. Using these exemplary sequences as antigens, antibodies (or antigen-binding fragments thereof) of the invention can be obtained using art-known methods. For example, monoclonal antibodies may be made by the hybridoma method, or may be made by recombinant DNA methods. The antibodies may also be isolated from phage antibody libraries.

In certain embodiments, the antibody, or antigen-binding fragment thereof, of the invention binds to SEQ ID NO:1, or an antigenic fragment of SEQ ID NO:1. In certain embodiments, the antibody, or antigen-binding fragment thereof, of the invention binds to an amino acid sequence that is at least 70%, at least 75%, at least 80%, at least 85%, at least 90%, at least 95%, at least 97%, or at least 99% identical to SEQ ID NO:1, or an antigenic fragment of SEQ ID NO:1.

In certain embodiments, the antibody, or antigen-binding fragment thereof, of the invention binds to SEQ ID NO:2, or an antigenic fragment of SEQ ID NO:2. In certain embodiments, the antibody, or antigen-binding fragment thereof, of the invention binds to an amino acid sequence that is at least 70%, at least 75%, at least 80%, at least 85%, at least 90%, at least 95%, at least 97%, or at least 99% identical to SEQ ID NO:2, or an antigenic fragment of SEQ ID NO:2.

Other PD-1 pathway inhibitors that are useful for the invention include, for example, an immunoadhesin that specifically binds to PD-1 or PD-L1, a fusion protein comprising the extracellular or PD-1 binding portion of PD-L1 or PD-L2 fused to a constant region, such as an Fc region of an immunoglobulin molecule. Examples of immunoadhesion molecules that specifically bind to PD-1 are described in WO2010/027827 and WO201 1/066342. Examples of fusion proteins that are useful as PD-1 pathway inhibitors include AMP-224 (also known as B7-DCIg), which is a PD-L2-Fc fusion protein and binds to human PD-1.

Antisense RNA, or small interfering RNA (siRNA) may also be used as PD-1 pathway inhibitors. Various art-known methods can be used to analyze the sequence of PD-1 and PD-L1 (such as SEQ ID Nos. 1 and 2) to obtain antisense RNA or siRNA that inhibits the expression of PD-1 and/or PD-L1. Several siRNA design algorithms have emerged recently to offer high success rates for silencing human genes. Examples of such algorithms include, e.g., Cenix algorithm, and GeneLink RNAi Explorer. General parameters for siRNA design strategies may include, for example, (1) low to medium GC content (30-50%); (2) absence of internal repeats or palindromes; (3) presence of an A at position 3 of the sense strand; (4) presence of A at position 19 of the sense strand; (5) absence of G or C at position 19 of the sense strand; (6) presence of U at position 10 of the sense strand; (7) absence of a G at position 13 of the sense strand; and/or (8) at least 3 A/Us at positions 15-19 of the sense strand.

In some embodiments, the PD-1 pathway inhibitor described herein reduces the negative co-stimulatory signal mediated by or through cell surface proteins expressed on T lymphocytes mediated signaling through PD-1, so to render a dysfunctional T-cell less dysfunctional (e.g., enhancing effector responses to antigen recognition).

3.2. LILRB1/2 Pathway Inhibitors

The leukocyte immunoglobulin-like receptors (LILR) are a family of receptors possessing extracellular immunoglobulin domains. They are also known as CD85, ILTs and LIR, and can exert immunomodulatory effects on a wide range of immune cells. The human genes encoding these receptors are found in a gene cluster at chromosomal region 19q13.4. They include, LILRA1, LILRA2, LILRA3, LILRA4, LILRA5, LILRA6, LILRB1, LILRB2, LILRB3, LILRB4, LILRB5, LILRB6 or LILRA6, and LILRB7 or LILRA5. A subset of LILRs recognize MHC class I molecules (also known as HLA class I in humans). Of these, the inhibitory receptors LILRB1 and LILRB2 show a broad specificity for classical and non-classical MHC alleles with preferential binding to b2m-associated complexes. In contrast, the activating receptors LILRA1 and LILRA3 prefer b2m-independent free heavy chains of MHC class I, and in particular HLA-C alleles.

Leukocyte immunoglobulin-like receptor subfamily B member 1 (LILRB1) is a protein that in humans is encoded by the LILRB1 gene. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. LILRB1 was also reported to be expressed in human gastric cancer cells and may enhance tumor growth. It is thought to control inflammatory responses and cytotoxicity to help focus the immune response and limit autoreactivity. Multiple transcript variants encoding different isoforms have been found for this gene. LILRB1 is also known as ILT2, ILT-2, CD85, CD85J, LIR1, LIR-1, and MIR7. The human LILRB1 protein have several different isoforms. Examples of such isoforms are provided herein as SEQ ID Nos. 3-7. These sequences are not exhaustive, and a skilled artisan would know that other isoforms and polymorphisms exist, and that their sequences are readily available from public databases.

Leukocyte immunoglobulin-like receptor subfamily B member 2 (LILRB2) is a protein that in humans is encoded by the LILRB2 gene. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on immune cells where it binds to MHC class I molecules on antigen-presenting cells and transduces a negative signal that inhibits stimulation of an immune response. It is thought to control inflammatory responses and cytotoxicity to help focus the immune response and limit autoreactivity. The receptor is also expressed on human non-small cell lung cancer cells (see Sun et al., Chest. 2008, 134:783-788). Multiple transcript variants encoding different isoforms have been found for this gene. LILRB2 has been shown to interact with PTPN6. The human LILRB2 protein also have several different isoforms. Examples of such isoforms are provided herein as SEQ ID Nos. 8-11. These sequences are not exhaustive, and a skilled artisan would know that other isoforms and polymorphisms exist, and that their sequences are readily available from public databases.

A major histocompatibility complex (MHC) Class I complex is made of human leukocyte antigen (HLA) alpha chains and a beta-2-macroglobulin protein (B2M) that assemble to form a complex. HLA alpha chains in humans include the alpha chains HLA-A, HLA-B, HLA-C, HLA-E, HLA-F, HLA-G, HLA-K, and HLA-L. The HLA-A, HLA-B, and HLA-C alpha chains are typically referred to as classical HLA alpha chains. Non-classical MHC Class I HLA alpha chains include HLA-E, HLA-F, HLA-G, HLA-K, and HLA-L.

HLA-G is encoded by a nonclassical class Ib gene, and HLA-G protein possesses some unusual characteristics, including restricted expression, limited number of polymorphisms, and alternatively spliced mRNA variants. The genomic structure of HLA-G is similar to other class I genes, however HLA-G is unique in several other respects. The HLA-G gene has eight exons encoding a signal peptide (exon 1), the a1, a2, and a3 domains (exons 2, 3, and 4, respectively), the transmembrane domain (exon 5) and the intracellular domain (exons 6 and 7). The premature stop codon in exon 6 is responsible in slower turnover, prolonged expression of HLA-G at the cell surface, and the inefficient presentation of exogenous peptides (Park, B., et al., Immunity, 15:213 (2001)). Another unique future of HLA-G is that it encodes at least seven isoforms as a result of alternative splicing (HLA-G1 to HLA-G7). The full-length membrane-bound isoforms, HLA-G1, is structurally similar to other class I genes, except for the truncated cytoplasmic tail. A stop sequence in intron 4 results in two soluble isoforms, HLA-G5 and HLA-G6.

HLA-G exists in numerous isoforms and polymorphisms. Examples of some HLA-G sequences are provided herein as SEQ ID Nos. 12-18. These sequences are not exhaustive, and a skilled artisan would know that other isoforms and polymorphisms exist, and that their sequences are readily available from public databases. For example, the following GenBank Accession Nos. refer to HLA-G: NM_002127.5, XM_006715080.1, XM_006725041.1, XM_006725700.1, and XM_006725909.1.

As described herein, the inventors believe that the LILRB1/2 pathway inhibits immune cell function. Through the interaction between LILRB1/2 and HLA-G, a number of immune cell functions are suppressed, including, for example: NK/CD8 cell mediated cytolytic activity, DC cell maturation and IL-12 production, macrophage phagocytosis, and B cell proliferation and antibody production. Accordingly, inhibiting LILRB1/2 pathway can be an attractive mechanism for cancer treatment.

LILRB1/2 pathway inhibitors disclosed herein include an antibody, or antigen binding fragment thereof, which specifically binds to LILRB1, LILRB2, or HLA-G, in particular human LILRB1, human LILRB2, or human HLA-G. The antibody may be a human antibody, a humanized antibody, or a chimeric antibody. In some embodiments, the constant region of the antibody comprises the constant region from human IgG1, IgG2, IgG3, or IgG4. The antigen binding fragment maybe, for example, Fab, Fab'-SH, F(ab')2, scFv and Fv fragments.

In certain embodiments, the antibody, or antigen-binding fragment thereof, binds to LILRB1, such as human LILRB1. Examples of anti-LILRB1 antibodies include, e.g., Human LILRB1/CD85j/ILT2 antibody clones MAB20171 and MAB20172 (available from R&D Systems); anti-LILRB1 clone 3D3-1D12 (available from Sigma-Aldrich); anti-LILRB1 clone GH1/75 (available from Novus Biologicals); and anti-LILRB4 antibodies that also cross-react with LILRB1, as described in US2018/0086829. These antibodies are from non-human species. For treatment of human subjects, it would be describable to further humanize these antibodies, using commonly-known methods in the art, such as CDR grafting.

In certain embodiments, the antibody, or antigen-binding fragment thereof, binds to LILRB2, such as human LILRB2. Examples of anti-LILRB2 antibodies. Examples of anti-LILRB2 antibodies include, e.g., Human LILRB2/CD85d/ILT4 antibody clone MAB2078 (available from R&D Systems); anti-LILRB2 clone 1D4 (available from Sigma-Aldrich); and anti-LILRB4 antibodies that also cross-react with LILRB1, as described in US2018/0086829. Again, for treatment of human subjects, it would be describable to further humanize these non-human antibodies using commonly-known methods in the art, such as CDR grafting.

In certain embodiments, the antibody, or antigen-binding fragment thereof, binds both LILRB1 and LILRB2. In certain embodiments, the antibody, or antigen-binding fragment thereof, binds both human LILRB1 and human LILRB2.

In certain embodiments, the antibody, or antigen-binding fragment thereof, binds to HLA-G, such as human HLA-G.

Examples of anti-HLA-G antibodies can be found, e.g., in WO 2017/207775 and WO2014/072534.

In certain, the antibody described here inhibits the signal transduction resulting from the interaction of LILRB1/LILBR2 with one or more of its binding partners, such as HLA-G. In certain embodiments, the antibody inhibits at least about 40%, at least about 50%, at least about 60%, at least about 70%, at least about 80%, or at least about 90% of the binding interactions between LILRB1 and HLA-G, or between LILRB2 and HLA-G.

In an exemplary embodiment, the invention provides an antibody, or antigen-binding fragment thereof, that specifically binds human LILRB1, comprising: (i) a heavy chain variable region (VH) that comprises: a VH complementarity determining region one (CDR-H1) comprising the amino acid sequence of SEQ ID NO: 36, a VH CDR-H2 comprising the amino acid sequence of SEQ ID NO: 37; and a VH CDR-H3 comprising the amino acid sequence of SEQ ID NO: 38; and (ii) a light chain variable region (VL) that comprises: a VL complementarity determining region one (CDR-L1) comprising the amino acid sequence of SEQ ID NO: 39, a VL CDR-L2 comprising the amino acid sequence of SEQ ID NO: 40; and (c) a VL CDR-L3 comprising the amino acid sequence of SEQ ID NO: 41.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO:36, a CDR-H2 sharing at least 90%, at least 91%, at least 92%, at least 93%, at least 94%, or at least 95% identity with SEQ ID NO: 37, and a CDR-H3 sharing at least 90%, at least 91%, at least 92%, at least 93%, at least 94%, or at least 95% identity with SEQ ID NO: 38; and/or (ii) the following light chain CDR sequences: a CDR-L1 sharing at least 90%, at least 91%, at least 92%, at least 93%, at least 94%, or at least 95% identity with SEQ ID NO: 39, a CDR-L2 sharing at least 90%, at least 91%, at least 92%, at least 93%, at least 94%, or at least 95% identity with SEQ ID NO: 40, and a CDR-L3 sharing at least 90%, at least 91%, at least 92%, at least 93%, at least 94%, or at least 95% identity with SEQ ID NO: 41.

In certain embodiments, no more than 5, no more than 4, no more than 3, no more than 3, no more than 2, or no more than one substitution is made in the sequence of CDR-L1, relative to SEQ ID NO. 39. In certain embodiments, no more than 4, no more than 3, no more than 3, no more than 2, or no more than one substitution is made in the sequence of CDR-L2, relative to SEQ ID NO. 40. In certain embodiments, no more than 5, no more than 4, no more than 3, no more than 3, no more than 2, or no more than one substitution is made in the sequence of CDR-L3, relative to SEQ ID NO. 41. In certain embodiments, no more than 3, no more than 2, or no more than one substitution is made in the sequence of CDR-H1, relative to SEQ ID NO. 36. In certain embodiments, no more than 10, no more than 9, no more than 8, no more than 7, no more than 6, no more than 5, no more than 4, no more than 3, no more than 3, no more than 2, or no more than one substitution is made in the sequence of CDR-H2, relative to SEQ ID NO. 37. In certain embodiments, no more than 5, no more than 4, no more than 3, no more than 3, no more than 2, or no more than one substitution is made in the sequence of CDR-H3, relative to SEQ ID NO. 38. In certain embodiments, the substitution does not change binding affinity ($K_D$) value by more than 3 orders of magnitude, more than 2 orders of magnitude, or 1 order of magnitude, as compared with the $K_D$ of the antibody, or antigen-binding fragment thereof, without the substitution.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 42, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 43. Any combination of these VL and VH sequences is also encompassed by the invention.

In certain embodiments, the antibody or antigen-binding fragment thereof described herein comprises a human immunoglobulin kappa constant domain sequence (e.g., SEQ ID NO:30). In certain embodiments, the antibody or antigen-binding fragment thereof described herein comprises a human immunoglobulin lambda constant domain sequence (e.g., SEQ ID NO:47).

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 46; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 47. Any combination of these CH and CL sequences is also encompassed by the invention.

In certain embodiments, the antibody or antigen-binding fragment thereof described herein comprises an Fc domain. The Fc domain can be derived from IgA (e.g., IgA1 or IgA2), IgG, IgE, or IgG (e.g., IgG1, IgG2, IgG3, or IgG4).

In certain embodiments, the antibody or antigen-binding fragment thereof described herein comprises a human immunoglobulin heavy constant gamma 4 (IgG4) sequence (e.g., SEQ ID NO: 46). In certain embodiments, the antibody or antigen-binding fragment thereof described herein comprises a human immunoglobulin heavy constant gamma 1 (IgG1) sequence (e.g., SEQ ID NO: 68). In certain embodiments, the antibody or antigen-binding fragment thereof described herein comprises a human immunoglobulin heavy constant gamma 2 (IgG2) sequence (e.g., SEQ ID NO: 69). In certain embodiments, the antibody or antigen-binding fragment thereof described herein comprises a human immunoglobulin heavy constant gamma 3 (IgG3) sequence (e.g., SEQ ID NO: 70).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 44, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 45. Any combination of these heavy chain and light chain sequences is also encompassed by the invention.

In an exemplary embodiment, the invention provides an antibody, or antigen-binding fragment thereof, that specifically binds human LILRB1, comprising: (i) a heavy chain variable region (VH) that comprises: a VH complementarity determining region one (CDR-H1) comprising the amino acid sequence of SEQ ID NO: 48, a VH CDR-H2 comprising the amino acid sequence of SEQ ID NO: 49; and a VH CDR-H3 comprising the amino acid sequence of SEQ ID NO: 50; and (ii) a light chain variable region (VL) that comprises: a VL complementarity determining region one (CDR-L1) comprising the amino acid sequence of SEQ ID NO: 51, a VL CDR-L2 comprising the amino acid sequence of SEQ ID NO: 52; and (c) a VL CDR-L3 comprising the amino acid sequence of SEQ ID NO: 53.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO:48, a CDR-H2 sharing at least 90%, at least 91%, at least 92%, at least 93%, at least 94%, or at least 95% identity with SEQ ID NO: 49, and a CDR-H3 sharing at least 90%, at least 91%, at least 92%, at least 93%, at least 94%, or at least 95% identity with SEQ ID NO: 50; and/or (ii) the following light chain CDR sequences: a CDR-L1 sharing at least 90%, at least 91%, at least 92%, at least 93%, at least 94%, or at least 95% identity with SEQ ID NO: 51, a CDR-L2 sharing at least 90%, at least 91%, at least 92%, at least 93%, at least 94%, or at least 95% identity with SEQ ID NO: 52, and a CDR-L3 sharing at least 90%, at least 91%, at least 92%, at least 93%, at least 94%, or at least 95% identity with SEQ ID NO: 53.

In certain embodiments, no more than 5, no more than 4, no more than 3, no more than 3, no more than 2, or no more than one substitution is made in the sequence of CDR-L1, relative to SEQ ID NO. 51. In certain embodiments, no more than 4, no more than 3, no more than 3, no more than 2, or no more than one substitution is made in the sequence of CDR-L2, relative to SEQ ID NO. 52. In certain embodiments, no more than 5, no more than 4, no more than 3, no more than 3, no more than 2, or no more than one substitution is made in the sequence of CDR-L3, relative to SEQ ID NO. 53. In certain embodiments, no more than 3, no more than 2, or no more than one substitution is made in the sequence of CDR-H1, relative to SEQ ID NO. 48. In certain embodiments, no more than 10, no more than 9, no more than 8, no more than 7, no more than 6, no more than 5, no more than 4, no more than 3, no more than 3, no more than 2, or no more than one substitution is made in the sequence of CDR-H2, relative to SEQ ID NO. 49. In certain embodiments, no more than 5, no more than 4, no more than 3, no more than 3, no more than 2, or no more than one substitution is made in the sequence of CDR-H3, relative to SEQ ID NO. 50. In certain embodiments, the substitution does not change binding affinity ($K_D$) value by more than 3 orders of magnitude, more than 2 orders of magnitude, or 1 order of magnitude, as compared with the $K_D$ of the antibody, or antigen-binding fragment thereof, without the substitution.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 54, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 55. Any combination of these VL and VH sequences is also encompassed by the invention.

In certain embodiments, the antibody or antigen-binding fragment thereof described herein comprises a human immunoglobulin kappa constant domain sequence (e.g., SEQ ID NO:30). In certain embodiments, the antibody or antigen-binding fragment thereof described herein comprises a human immunoglobulin lambda constant domain sequence (e.g., SEQ ID NO:47).

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 46; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 30. Any combination of these CH and CL sequences is also encompassed by the invention.

In certain embodiments, the antibody or antigen-binding fragment thereof described herein comprises an Fc domain. The Fc domain can be derived from IgA (e.g., IgA1 or IgA2), IgG, IgE, or IgG (e.g., IgG1, IgG2, IgG3, or IgG4).

In certain embodiments, the antibody or antigen-binding fragment thereof described herein comprises a human immunoglobulin heavy constant gamma 4 (IgG4) sequence (e.g., SEQ ID NO: 46). In certain embodiments, the antibody or antigen-binding fragment thereof described herein comprises a human immunoglobulin heavy constant gamma 1 (IgG1) sequence (e.g., SEQ ID NO: 68). In certain embodiments, the antibody or antigen-binding fragment thereof described herein comprises a human immunoglobulin heavy constant gamma 2 (IgG2) sequence (e.g., SEQ ID NO: 69). In certain embodiments, the antibody or antigen-binding fragment thereof described herein comprises a human immunoglobulin heavy constant gamma 3 (IgG3) sequence (e.g., SEQ ID NO: 70).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 56, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 57. Any combination of these heavy chain and light chain sequences is also encompassed by the invention.

In an exemplary embodiment, the invention provides an antibody, or antigen-binding fragment thereof, that specifically binds human LILRB1, comprising: (i) a heavy chain variable region (VH) that comprises: a VH complementarity determining region one (CDR-H1) comprising the amino acid sequence of SEQ ID NO: 58, a VH CDR-H2 comprising the amino acid sequence of SEQ ID NO: 59; and a VH CDR-H3 comprising the amino acid sequence of SEQ ID NO: 60; and (ii) a light chain variable region (VL) that comprises: a VL complementarity determining region one (CDR-L1) comprising the amino acid sequence of SEQ ID NO: 61, a VL CDR-L2 comprising the amino acid sequence of SEQ ID NO: 62; and (c) a VL CDR-L3 comprising the amino acid sequence of SEQ ID NO: 63.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO:58, a CDR-H2 sharing at least 90%, at least 91%, at least 92%, at least 93%, at least 94%, or at least 95% identity with SEQ ID NO: 59, and a CDR-H3 sharing at least 90%, at least 91%, at least 92%, at least 93%, at least 94%, or at least 95% identity with SEQ ID NO: 60; and/or (ii) the following light chain CDR sequences: a CDR-L1 sharing at least 90%, at least 91%, at least 92%, at least 93%, at least 94%, or at least 95% identity with SEQ ID NO: 61, a CDR-L2 sharing at least 90%, at least 91%, at least 92%, at least 93%, at least 94%, or at least 95% identity with SEQ ID NO: 62, and a CDR-L3 sharing at least 90%, at least 91%, at least 92%, at least 93%, at least 94%, or at least 95% identity with SEQ ID NO: 63.

In certain embodiments, no more than 5, no more than 4, no more than 3, no more than 3, no more than 2, or no more than one substitution is made in the sequence of CDR-L1, relative to SEQ ID NO. 61. In certain embodiments, no more than 4, no more than 3, no more than 3, no more than 2, or no more than one substitution is made in the sequence of CDR-L2, relative to SEQ ID NO. 62. In certain embodiments, no more than 5, no more than 4, no more than 3, no more than 3, no more than 2, or no more than one substitution is made in the sequence of CDR-L3, relative to SEQ ID NO. 63. In certain embodiments, no more than 3, no more than 2, or no more than one substitution is made in the sequence of CDR-H1, relative to SEQ ID NO. 58. In certain embodiments, no more than 10, no more than 9, no more than 8, no more than 7, no more than 6, no more than 5, no more than 4, no more than 3, no more than 3, no more than 2, or no more than one substitution is made in the sequence of CDR-H2, relative to SEQ ID NO. 59. In certain embodiments, no more than 5, no more than 4, no more than 3, no more than 3, no more than 2, or no more than one substitution is made in the sequence of CDR-H3, relative to SEQ ID NO. 60. In certain embodiments, the substitution does not change binding affinity ($K_D$) value by more than 3 orders of magnitude, more than 2 orders of magnitude, or 1 order of magnitude, as compared with the $K_D$ of the antibody, or antigen-binding fragment thereof, without the substitution.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 64, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 65. Any combination of these VL and VH sequences is also encompassed by the invention.

In certain embodiments, the antibody or antigen-binding fragment thereof described herein comprises a human immunoglobulin kappa constant domain sequence (e.g., SEQ ID NO:30). In certain embodiments, the antibody or antigen-binding fragment thereof described herein comprises a human immunoglobulin lambda constant domain sequence (e.g., SEQ ID NO:47).

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 46; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 47. Any combination of these CH and CL sequences is also encompassed by the invention.

In certain embodiments, the antibody or antigen-binding fragment thereof described herein comprises an Fc domain. The Fc domain can be derived from IgA (e.g., IgA1 or IgA2), IgG, IgE, or IgG (e.g., IgG1, IgG2, IgG3, or IgG4).

In certain embodiments, the antibody or antigen-binding fragment thereof described herein comprises a human immunoglobulin heavy constant gamma 4 (IgG4) sequence (e.g., SEQ ID NO: 46). In certain embodiments, the antibody or antigen-binding fragment thereof described herein comprises a human immunoglobulin heavy constant gamma 1 (IgG1) sequence (e.g., SEQ ID NO: 68). In certain embodiments, the antibody or antigen-binding fragment thereof described herein comprises a human immunoglobulin heavy constant gamma 2 (IgG2) sequence (e.g., SEQ ID NO: 69). In certain embodiments, the antibody or antigen-binding fragment thereof described herein comprises a human immunoglobulin heavy constant gamma 3 (IgG3) sequence (e.g., SEQ ID NO: 70).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 66, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 67. Any combination of these heavy chain and light chain sequences is also encompassed by the invention.

Sometimes, the C-terminal lysine of an antibody heavy chain undergoes cleavage by carboxypeptidase during expression. Accordingly, in some aspects, the anti-LILRB1 antibody comprises a heavy chain constant region lacking the C-terminal Lys. A heavy chain constant region lacking the C-terminal Lys advantageously prevents carboxypeptidase to act on the heavy chain of the anti-LILRB1 antibody.

In certain embodiments, the anti-LILRB1 antibody, antigen binding antibody fragment thereof, or anti-LILRB1 antibody protein product comprises one or more amino acid modifications, relative to the naturally-occurring counterpart, in order to improve half-life/stability or to render the antibody more suitable for expression/manufacturability. In exemplary embodiments, the anti-LILRB1 antibody is designed to prevent or reduce interaction between the anti- LILRB1 antibody and Fc receptors. In exemplary instances, the anti-LILRB1 antibody is a Stable Effector Functionless (SEFL) antibody comprising a constant region that lacks the ability to interact with Fcγ receptors. SEFL antibodies are known in the art. See, e.g., Liu et al., J Biol Chem 292: 1876-1883 (2016); and Jacobsen et al., J. Biol. Chem. 292: 1865-1875 (2017). In exemplary aspects, the SEFL antibody comprises one or more of the following mutations, numbered according to the EU system: L242C, A287C, R292C, N297G, V302C, L306C, and/or K334C. In exemplary aspects, the SEFL antibody comprises N297G. In exemplary aspects, the SEFL antibody comprises A287C, N297G, and L306C. In other exemplary aspects, the SEFL antibody comprises R292C, N297G, and V302C (i.e., SEFL2-2).

In certain embodiments, the anti-LILRB1 antibody, antigen binding antibody fragment thereof, competes for binding to LILRB1 with any antibody or antigen-binding fragment thereof described above. Exemplary antibody competition assay is described in detail in Example 6. In general, antigen (such as LILRB1) is typically bound by one reference antibody and probed by another. If the reference antibody prevents the binding of the probe antibody, then the antibodies are said to be competing with each other.

In certain embodiments, the antibody, or antigen-binding fragment thereof, binds the D3 domain of LILRB1, wherein said D3 domain comprises residues 222-312 of SEQ ID NO: 3 (or SEQ ID NO:6).

In certain embodiments, the antibody, or antigen-binding fragment thereof, binds the D4 domain of LILRB1, wherein said D4 domain comprises residues 313-409 of SEQ ID NO: 3 (or SEQ ID NO: 6).

Additional antibodies, or antigen-binding fragment thereof, of the invention can be obtained using LILRB1, LILRB2, or HLA-G (or antigenic fragment thereof) as an antigen. Exemplary sequences of human LILRB1, LILRB2, and HLA-G are provided herein as SEQ ID Nos. 3-18. Using these exemplary sequences as antigens, antibodies (or antigen-binding fragments thereof) of the invention can be obtained using art-known methods. For example, monoclonal antibodies may be made by the hybridoma method, or may be made by recombinant DNA methods. The antibodies may also be isolated from phage antibody libraries.

In certain embodiments, the antibody, or antigen-binding fragment thereof, of the invention binds to any one of SEQ ID NOs:3-7, or an antigenic fragment of any one of SEQ ID NOs:3-7. In certain embodiments, the antibody, or antigen-binding fragment thereof, of the invention binds to an amino acid sequence that is at least 70%, at least 75%, at least 80%, at least 85%, at least 90%, at least 95%, at least 97%, or at least 99% identical to any one of SEQ ID NOs:3-7, or an antigenic fragment of any one of SEQ ID NOs:3-7.

In certain embodiments, the antibody, or antigen-binding fragment thereof, of the invention binds to any one of SEQ ID NOs:8-11, or an antigenic fragment of any one of SEQ ID NOs:8-11. In certain embodiments, the antibody, or antigen-binding fragment thereof, of the invention binds to an amino acid sequence that is at least 70%, at least 75%, at least 80%, at least 85%, at least 90%, at least 95%, at least 97%, or at least 99% identical to any one of SEQ ID NOs:8-11, or an antigenic fragment of any one of SEQ ID NOs:8-11.

In certain embodiments, the antibody, or antigen-binding fragment thereof, of the invention binds to any one of SEQ ID NOs:12-18, or an antigenic fragment of any one of SEQ ID NOs:12-18. In certain embodiments, the antibody, or antigen-binding fragment thereof, of the invention binds to an amino acid sequence that is at least 70%, at least 75%, at least 80%, at least 85%, at least 90%, at least 95%, at least 97%, or at least 99% identical to any one of SEQ ID NOs:12-18, or an antigenic fragment of any one of SEQ ID NOs:12-18. The antibody, or antigen-binding fragment thereof, can bind to membrane-bound isoforms (e.g., HLA-G1, HLA-G2, HLA-G3, HLA-G4), soluble isoforms (e.g., HLA-G5, HLA-G6, HLA-G7), and soluble forms generated by proteolytic cleavage of membrane-bound isoforms (e.g. sHLA-G1).

Other LILRB1/2 pathway inhibitors that are useful for the invention include, for example, an immunoadhesin that specifically binds to LILRB1, LILRB2, or HLA-G, a fusion protein containing the extracellular portion of LILRB1, LILRB2, or HLA-G fused to a constant region (such as an Fc region of an immunoglobulin molecule).

Antisense RNA, or small interfering RNA (siRNA) may also be used as LILRB1/2 pathway inhibitors. Various art-known methods can be used to analyze the sequence of LILRB1, LILRB2, and HLA-G (such as SEQ ID Nos. 3-18) to obtain antisense RNA or siRNA that inhibits the expression of LILRB1, LILRB2, and/or HLA-G. siRNA design algorithms has been described above.

In certain embodiments, the LILRB1/2 pathway inhibitor is a short interfering RNA (siRNA) that reduces the expression level of HLA-G, as compared to a control. Exemplary lymphocytes mediated signaling through LILRB1/2, so to render a dysfunctional T-cell less dysfunctional (e.g., enhancing effector responses to antigen recognition).

3.3. Methods of Making Antibodies

Suitable methods of making antibodies and antigen-binding fragments thereof are known in the art. For instance, standard hybridoma methods for producing antibodies are described in, e.g., Harlow and Lane (eds.), Antibodies: A Laboratory Manual, CSH Press (1988), and CA. Janeway et al. (eds.), Immunobiology, 5th Ed., Garland Publishing, New York, NY (2001)). An exemplary method of preparing anti-PD-1 monoclonal antibodies or the present disclosure is provided herein in EXAMPLES.

Depending on the host species, various adjuvants can be used to increase the immunological response leading to greater antibody production by the host. Such adjuvants include but are not limited to Freunds, mineral gels such as aluminum hydroxide, and surface active substances such as lysolecithin, pluronic polyols, polyanions, peptides, oil emulsions, keyhole limpet hemocyanin, and dinitrophenol. BOG (bacilli Calmette-Guerin) and *Corynebacterium parvum* are potentially useful human adjuvants.

Other methods of antibody production are summarized in Table 1.

TABLE 1

| Technique | Exemplary references |
| --- | --- |
| EBV-hybridoma methods and Bacteriophage vector expression systems methods of producing antibodies in non-human animals inducing in vivo production in the lymphocyte population or by screening recombinant immunoglobulin libraries or panels of highly specific binding reagents | Haskard and Archer, J. Immunol. Methods, 74(2), 361-67 (1984), Roder et al., Methods Enzymol., 121, 140-67 (1986), and Huse et al., Science, 246, 1275-81 (1989)). U.S. Pat. Nos. 5,545,806, 5,569,825, and 5,714,352, and U.S. patent application Publication No. 2002/0197266 Orlandi et al (Proc Natl Acad Sci 86: 3833-3837; 1989), and Winter G and Milstein C (Nature 349: 293-299, 1991). |
| methods of producing recombinant proteins | Protein production and purification" Nat Methods 5(2): 135-146 (2008). |
| Phage display | Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; and U.S. Pat. No. 6,225,447 |
| Antibodies can be produced by transgenic mice | U.S. Pat. Nos. 5,545,806 and 5,569,825, and Janeway et al., supra. | siRNA that reduces the expression level of HLA-G can be found, e.g., in WO 2012/098234. In an exemplary embodiment, the siRNA comprises SEQ ID NO: 31.

A variety of controls may be used. HLA-G expression level from a non-cancer cell from the same patient, or from a cell from a healthy individual may be used as a control. Alternatively, the control may be expression level of HLA-G from the individual being treated at a time prior to treatment or at a time period earlier during the course of treatment. Still other controls may include a pre-determined expression level (e.g., expression data from public database, or from scientific literature).

In some embodiments, the LILRB1/2 pathway inhibitor described herein reduces the negative co-stimulatory signal mediated by or through cell surface proteins expressed on T Methods of testing antibodies, or antigen-binding fragments thereof, for the ability to bind to intended target (e.g., PD-1, PD-L1, LILRB1, LILRB2, or HLA-G) regardless of how the antibodies are produced are known in the art and include any antibody-antigen binding assay, such as, for example, radioimmunoassay (RIA), ELISA, Western blot, immunoprecipitation, SPR, and competitive inhibition assays (see, e.g., Janeway et al., infra, and U.S. Patent Application Publication No. 2002/0197266, and the above section relating to competition assays). Other binding assays, e.g., competitive binding assays or competition assays, which test the ability of an antibody to compete with a second antibody for binding to an antigen, or to an epitope thereof, are known in the art and can be used to test the ability of an antibody to bind to PD-1, PD-L1, LILRB1, LILRB2, or HLA-G. See, e.g., U.S. Patent Application Publication No. US20140178905, Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art, and include, for example, surface plasmon resonance (SPR). SPR can be used to determine the binding constants of the antibody and second antibody and the two binding constants can be compared.

In certain embodiments, the affinity of the antibody, or antigen-binding fragment thereof, to an intended antigen may be described in terms of $K_D$. In exemplary aspects, the $K_D$ of the antibody provided herein is about $10^{-1}$ M or less, about $10^{-2}$ M or less, about $10^{-3}$ M or less, about $10^{-4}$ M or less, about $10^{-5}$ M or less, about $10^{-6}$ M or less, about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less, from about $10^{-5}$ M to about $10^{-15}$ M, from about $10^{-6}$ M to about $10^{-15}$ M, from about $10^{-7}$ M to about $10^{-15}$ M, from about $10^{-8}$ M to about $10^{-15}$ M, from about $10^{-9}$ M to about $10^{-15}$ M, from about $10^{-10}$ M to about $10^{-15}$ M, from about $10^{-5}$ M to about $10^{-14}$ M, from about $10^{-6}$ M to about $10^{-14}$ M, from about $10^{-7}$ M to about $10^{-14}$ M, from about $10^{-8}$ M to about $10^{-14}$ M, from about $10^{-9}$ M to about $10^{-14}$ M, from about $10^{-10}$ M to about $10^{-14}$ M, from about $10^{-5}$ M to about $10^{-13}$ M, from about $10^{-6}$ M to about $10^{-13}$ M, from about $10^{-7}$ M to about $10^{-13}$ M, from about $10^{-8}$ M to about $10^{-13}$ M, from about $10^{-9}$ M to about $10^{-13}$ M, or from about $10^{-10}$ M to about $10^{-13}$ M.

In certain embodiments, the $K_D$ of the antibody, or antigen-binding fragment thereof, provided herein is micromolar, nanomolar, picomolar or femtomolar. In exemplary aspects, the $K_D$ of the antibody provided herein is within a range of about $10^{-4}$ to $10^{-6}$ M, or $10^{-7}$ to $10^{-9}$ M, or $10^{-10}$ to $10^{-12}$ M, $10^{-13}$ to $10^{-15}$ M. In exemplary embodiments, the antibody, or antigen-binding fragment thereof, has a $K_D$ of less than 100 pM, optionally, about 1 pM to about 50 pM, such as about 1 pM to about 20 pM, or less than about 10 pM.

The value of $K_D$ can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein.

One exemplary method for measuring binding affinity ($K_D$) value is surface plasmon resonance (SPR), typically using a biosensor system such as a BIACORE® system. SPR refers to an optical phenomenon that allows for the analysis of real-time biospecific interactions by detection of alterations in protein concentrations within a biosensor matrix, for example using the BIACORE® system. BIAcore kinetic analysis comprises analyzing the binding and dissociation of an antigen from a chip with an immobilized molecule (e.g., a molecule comprising an antigen-binding domain), on their surface; or the dissociation of an antibody, or antigen-binding fragment thereof, from a chip with an immobilized antigen.

In certain embodiments, the affinity of an antibody is measured according to the conditions provided in Example 6.

3.4. Methods of Treatment

The combination therapy described herein can be used to increase IFN-γ expression level in a subject that has cancer, and/or to increase CD8+ T-cell mediated cytotoxicity in a subject that has cancer.

It has been reported that IFN-γ related mRNA profile can predict clinical response to PD-1 blockade (Ayers et al., J Clin Invest. 2017; 127(8):2930-2940). Host immune system is capable of recognizing and eliminating dysplastic and neoplastic cells. Certain factors, such as exposure to ultraviolet radiation, smoking, and chronic viral infection, can damage critical genes involved in DNA replication and repair, resulting in abnormal cellular growth. In response, an orchestrated innate and adaptive antitumor immune response is initiated that may lead to the production of IFN-γ. IFN-γ is a key cytokine produced by activated T cells, as well as natural killer (NK) and NK T cells, in the tumor microenvironment, and it plays an important role in coordinating this process. However, the same IFN-γ signaling processes can ultimately induce feedback inhibition that compromises antitumor immunity. As part of this feedback loop, IFN-γ signaling enables the PD-1 signaling axis to become activated through direct upregulation of the ligands PD-L1 and PD-L2 in tumor, immune infiltrate, and stromal cells, which interact with PD-1 on tumor-infiltrating T cells to downregulate the cytotoxic response. In addition, IFN-γ can upregulate expression of other key immune suppressive molecules such as IDO1 within the tumor microenvironment. Tumor adaptation takes advantage of this delicate balance of positive and negative immune signaling factors, allowing the cancer to survive and progress.

Studies have also shown that it IFN-γ can enhance anti-tumor and antiviral effects of CD8+ T cells. The CD8+ T cells are able to produce IFNγ, which enhances their ability to migrate to the site of antigen-presenting cells. Conversely, deprivation of either autocrine or paracrine IFNγ, or blockade of IFNγ signaling to CTL markedly reduced their cytotoxic function, their kinematics, and effector cell survival. The need for local IFNγ to enable cytotoxic CD8+ T-cell function is significant for cancer treatment.

The treatment method described herein can be used to treat a variety of cancers, especially cancer patients who are poor responders to the treatment using an PD-1/PD-L1 pathway inhibitor. As shown in the examples, the combination is particularly effective in patients who responded to anti-PD-1 treatment poorly. For certain patients (see, e.g., FIG. 7, Pair #1), mono-therapy using either anti-PD-1, or anti-LILRB1 failed to improve CD8+ T cell mediated cytotoxicity as compared to control. However, when anti-PD-1 and anti-LILRB1 are combined, the increase in CD8+ T cell cytotoxicity was more than doubled.

Accordingly, provided herein are methods of increasing T cell activity, in particular CD8+ T-cell mediated cytotoxicity in a subject. Such increase in T cell activity includes, e.g., increasing T cell survival and effector function, restricting terminal differentiation and loss of replicative potential, promoting T cell longevity, and enhancing cytotoxicity against target (e.g., cancer) cells. In certain embodiments, the T cell activity or immune response is directed against a cancer cell or cancer tissue or a tumor cell or tumor. In certain embodiments, the immune response is a humoral immune response. In certain embodiments, the immune response is an innate immune response. In certain embodiments, the immune response which is enhanced is a T-cell mediated immune response.

In certain embodiments, the cancer is a solid tumor. In some embodiments, the cancer is brain cancer, bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, colorectal cancer, or gastric cancer.

Additional cancers can be treated include acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, and bronchioloalveolar carcinoma.

In certain embodiments, the cancer is non-small cell lung cancer (NSCLC), head and neck cancer, renal cancer, triple negative breast cancer, or gastric cancer. In certain embodiments, the cancer is non-small cell lung cancer (NSCLC), small cell lung cancer (SCLC), head and neck cancer, renal cancer, breast cancer, melanoma, ovarian cancer, liver cancer, pancreatic cancer, colon cancer, prostate cancer, gastric cancer, lymphoma or leukemia.

In certain embodiments, the cancer is brain cancer.

In certain embodiments, the cancer is brain cancer, bladder cancer, breast cancer, clear cell kidney cancer, cervical cancer, colon cancer, rectal cancer, endometrial cancer, gastric cancer, head/neck squamous cell carcinoma, lip cancer, oral cancer, liver cancer, lung squamous cell carcinoma, melanoma, mesothelioma, non-small-cell lung cancer (NSCLC), non-melanoma skin cancer, ovarian cancer, pancreatic cancer, prostate cancer, renal cell carcinoma, sarcoma, small-cell lung cancer (SCLC), Squamous Cell Carcinoma of the Head and Neck (SCCHN), triple negative breast cancer, or thyroid cancer.

In certain embodiments, the cancer is adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumor, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, or Wilms tumor.

In certain embodiments, the cancer is acute lymphoblastic leukemia (ALL), acute myeloid leukemia (AML), chronic lymphocytic leukemia (CLL), or chronic myeloid leukemia (CML).

In certain embodiments, the cancer is diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), or small lymphocytic lymphoma (SLL).

In certain embodiments, the cancer tests positive for the expression of PD-L1, PD-L2, or combination thereof. In certain embodiments, the cancer has increased PD-L1 and/or PD-L2 expression, as compared to a normal cell. In certain embodiments, the individual is a human and the cancer is a solid tumor that tests positive for human PD-L1 and/or PD-L2.

In certain embodiments, the cancer tests positive for the expression of HLA-G. In certain embodiments, the cancer has increased HLA-G expression, as compared to a normal cell. In certain embodiments, the individual is a human and the cancer is a solid tumor that tests positive for human HLA-G.

CD8+ T-cell mediated cytotoxicity, as well as the likely outcome of treatment, can be assessed by art-known methods (e.g., by measuring IFN-$\gamma$ levels in the subject). Measurement of IFN-$\gamma$ levels in a subject can be carried out in any suitable tissue or bodily fluid sample from the subject. The measured CD8+ T-cell mediated cytotoxicity (such as level of IFN-$\gamma$) can then be compared to a control or a reference. The control can be CD8+ T-cell mediated cytotoxicity level (such as level of IFN-$\gamma$) from a non-cancer cell from the same patient, or from a cell from a healthy individual. Alternatively, the control may be the level of CD8+ T-cell mediated cytotoxicity (such as IFN-$\gamma$ expression level) from the individual being treated at a time prior to treatment or at a time period earlier during the course of treatment. Still other controls may include a pre-determined level (e.g., T cell cytotoxicity data such as IFN-$\gamma$ expression data from public database, or from scientific literature). The control can be corrected for demographic variation and the like, if necessary, using methods that are well known in the art.

The levels of IFN-$\gamma$ expression, may be measured at the protein or nucleic acid level. For example, measurement of protein expression at the protein level can be performed by immunoassays such as ELISA (direct and sandwich), immunohistochemistry, Western blot, radioimmunoassay, flow cytometry and neutralization, although the skilled artisan will be aware of other methods that are well known and available. Suitable immunoassay methods are described, for example, in U.S. Pat. No. 4,666,865. Suitable reagents and kits to perform these tests are available from R&D Systems Inc., Minnesota. Suitable reagents and kits available from R&D Systems Inc., to measure human IFN-$\gamma$ include anti-human IFN-$\gamma$ antibody (Cat. No. AF-285-NA); biotinylated anti-human IFN-$\gamma$ antibody (Cat. No. BAF285); DuoSet® ELISA for human IFN-$\gamma$ (Cat. No. DY285); human IFN-$\gamma$ development module (Cat. No. SEL285); ELISpot for human IFN-γ (Cat. No. EL285); Carboxyfluorescein conjugated IFN-γ monoclonal antibody (Cat. No. IC285F); Fluorokine MAP human IFN-γ kit (Cat. No. LU285); Monoclonal anti-human IFN-γ antibody Cat. No. MAB285); Phycoerythrin-conjugated monoclonal IFN-γ antibody (Cat. No. IC285P); Quantkine human IFN-γ ELISA kit (Cat. No. DIF50); anti-human IFN-γ polyclonal antibody (Cat. No. AB 250 NA) and affinity purified anti-human IFN-γ polyclonal antibody (Cat. No. AF 250 NA). A radioimmunoassay kit for human IFN-γ is available from Celltech, Berkshire, England. Alternatively, mass spectrometry, chromatography (including high pressure liquid chromatography), gel electrophoresis and biological activity assays can be used to measure IFN-γ levels and activity in human samples.

Measurement of protein expression at the nucleic acid level can be achieved by quantitative RT-PCR methods, PCR-ELISA, and in situ hybridization techniques that are well known the art. Suitable reagents and kits available from R&D Systems Inc., to measure human IFN-γ mRNA expression include human IFN-gamma Quantikine mRNA kit (Cat. No. KRNIF0-0); human IFN-gamma primer pair (Cat. No. RDP-14-025); Quantikine mRNA Probes and Calibrator Kit for human IFN-γ (Cat. No. RNIF0-036). Alternatively, microarray-based methods and the like may be used. Such microarray methods are commercially available, for example from Affymetrix (Sunnyvale, Calif.).

The biological sample can be a body fluid, such as plasma, serum, urine, cerebral spinal fluid, and sputum. The biological sample can also be tissue samples, such as biopsy.

Additional methods of measuring T cell activity and immune responses are known in the art. T cell activity can be measured by, for example, a cytotoxicity assay, such as those described in Fu et al., PLoS ONE 5(7): e11867 (2010). Other T cell activity assays are described in Bercovici et al., Clin Diagn Lab Immunol. 7(6): 859-864 (2000). Methods of measuring immune responses are described in e.g., Macatangay et al., Clin Vaccine Immunol 17(9): 1452-1459 (2010), and Clay et al., Clin Cancer Res.7(5):1127-35 (2001).

4. Pharmaceutical Compositions and Administration

In another aspect, the invention also provides a pharmaceutical composition comprising the PD-1 pathway inhibitor and LILRB1/2 pathway inhibitor described herein.

The PD-1 pathway inhibitor and LILRB1/2 pathway inhibitor described herein can be prepared as two separate compositions. The two compositions can be administered separately, or be mixed together at bedside right before administration.

Alternatively, the PD-1 pathway inhibitor and LILRB1/2 pathway inhibitor described herein can be prepared as a single, pre-mixed composition.

In other embodiments, the two inhibitors can be conjugated into a single molecule, then be formulated into a single composition. For example, the composition can comprise a bi-specific antibody, with one arm binds PD-1 or PD-L1, and the other arm binds LILRB1, LILRB2, or HLA-G.

The pharmaceutical composition may additionally comprise a pharmaceutically acceptable carrier, diluents, or excipient. Standard pharmaceutical carriers include a phosphate buffered saline solution, water, emulsions such as an oil/water or water/oil emulsion, and various types of wetting agents.

The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In exemplary embodiments, the pH of the pharmaceutical composition is between 5.5 and 7.5.

The PD-1 pathway inhibitor and LILRB1/2 pathway inhibitor described herein can be administered to the subject via any suitable route of administration, such as parenteral, nasal, oral, pulmonary, topical, vaginal, or rectal administration. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. For additional details, see *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

The dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the cytotoxicity of the active agent or the extent of tumor regression achieved with the active agent in a mouse xenograft model. Methods of measuring cytotoxicity of the fusion proteins and methods of assaying tumor regression are known in the art.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the present disclosure, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day. Dosage units may be also expressed in rag/m$^2$, which refer to the quantity in milligrams per square meter of body surface area.

Each therapeutic agent in the combination therapy described herein may be administered simultaneously (e.g., in the same medicament or at the same time), concurrently (i.e., in separate medicaments administered one right after the other in any order or sequentially in any order. Sequential administration may be useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In certain embodiments, the PD-1 pathway inhibitor and the LILRB1/2 pathway inhibitor are combined or co-formulated in a single dosage form. In certain embodiments, the PD-1 pathway inhibitor and the LILRB1/2 pathway inhibitor are administered separately. Although the simultaneous administration of the PD-1 pathway inhibitor and the LILRB1/2 pathway inhibitor may be maintained throughout a period of treatment, anti-cancer activity may also be achieved by subsequent administration of one compound in isolation (for example, the PD-1 pathway inhibitor without the LILRB1/2 pathway inhibitor following initial combination treatment, or alternatively, the LILRB1/2 pathway inhibitor without the PD-1 pathway inhibitor following initial combination treatment). In some embodiments, the PD-1 pathway inhibitor is administered before administration of the LILRB1/1 pathway inhibitor, while in other embodiments, the PD-1 pathway inhibitor is administered after administration of the LILRB1/2 pathway inhibitor. In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

The combination therapy of the invention may be used prior to or following surgery to remove a tumor and may be used prior to, during or after radiation therapy. The combination therapy of the invention may be used to treat a tumor that is large enough to be found by palpation or by imaging techniques well known in the art, such as MRI, ultrasound, or CAT scan. In some embodiments, the combination therapy of the invention is used to treat an advanced stage tumor having dimensions of at least about 200 mm$^3$, 300 mm$^3$, 400 mm$^3$, 500 mm$^3$, 750 mm$^3$, or up to 1000 mm$^3$.

EXAMPLES

Introduction

T cells, especially antigen specific cytotoxic T cells, can detect and eliminate cancer cells through the recognition of tumor associated antigens such as neo-antigens. Neoplastic cells, however, evade the immune recognition through various mechanisms. For example, tumor infiltrating T cells often fail to eliminate cancer due to an immunosuppressive tumor microenvironment that promotes a dysfunctional T cell state, often termed "exhaustion", characterized by the expression of multiple inhibitory receptors, such as PD-1, TIM3, and CTLA-4. Strategies aimed at boosting immune cell recognition of cancer and T cell cytotoxicity against tumor cells have long been used to treat cancers. For example, cytokines such as IFN-α and IL-2, which promote antigen presentation and T cell activity, respectively, have been used to treat melanoma and other cancers for many years. Their anti-tumor effects, however, have been limited by severe, dose-limiting side effects. In recent years, checkpoint inhibitors (including antibodies targeting CTLA-4 and PD-1 that are expressed on exhausted T cells and regulatory T cells) have been able to enhance the anti-tumor effector functions of T cells and have shown dramatic therapeutic benefit in various cancer types, although only in a subset of patients.

In human peripheral blood, there are several CD8+ T cell subsets, in addition to naïve and memory CD8+ cells, CD45RA and CCR7 markers also define $T_{EMRA}$ subset (CD45RA+CCR7−). These cells are antigen-experienced effector cells with high cytotoxicity, high sensitivity to apoptosis, low IL-2 production, and low proliferative capability. In addition, these cells represent a significant CD8+ T cell population in elder individual and cancer patients. Several other markers such as CD27, CD28, and CD57 are also used to define the heterogeneity of $T_{EMRA}$ cells. $T_{EMRA}$ cells are found to express many NK-like receptors, such as KLRG-1 and LILRB1.

Exhausted CD8+ T cells were reported to dominantly infiltrate various solid tumors. These cells highly express various inhibitory co-receptors such as PD-1, TIM3, and LAG3. However, it is unclear whether $T_{EMRA}$ cells are also present in solid tumors, and whether PD-1 pathway plays a role in regulating their activities.

LILRB1 belongs to leukocyte Ig-like receptor subfamily B that is expressed in various types of immune cells to suppress their activation. LILRB1 is the only member in LILR family that is expressed on subsets of CD8+ T cells, as well as some NK cells and B cells. It contains 4 Ig-like domains extracellularly that mediates its interaction with ligands (i.e., non-classical class I molecule HLA-G). LILRB1 has 4 ITIM motifs in its intracellular domain that recruit SHP1 and SHP2 upon ligation to inhibit ITAM signaling.

In this study, we demonstrated that LILRB1 was a good marker to identify effector CD8+ cells and it exerted a negative regulatory function during BiTE® molecule-induced tumor killing. More importantly, we discovered that CD8+ subset expressing of LILRB1 and CD8+ subset expressing PD-1 are non-overlapping—each marker is uniquely associated with different CD8+ T cell subsets. Blocking both pathways could synergistically enhance CD8+ T cell function.

Example 1. Lilrb1 Inhibits Cd8+ Effector T Cell Activation and Function in a Tdcc Assay In order to understand which human CD8+ subset most efficiently mediated BiTE® molecule-induced TDCC, we isolated human CD8$^+$ naive (T$_N$), effector memory (T$_{EM}$), and effector or effector memory RA (T$_{EMRA}$) subsets based on expression of surface markers CD45RA and CCR7 from peripheral blood. The cytolytic activity of isolated CD8+ T cell subsets was determined by utilizing a MART-1 BiTE® molecule-mediated SK-MEL-2 tumor cell killing assay. We discovered that CD45RA$^+$CCR7$^-$ T$_{EMRA}$ cells were the most effective subset in killing the target cancer cells induced by BiTE® molecule (EC50=25.51 pM), followed by CD45RA$^-$CCR7$^-$ T$_{EM}$ cells (EC50=58.11 pM) and CD45RA$^-$CCR7$^-$ T$_N$ cells (EC50=7948 nM). T$_{EMRA}$ cells also had the highest maximum percentage of tumor cell lysis in the assay.

These data suggested that enhancing the effector function of T$_{EMRA}$ could further enhance BiTE® molecule-mediated tumor killing. To identify regulatory pathways that modulating CTL activity of these CD8+ subsets, we compared their gene transcriptional profiles. As expected, memory CD8+ T cells highly expressed various genes, including PRF1, GZMB, and CX3CR1, which were associated CD8+ T cell effector function. In addition, we also identified the co-inhibitory molecule LILRB1 as being preferentially expressed in T$_{EMRA}$ and T$_{EM}$ CD8+ T cell subsets (FIG. 1D). FACS analysis confirmed majority of T$_{EMRA}$ cells highly expressed LILRB1, and a minor T$_{EM}$ CD8+ subsets also had detectable level of LILRB1 expression (FIGS. 1A-1C).

Figure 2A:
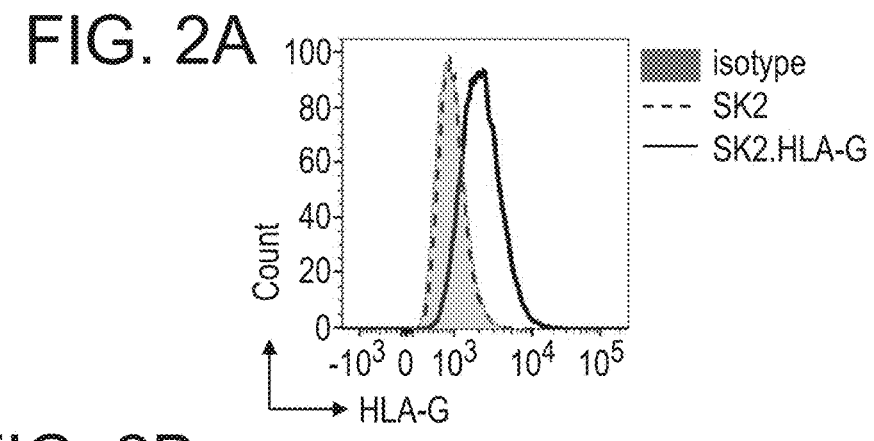
FIGS. 2A-2D show that LILRB1 inhibits CD8+ T cell activation and cytolytic effector function.
Figure 2B:
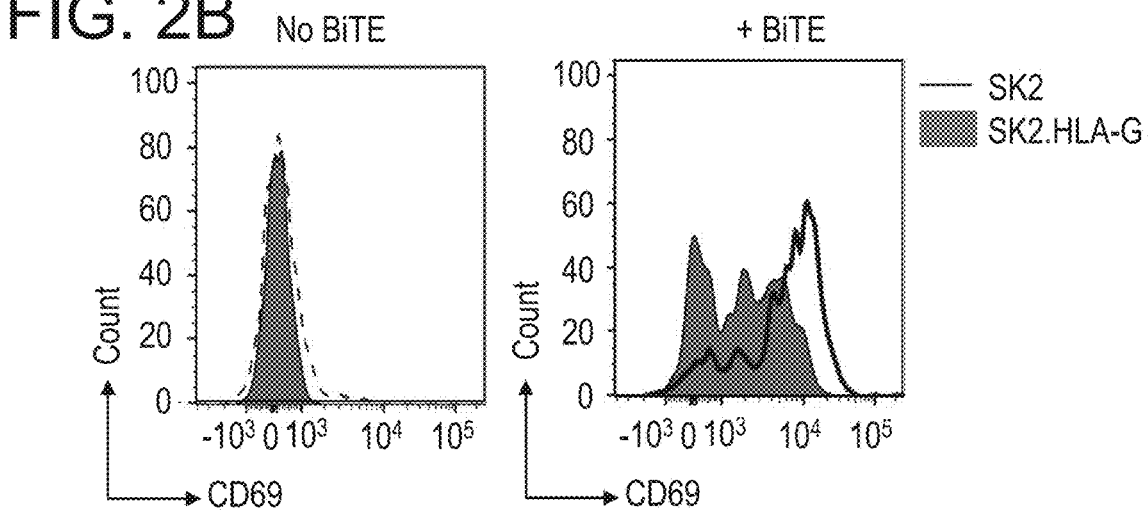
Figure 2C:
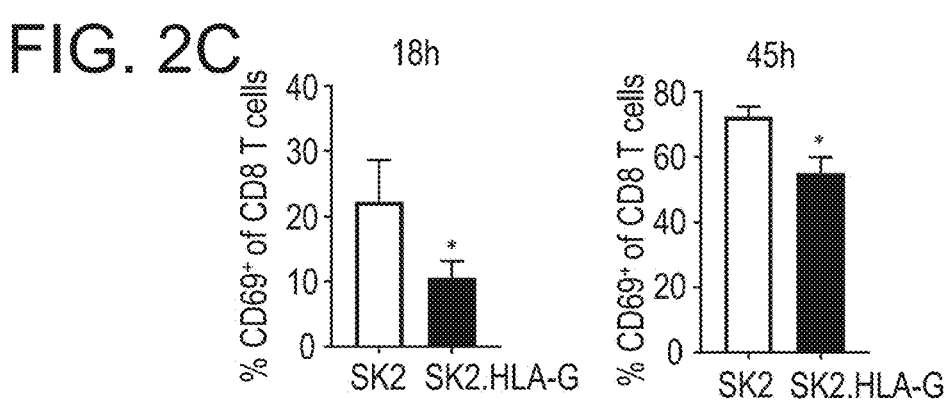
Figure 2D:
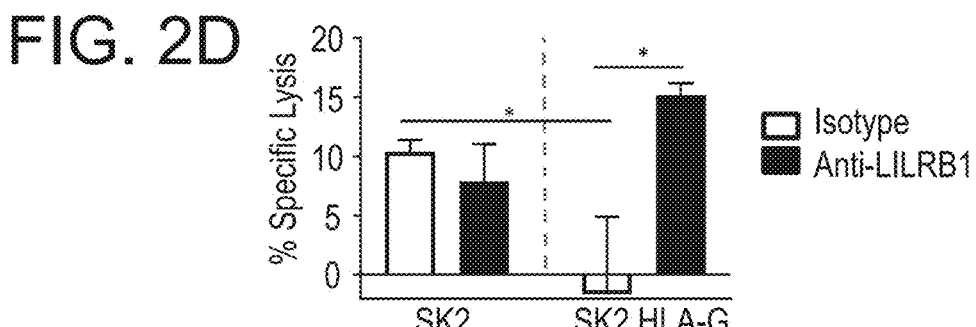

In order to elucidate if LILRB1 regulates the function of CD8+ effector cells in our BiTE® molecule system, we performed CD8+ T cell killing assays utilizing a MART-1 BiTE® molecule. We engineered SK-MEL-2 target cells to express HLA-G, the ligand for LILRB1 (FIG. 2A). T$_{EMRA}$ CD8+ T cells were enriched from healthy donor PBMC by flow sorting and were co-cultured with parental SK-MEL-2 target cells (SK2) or HLA-G-overexpressing SK-MEL-2 cells (SK2.HLA-G) in the presence of anti-LILRB1 blocking or control antibodies. Effector CD8+ function was stimulated by a suboptimal concentration of MART-1 BiTE® molecule, and measured as specific target cell lysis. Our data showed that HLA-G-expression on target cells dramatically reduced BiTE® molecule-induced CD8+ T cell cytolytic activity against tumor cells (FIG. 2D). LILRB1 blockade significantly enhanced CTL function to kill HLA-G-expressing tumor cells in this assay (FIG. 2D). Presence of HLA-G on tumor cells also significantly inhibited BiTE® molecule-mediated upregulation of CD69 on effector CD8+ T cells (FIGS. 2B and 2C). In summary, these data support the conclusion that LILRB1 functions as a negative regulator of CD8+ effector T cell function and that blocking LILRB1 can enhance BiTE® molecule-mediated tumor lysis by effector CD8+ cells.

Materials and Methods

Primary human T cell isolation. Human PBMCs from healthy volunteers were obtained after informed consent and authorized by Amgen Research Blood Donor Program. Peripheral blood mononuclear cells (PBMCs) were isolated by density gravity centrifugation (Ficoll-Paque™ PRE-MIUM; GE Healthcare). Isolated cells were incubated with monoclonal antibodies (CD3-APC (Sk7, eBioscience), CD4-BV605 (OKT4, Biolegend), CD8-AF700 (RPA-T8, Biolegend), CCR7-BV421 (G043H7, Biolegend), CD45RA-APC-Cy7 (H1100, Biolegend)) for 30 min at 4° C. with 7AAD for live dead staining (BD Biosciences) followed by thorough washing. Cell subsets were then isolated from stained PBMC by cell sorting with BD FACSAria™ cytometer based on surface marker expression, such that CD45RA$^+$CCR7$^+$ cells as T$_N$, CD45RA$^-$CCR7$^+$ cells as TCM, CD45RA$^-$CCR7$^-$ cells as T$_{EM}$, and CD45RA$^+$CCR7$^-$ cells as T$_{EMRA}$, in CD4+ (gated as CD3$^+$CD4$^+$CD8$^-$) and CD8+ (gated as CD3$^+$CD4$^-$CD8$^+$) cells.

Flow cytometry. Isolated cells were stained with indicated monoclonal antibodies (CD3-APC (Sk7, eBioscience), CD4-BV605 (OKT4, Biolegend), CD8-AF700 (RPA-T8, Biolegend), CCR7-BV421 (G043H7, Biolegend), CD45RA-APC-Cy7 (H1100, Biolegend), LILRB1-PE (GHI/75, Biolegend), and PD-1-BV650 (EH12.1, BD Bioscience), with 7AAD for live dead staining (BD Biosciences). Cells were incubated with appropriate antibodies for 30 min at 4° C. followed by washing with FACS buffer (BD Biosciences). Sample processing was performed on a LSR II (BD Biosciences) and with FlowJo™ 10 software (Tree Star).

RNA Sequencing. Total RNAs were isolated from sorted T cell subsets (Qiagen). PolyA tailed mRNAs were isolated with Oligo-dT beads and RNA library was prepared following standard protocol.

Target Cell lines. Parental SK-MEL-2 (SK2) were maintained EMEM medium (ATCC) with 10% FBS and 1% penicillin/streptomycin at 37° C. Cells with stable expression of HLA-G were established by retroviral transduction. The HLA-G. β2 microglobulin cDNA was inserted into retrovirus vector pLHCX and was co-transfected with Lipofectamine 3000 (Thermo Fisher Scientific) into GP2-293 packaging cells with pVSV-G. Supernatant were collected 48 hours after transfection and filtered. Then, SK2 cells were transduced with a mixture of viral supernatant with polybrene at 5 μg/ml (EMD Millipore). After spin transduction for 1.5 h at 1200g, 32° C., fresh media was added. HLA-G expression was confirmed by flow cytometry using LSR II (BD Biosciences).

Cytotoxicity assay. Isolated CD8+ T subsets (T$_N$, T$_{EM}$, and T$_{EMRA}$) as effector cells were co-cultured with target HLA-G expressing SK2 or SK2 tumor lines in the presence of different concentrations of the MART1 BiTE® molecule (Amgen) in black 96-well flat bottom plates with transparent bottoms (Nunc). The effector cell to target cell ratio was 4:1 (L$_{exp}$). Co-culture of effector cells and target cells without BiTE® molecule as control (L$_{max}$). For blocking assay, 20 μg/ml of anti-LILRB1 (GHI/75, Biolegend) or isotype control antibody (Biolegend) were added in the assay. Cells were cultured in RPMI-1640 supplemented with 10% heat-inactivated FBS, 100 U/mL penicillin and streptomycin, 2-Mercaptoethanol (all from Gibco) at 37° C. After 45 h, T cells were removed by washing with warm media and stained for CD69 (FN50, Biolegend) followed by flow cytometry using LSR II (BD Biosciences). Samples were analyzed with FlowJo 10 software (Tree Star). Target cell were washed and cell viability was determined by CellTiter-Glo® (Promega). Luminescence was measured with EnVision® 2104 multilable reader (PerkinElmer). Percentage of specific target cell lysis was calculated by the formula: Specific lysis [%]=$(1-L_{exp}/L_{max})\times100$.

Example 2. Differential Expression of LILRB1 and PD-1 on Human CD8+ T Cells

PD-1 exerts essential repressive functions on CD8+ T cells, especially on tumor infiltrating exhausted CD8+ T cells. Therapeutic antibodies blocking PD-1 pathway can significantly enhance the effector functions and provide therapeutic benefits in many cancers. Given the fact that LILRB1 was also a negative regulator of CD8+ T cells, we studied the differences on the regulation and expression of LILRB1 and PD-1 on CD8+ T cell subsets.

Human PBMCs from healthy donor were stimulated with plate-bound anti-CD3 or plate-bound anti-CD3 plus anti-CD28 for 48 hours. Activated cells were collected for FACS analysis. Ex vivo FACS was performed with unstimulated PBMCs as control. FIG. 3 provides representative FACS plots showing LILRB1 and PD-1 expression on gated CD8+ T cells under the indicated conditions. Our data demonstrate that LILRB1 and PD-1 are differentially expressed by human CD8+ T cells following activation, with PD-1 being upregulated predominantly in LILRB1 negative populations.

We further discovered that PD-1 was highly expressed in $T_{EM}$ (effector memory cell, CD45RA–CCR7–) cells, while LILRB1 was highly expressed in TEFF (effector T cell, CD45RA+CCR7–) cells. In addition, LILRB1 is highly expressed in $T_{EMRA}$ CD8+ T cells, cells with most potent effector function. Representative data are shown in FIG. 1. The discovery is surprising, as most immune checkpoint proteins we studied are co-expressed with PD-1. LILRB1 is an exception. In fact, our data suggest that the expression of LILRB1 and PD-1 is likely mutually exclusive in tumor infiltrating CD8+ T cells (see e.g., FIGS. 5A-5B and FIGS. 4A-4B).

The expression of LILRB1 and PD-1 on CD8$^+$ T cells is also regulated differently. We discovered that while PD-1 expression is regulated by TCR activation (FIGS. 8A-8B). LILRB1 expression was not sensitive to TCR signaling (FIGS. 8A-8B). Blocking PD-1 pathway can further promote effector function of CD8+ T cells. Consistently, LILRB1+ effector cell population was significantly increased in 2 day activated CD8+ $T_{EM}$ cells when PD-1 pathway was blocked by recombinant PD-L1, while the expression of PD-1 was not significantly altered (FIGS. 8C-8D). Furthermore, effector promoting cytokines such as IL-2 and IL-15, but not TNFα, also significantly increased the LILRB1 expression on T cells (data not shown). Thus, strategies that enhanced CD8+ effector function, but not TCR activation alone, increased LILRB1+ CD8+ effector population.

Materials and Methods

Isolated human PBMCs were stimulated with 10 ng/ml recombinant human IL2, 10 ng/ml recombinant human IL15, or 100 ng/ml recombinant human TNF (all from R&D Systems) for 24 h. Sorted human CD8+ $T_{EM}$ cells were activated with plate-bound anti-CD3 (OKT3, 5 μg/ml, BD Biosciences) plus soluble anti-CD28 (CD28.2, 2 μg/ml, BD Biosciences) for 48 h. When indicated, 10 μg/ml recombinant human PD-L1 (Biolegend) or same amount of human IgG1 isotype control antibody were added in culture medium. Cells were cultured at 37° C. in RPMI-1640 supplemented with 10% heat-inactivated FBS, 100 U/mL penicillin and streptomycin, 2-Mercaptoethanol (all from Gibco)).

For flow cytometry, cells were stained with monoclonal antibodies (CD3-APC (Sk7, eBioscience), CD4-BV605 (OKT4, Biolegend), CD8-AF700 (RPA-T8, Biolegend), LILRB1-PE (GHI/75, Biolegend), and PD-1-BV650 (EH12.1, BD Bioscience). 7AAD was used for live dead staining (BD Biosciences). Cells were incubated with antibodies for 30 min at 4° C. followed by washing with FACS buffer (BD iosciences). Samples were acquired with LSR-II analyzer and analyzed using FlowJo software (v10.3).

Example 3. PD-1 is Preferentially Upregulated on LILRB1 Negative CD8+ Cells

Since only PD-1 but not LILRB1 was upregulated on CD8+ T cells upon T cell activation, we next asked whether there is a difference in the upregulation of PD-1 on either LILRB1$^+$ or LILRB1$^-$ CD8+ T cell subsets. PD-1 expression was upregulated preferentially from LILRB1$^-$ CD8+ T cells upon TCR stimulation (FIG. 3). Thus, it seems that expression of PD-1 and LILRB1 are mutually exclusive on CD8+ T cells, suggesting blocking PD-1 alone may not provide benefit on LILRB1$^+$ effector CD8+ T cells, and combined effect of blocking both PD-1 and LILRB1 may be synergistic.

Figure 4B:
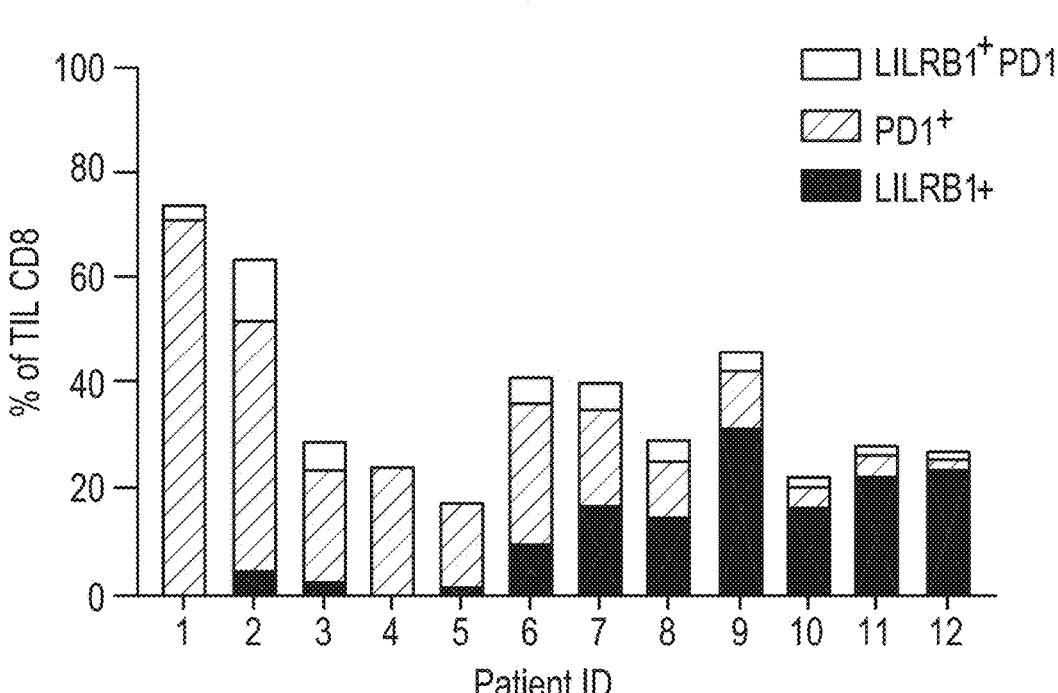

To confirm differential expression pattern of PD-1 and LILRB1 on different CD8+ subsets in human tumors, we evaluated the expression of LILRB1 and PD-1 on CD8$^+$ T cells isolated from NSCLC tumor tissues by FACS. We observed different expression patterns of these two markers in these tumor samples (FIG. 4A). While some NSCLC tumors had CD8+ T cells dominantly expressing either PD-1 or LILRB1, other tumors contained similar numbers of LILRB1$^+$ or PD-1$^+$ CD8+ cells (FIG. 4B). Nevertheless, in all the cases we examined, PD-1 and LILRB1 showed mutually exclusive expression pattern consistent with the data from healthy donor PBMCs. Importantly, LILRB1$^+$ CD8+ T cells were dominant in 5 out of 12 NSCLC tumors (FIG. 4B), suggesting LILRB1 blockade might be beneficial to these patients.

Furthermore, we analyzed publicly available single cell RNA sequencing data from HCC. In both datasets, LILRB1 and PD-1 showed mutually exclusive expression pattern in tumor CD8+ T cells (see, e.g., FIGS. 4A-4B). In contrast, expression patterns of other inhibitory receptors, such as TIGIT, TIM3, and CTLA-4, were largely overlapping with PD-1 (FIGS. 5A-5B).

Figure 4C:
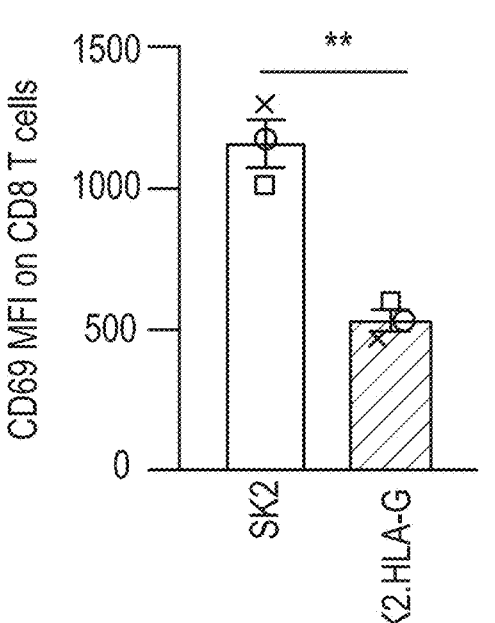
Figure 4D:
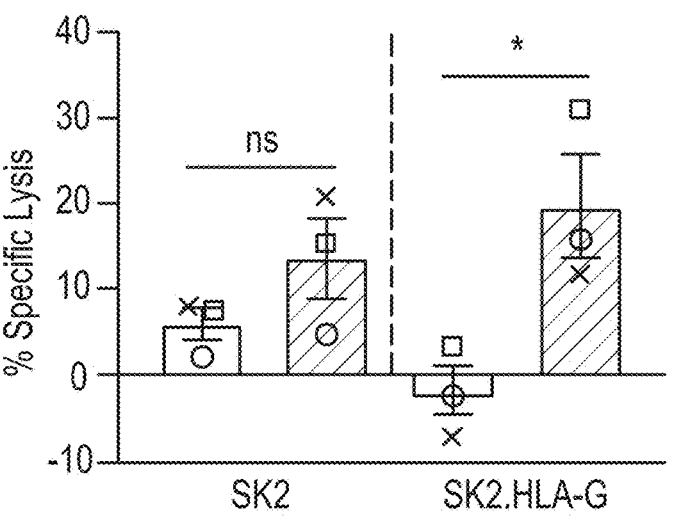

More importantly, when tumor infiltrating CD8+ T cells were isolated and used as effector T cells in a MART-1 BiTE® molecule-mediated cytotoxicity assay, we found that HLA-G overexpression on target tumor cells significantly inhibited BiTE® molecule-induced T cell activation (FIG. 4C) and cytolytic activity (FIG. 4D). Blockade of LILRB1 dramatically enhanced tumor CD8+ T cell effector function to kill HLA-G$^+$ target cells (FIG. 4D). Our results demonstrated that LILRB1 is a checkpoint inhibitor for tumor infiltrating effector CD8+ T cells. Blocking LILRB1 may enhance CD8+ T cell cytolytic activity against tumor cells in patients.

Materials and Methods

Human tumor dissociation. All human tumor specimens were collected under Institutional Review Board approval with appropriate informed consent. In all cases, materials obtained were surplus to standard clinical practice. Patient identity and PHI/identifying information were redacted from tissues and clinical data.

Lung tumor tissues were mechanically disrupted and incubated with the Liberase TL (Roche, 200 ug/ml) and DNase I (Roche, 20 U/ml): 1×MACS program h_tumor_1 using gentleMACS™ Octo Dissociator (Miltenyi Biotec), incubation at 37 C for 15 min, and then 1×MACS program h_tumor_02 to facilitate the release of lymphocytes from tissue. After the incubation, the tissue was passed through a 70 um filter to obtain a single cell suspension. The disaggregated tissues were centrifuge at 1500 rpm for 10 min and were re-suspended in DMEM/F12 containing 10% FBS (Life Technology, Carlsbad, CA, USA). Cells were blocked in FACS blocking buffer (1×PBS containing 5% FBS (Life Technology, Carlsbad, CA, USA) with 10 μg/ml each of normal human IgG (Rockland) and mouse IgG (Rockland), followed by antibody staining as described above.

Example 4. Synergistic Effects of Anti-PD-1 and Anti-LILRB1 Treatment

Figures 6A, 6B, 6C, 6D:
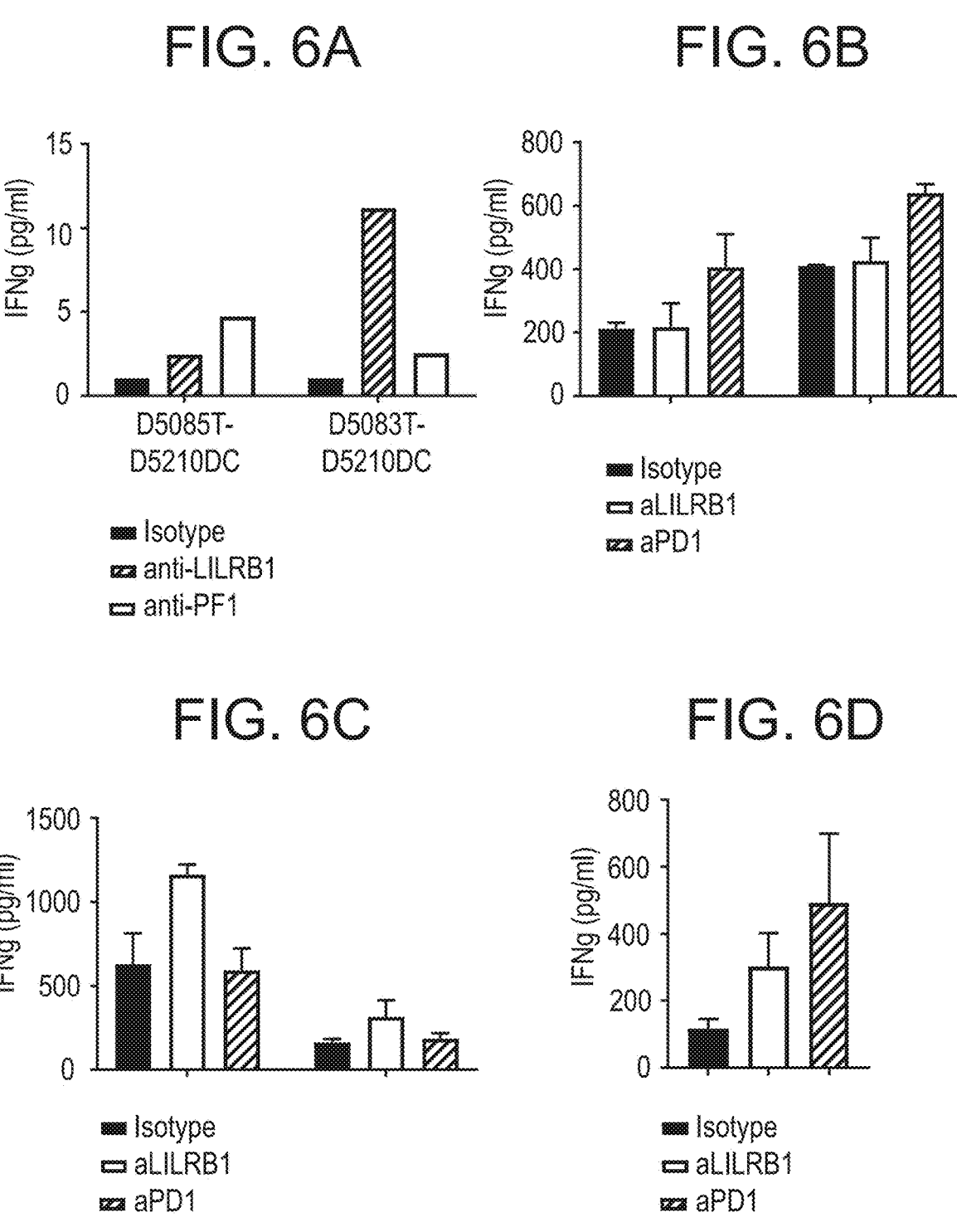
FIGS. 6A-6D show that certain sub-population of patients do not respond to anti-PD-1 treatment. However, some of the PD-1 non-responders show response to anti-LILRB1 blockade.

We discovered that there are certain patient sub-populations that do not respond to anti-PD-1 treatment in vitro. As shown in FIG. 6A-6D, anti-PD-1 increased CD8+ T cell activity in about 70% of donor pairs in mixed lymphocyte reaction assays, of which 3 out 5 PD-1 responding pairs also respond to anti-LILRB1 (FIGS. 6A and 6D). More importantly, anti-LILRB1 showed activity to enhance T cell function in mixed lymphocyte reaction assays in those 2 donor pairs that did not respond to anti-PD-1 (FIG. 6C).

Figure 7A:
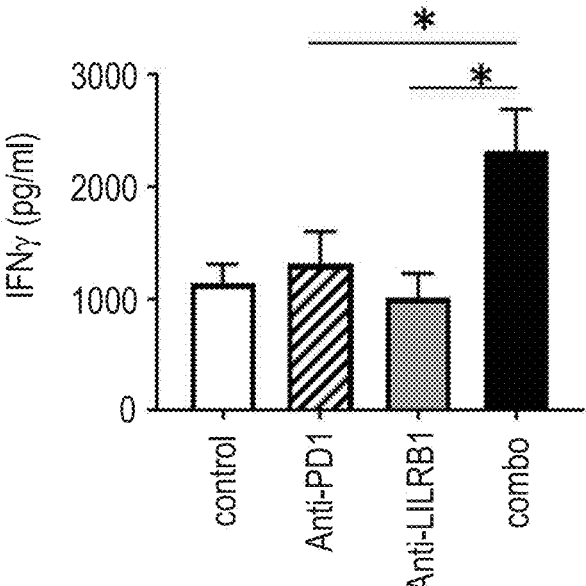
FIGS. 7A-7B show MLR assays with isolated total human T cells and allogenic DCs in the presence of the indicated blocking antibodies. IFNγ in day 5 supernatants were measured by ELISA. Data plotted as mean±SD *p<0.05.
Figure 7B:
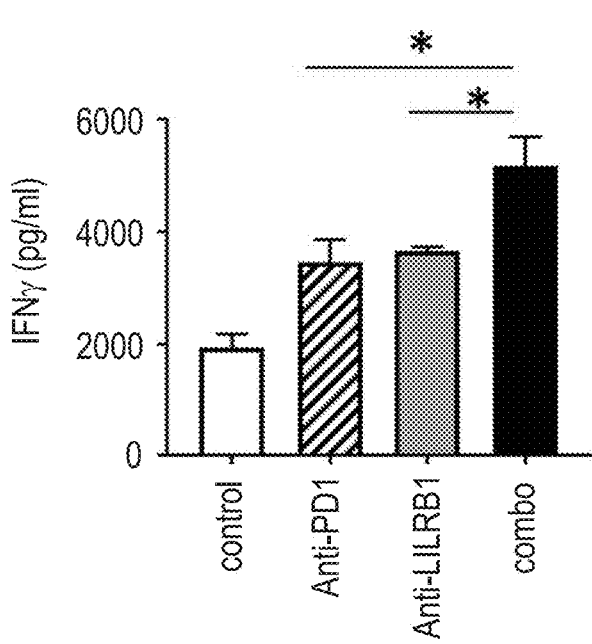

We next performed an MLR assay to compare effects of anti-LILRB1 or anti-PD-1 blockade alone or in combination on T cell activation. FIGS. 7A-7B shows MLR assay with isolated total human T cells and allogenic DCs in the presence of indicated blocking antibodies. Notable, in case of donor Pair #1, responses to anti-PD-1 alone, or anti-LILRB1 alone (as measured by IFNγ) were poor, each comparable to the control antibody. In stark contrast, response to the combined anti-PD-1 and anti-LILRB1 resulted in a significant increase in IFNγ production. Our results show that combination of anti-PD-1 and anti-LILRB1 blockade significantly increased IFNγ production in an MLR assay compared to the effect of single agent treatment (see, e.g., FIGS. 7A-7B, additional data not shown). Thus, blocking both pathways may further increase CD8+ T cell function.

In conclusion, we discovered that anti-PD-1 and anti-LILRB1 synergistically activated T cells in mixed lymphocyte reaction. Blocking both pathways significantly enhanced T cell activity and IFNγ production than blocking each pathway alone.

Materials and Methods

Mixed lymphocyte reaction. Isolated human total T cells or CD8+ cells were seeded into round-bottom 96-well plate (Corning) at $10^5$ per well together with $2\times10^4$ irradiated allogeneic CD11c$^+$ cell or MDDCs. When indicated, 10 μg/ml of anti-PD-1 (clone EH12.2H7, Biolegend) or anti-LILRB1 (clone GHI/75, Biolegend) were added to the culture. As control, 10 μg/ml of each matched isotype antibodies were used as control. Day 5 supernatants were collected and IFNγ level was determined by ELISA (BD Bioscience).

Example 5. Anti-PD1 Therapy Increases LILRB1 Expression on Effector CD8 T Cells in Syngeneic Tumor Model Mice or rats do not have a LILRB1 orthologue. To enable the assessment of the anti-PD1 checkpoint blockade treatment effects on LILRB1-expressing effector CD8 T cells in tumor, a LILRB1 transgenic mouse was generated by inserting a bacterial artificial chromosome (BAC) construct containing complete human LILRB1 gene into mouse genome. The resulting founders were confirmed to carry LILRB1 transgene by whole genome sequencing. A flow-activated cell sorting (FACS) analysis of peripheral blood mononuclear cells (PBMCs) obtained from transgenic mice confirmed that the expression of LILRB1 in subsets of immune cells from transgenic mice were similar to human LILRB1-expressing cells obtained from a healthy donor (data not shown).

Wild-type and transgenic mice were characterized in a phenotyping study and through clinical observations, body weights, clinical pathology, organ weights, and histopathology evaluation. Naïve transgenic mice phenocopied their wild-type littermates. No clinical observations, changes in body weight, or differences in clinical pathology parameters, organ weights, or histopathology were observed in any of the transgenic mice compared with wild-type mice. No differences were observed between wild-type and transgenic mice of the same sex in absolute numbers for the following immune cells in spleen and whole blood: CD4+ T cells, CD8+ T cells, B cells, natural killer cells, dendritic cells, monocytes, and macrophages.

In an in vivo study, when MC38 tumor cells overexpressing membrane ovalbumin (as a tumor-specific antigen (MC38.OVA)) were implanted in transgenic mice, OVA-specific tumor infiltrating CD8+ T cells expressed LILRB1 (FIGS. 9A-9B). This suggests that LILRB1$^+$ CD8 T cells are reactive to tumor antigen. Furthermore, tumor infiltrating LILRB1$^+$ CD8 T cells also express CX3CR1, perforin and IFNγ, as seen for LILRB1+ CD8 T cells in human tumors (Zheng, C. et al., 2017, Cell 169: 1342-1356.e1316; Guo, X. et al., 2018, Nat Med 24: 978-985).

To assess if anti-PD1 blockade affect LILRB1$^+$ T cells in tumor, tumor bearing LILRB1 transgenic mice were treated with anti-PD1 blocking antibody or isotype control antibody and the phenotypes of tumor infiltrating CD8 T cells were analyzed by flow cytometry. Our results showed that anti-PD1 significantly increased LILRB1+effector CD8 T cells in tumor (FIG. 10; see also, Kurtulus S. et al., 2019, Immunity 50: 181-194).

The in vivo data described herein support the concept that checkpoint blockade therapy (such as anti-PD-1) increases LILRB1 expression on effector CD8 T cells in tumor.

Materials and Methods

In vivo tumor study. All animal experiments were performed under protocols approved by the Institutional Animal Care and Use Committee (IACUC) of Amgen, Inc. All mice were sourced from Charles River Laboratories (Hollister, CA site) and were provided water and chow ad libitum and maintained in a pathogen-free facility. Mice used in syngeneic tumor experiments were 6-8 weeks of age at the time implant. MC38 cells overexpressing ovalbumin or HLA-G in serum-free RPMI were inoculated in the right flank at $3\times10^5$ cells per implant and allowed to grow for 10-14 days. For antibody treatment, the mice were then randomized by tumor volume (50-100 mm$^3$) and treated with anti-PD1 antibody or isotype control antibody (rat IgG2a) at 15 mg/kg intraperitoneally. Tumors and spleens were taken down 48 h post-treatment for pharmacodynamic studies.

Tissue dissociation. Tumors were mechanically disrupted and digested with Collagenase D (Roche, 0.5 mg/ml) and DNase I (Roche, 40 U/ml). Disruption was performed as follows: 1×MACS program h_tumor_03 using gentleMACS Octo Dissociator (Miltenyi Biotec), followed by incubation at 37° C. for 15 min, and further disruption by 2×MACS program h_tumor_02. Spleenocytes were prepared using m_spleen_01 program on gentleMACS Octo Dissociator (Miltenyi Biotec) following by lysing blood cells with ACK buffer (Thermo Fisher). After disruption, cells were passed through a 70 μm filter and washed with RPMI containing 10% FBS. The single cell suspension was centrifuged at 1,500 rpm for 5 min and resuspended in FACS blocking buffer.

Transgenic mice generation. Human LILRB1 gene containing BAC DNA were microinjected into C57BL/6J single cell embryos, followed by embryo transfer to pseudopregnant female animals to generate 4 LILRB1-BAC transgenic founders (Horizon Discovery). Lines #5 and #15 were chosen for further characterization based on flow cytometry analysis results for LILRB1 expression in peripheral mononuclear cells in these founders. Transgene insertion was confirmed using genomic DNA prepared from tail using alkaline lysis by PCR and sequencing. Primers designed to both the 5' end and 3' end of the BAC construct was used to PCR amplify the LILRB1-BAC. 5' end (Forward: 5'-AACC-CACCTGACTTGGATCA-3' and Reverse: 5'-TGAGGTATATGCAATCGTCAAAA-3' (SEQ ID Nos. 32, 33) and 3' end (Forward primer 5'-CTG-GAACTGGTGGTGACAGA-3' and Reverse primer-5'-TCTCCTCTAGGTGGTCAGCC-3') (SEQ ID Nos. 34, 35).

Example 6. Generation and Characterization of Anti-LILRB1 Antibodies

6.1 Generation of Anti-LILRB1 Antibodies

Mouse Strains. Fully human antibodies to human LILRB1 were generated by immunizing XENOMOUSE® transgenic mice (U.S. Pat. Nos. 6,114,598; 6,162,963; 6,833,268; 7,049,426; 7,064,244, which are incorporated herein by references in their entirety; Green et al., 1994, *Nature Genetics* 7:13-21; Mendez et al., 1997, *Nature Genetics* 15:146-156; Green and Jakobovitis, 1998, *J. Ex. Med*, 188:483-495; Kellerman and Green, *Current Opinion in Biotechnology* 13, 593-597, 2002). Animals from the XMG4-K and XMG4-KL XENOMOUSE® strains were used for these immunizations.

Immunizations. Multiple immunogens and routes of immunization were used to generate anti-human LILRB1 immune responses. For soluble recombinant protein immunizations, mice were immunized with alternating soluble human LILRB1-Fc and cynomolgus LILRB2-Fc. For cell-based immunizations, CHO-S cells were transiently transfected with either wild type human LILRB1 or cynomolgus LILRB2 as a source of immunogen. Animals were immunized with either of these transiently transfected CHO cells. Animals with the highest antigen-specific serum native titers directed against human LILRB1 and cynomolgus LILRB2 were used for hybridoma generation (Kohler and Milstein, 1975).

Hybridoma Generation. Animals exhibiting suitable serum titers were identified and lymphocytes were obtained from spleen and/or draining lymph nodes. Pooled lymphocytes (from each harvest) were dissociated from lymphoid tissue by grinding in a suitable medium (for example, Dulbecco's Modified Eagle Medium (DMEM); Invitrogen, Carlsbad, CA). B cells were selected and/or expanded using standard methods, and fused with a suitable fusion partner using techniques that were known in the art. Hybridoma supernatants with binding to human LILRB1 but no binding to human LILRA1 and human LILRA2 were then selected for further characterization.

Sequencing of LILRB1 Antagonist Antibodies. RNA (total or mRNA) was purified from wells containing the LILRB1 antagonist antibody-producing hybridoma cells using a Qiagen RNeasy mini or the Invitrogen mRNA catcher plus kit. Purified RNA was used to amplify the antibody heavy and light chain variable region (V) genes using cDNA synthesis via reverse transcription, followed by a polymerase chain reaction (RT-PCR). The fully human antibody gamma heavy chain was obtained using the Qiagen One Step Reverse Transcriptase PCR kit (Qiagen). The fully human kappa light chain was obtained using the Qiagen One Step Reverse Transcriptase PCR kit (Qiagen). Amino acid sequences were deduced from the corresponding nucleic acid sequences bioinformatically. The derived amino acid sequences were then analyzed to determine the germline sequence origin of the antibodies and to identify deviations from the germline sequence. The amino acid sequences corresponding to complementary determining regions (CDRs) of the sequenced antibodies were aligned and these alignments were used to group the clones by similarity.

Sequences of three exemplary anti-LILRB1 antibodies, 3C1, 30A10, and 19D6, are shown in the Sequence Table.

6.2 Functional Inhibition of Human LILRB1 Signaling

Jurkat cells stably expressing human LILRB1 and NFAT-luciferase reporter were used. For potency determination, hybridoma supernatant samples were serially titrated 3-fold in assay media and used to treat human LILRB1 reporter cells. Potency values for exemplary anti-LILRB1 antibodies from two repeat assays (n=1 and n=2) are shown in Table 1.

TABLE 1

| Antibody | Potency (nM) | |
| | n = 1 | n = 2 |
| --- | --- | --- |
| 3C1 | 0.040 | 0.024 |
| 19D6 | 0.084 | 0.095 |
| 30A10 | 0.062 | 0.042 |

The binding of hybridoma supernatants to LILRB1 expressed by primary human were tested by flow cytometry and the results are summarized in Table 2.

TABLE 2

| Antibody | FACS GeoMean, test 1 | Antibody | FACS GeoMean test 2 |
| --- | --- | --- | --- |
| 3C1 | 1753 | 19D6 | 2538 |
| Isotype | 73 | 30A10 | 2536 |
| | | Isotype | 359 |

6.3 LILRB1 Binding Domain Determination

To determine the LILRB1 domains to which antibody in hybridoma supernatant sample was binding to, HEK 293T cells transiently expressing domain truncated LILRB1 constructs were used in flow cytometry based binding assay. Full length or domain truncated human LILRB1 proteins were expressed on host HEK 293T cells by transfection using cDNA expression vectors. Transfected cells were cultured for overnight and then used to determine which LILRB1 domain the antibodies were binding to. Hybridoma supernatants of a specific antibody was added to 96-well plate. Each hybridoma supernatant sample was tested for binding to each of the full length and truncated LILRB1 protein expressed on HEK 293T. The binding data for each sample were then used to determine the LILRB1 domain to which it was binding.

TABLE 3a

| Deleted domains of LILRB1 | Remaining LILRB1 domains | Amino acid residues of remaining LILRB1 domains | Description |
| --- | --- | --- | --- |
| — | D1, D2, D3, D4, TM, ICD | 24-651 (SEQ ID NO: 3) | Full length human LILRB1 |
| D1 | D2, D3, D4, TM, ICD | 116-651 (SEQ ID NO: 3) | Human LILRB1 without D1 |

TABLE 3a-continued

| Deleted domains of LILRB1 | Remaining LILRB1 domains | Amino acid residues of remaining LILRB1 domains | Description |
|---|---|---|---|
| D1, D2 | D3, D4, TM, ICD | 222-651 (SEQ ID NO: 3) | Human LILRB1 without D1 and D2 |
| D1, D2, D3 | D4, TM, ICD | 313-651 (SEQ ID NO: 3) | Human LILRB1 without D1, D2 and D3 |

D: domain (D1: residues 27-115 of SEQ ID NO:3 or NO:6; D2, residues 116-221 of SEQ ID NO:3 or NO:6; D3: residues 222-312 of SEQ ID NO:3 or NO:6; D4: residues 313-409 of SEQ ID NO:3 or NO:6)
TM: transmembrane domain (residues 462-482 of SEQ ID NO:3 or NO:6)
ICD: intercellular domain (residues 483-650 of SEQ ID NO:6, residues 483-651 of SEQ ID NO:3)

TABLE 3b

| antibody | antibody binding domain |
|---|---|
| 3C1 | D4 |
| 19D6 | D4 |
| 30A10 | D3 |

6.4 Relative Epitope Binning/Profiling

A common way to characterize epitopes is through competition experiments. Antibodies that compete with each other can be thought of as binding the same or overlapping site on the target. This example describes a method of determining competition for binding to human LILRB1.

Binning experiments can be conducted in a number of ways, and the method employed may have an effect on the assay results. Common to these methods is that LILRB1 is typically bound by one reference antibody and probed by another. If the reference antibody prevents the binding of the probe antibody then the antibodies are said to be in the same bin. The order in which the antibodies are employed is also relevant. If antibody A is employed as the reference antibody and blocks the binding of antibody B the converse is not always true: antibody B used as the reference antibody will not necessarily block antibody A. There are a number of factors in play here: the binding of an antibody can cause conformational changes in the target which prevent the binding of the second antibody, or epitopes which overlap but do not completely occlude each other may allow for the second antibody to still have enough high-affinity interactions with the target to allow binding. In general, if competition is observed in either order the antibodies are said to bin together, and if both antibodies can block each other then it is likely that the epitopes overlap more completely.

In this example, a modified antibody-antibody competition assay was used to determine the relative epitope binning profiles of the LILRB1 specific antibodies in a high throughput manner. Briefly, individual antibodies were tested for their ability to compete for binding with a panel of reference antibodies chosen based on their different binding characteristics (e.g., ligand blocking, domain binding, etc.) and primary sequences. The pattern of competition/binding of each test antibody with the reference antibody panel was then determined and compared to those produced from the other test antibodies. The degree of correlation between the individual test antibody competition/binding profiles was then compared. Antibodies that showed similar competition/binding profiles were binned (grouped) together (e.g., Binning Profile A, B, etc.).

Biotinylated recombinant soluble human LILRB1 protein was coupled to streptavidin coated, uniquely barcoded LumAvidin Beads® for 30 minutes in the dark at room temperature and washed twice. The reference antibody hybridoma supernatant samples were incubated with the antigen-coated beads for 1 hour in the dark at room temperature and washed three times. Beads were resuspended in FACS buffer containing Stabilguard® (SurModics). The antigen-coated, reference antibody-bound beads were pooled and then divided into individual sample wells containing a normalized (5 ug/ml) test antibody (hybridoma supernatant) sample (or negative control), incubated for 1 hour in the dark at room temperature and washed twice. The samples were then incubated with mouse anti-human IgG 2, 3, 4 antibody and incubated for 30 minutes in the dark at room temperature and washed twice. Antibodies bound to LILRB1 protein were then detected by incubating the samples with Alexa Fluor®488 mouse IgG fragment-specific detection antibody for 15 minutes in the dark at room temperature, washed once and resuspended in FACS buffer. Samples were analyzed using an BD Accuri™ Flow Cytometer and an Intellicyt HyperCyt autoSampler.

To determine the antibody competition/binding profiles of the individual test antibodies, the reference-only antibody binding signal was subtracted from the reference plus test antibody signal for each competition/binding reaction (ie. across the entire reference antibody set). An individual antibody binding profile was defined as the collection of net binding values for each competition/binding reaction. The degree of similarity between individual profiles was then assessed by calculating the coefficient of determination between each of the test antibody profiles. Test antibodies showing high degrees of similarity ($R2>0.8$) to each other were then grouped into common binning profiles. Separate binning profiles were only defined if there were two or more samples with a high degree of correlation. If individual unique antibody binning profiles were observed (ie. they displayed a low degree of similarity to other test antibody binding profiles), the bin was classified as unknown. Using this method, the LILRB1 binding antibodies were subdivided into unique binning profiles (A, B, C, etc.) (Table 4).

TABLE 4

| Antibody ID | Epitope BIN |
|---|---|
| 3C1 | C |
| 19D6 | C |
| 30A10 | C |

6.5 Affinities of the Anti-LILRB1 Antibodies

Affinity was measured on ForteBio Octet HTX (Molecular Devices) using SA biosensors (cat 18-5010) using assay buffer comprised of 10 mM Tris, 0.1% TritonX, 150 mM NaCl, 1 mM CaCl$_2$), 1 mg/mL BSA, pH 7.4. Assay was conducted at 25° C. and 1:1 model was used to fit the curves. Biotinylated goat anti-human Fc at 0.75 ug/mL was captured on SA sensors and antibodies as unpurified but quantified hybridoma supernatant were loaded on the sensor at 2 ug/mL for 600 seconds. Recombinant human LILRB1 (R&D Systems) titrated 1:2 from 25 nM was allowed to bind for 5 minutes, then dissociation was measured for 20 minutes. The results are shown in Table 5.

TABLE 5

| Antibody | $K_D \times 10^{-9}$ (M) | $k_{on}$ (1/Ms) | $K_{dis}$ (1/s) |
|----------|------------------|-----------|-----------|
| 3C1 | 1.68E−10 | 1.47E+06 | 2.47E−04 |
| 19D6 | 1.76E−10 | 1.17E+06 | 2.06E−04 |
| 30A10 | 1.03E−10 | 1.17E+06 | 1.20E−04 |

5

SEQUENCES

| SEQ ID | Description | sequence |
|--------|-------------|----------|
| 1 | Q15116\|PDCD1_HUMAN Programmed cell death protein 1 (PD-1) | MQIPQAPWPVVWAVLQLGWRPGWELDSPDRPWNPPTESPALLVVTEGDNATFT CSFSNTSESFVLNWYRMSPSNQTDKLAAFPEDRSQPGQDCRFRVTQLPNGRDF HMSVVRARRNDSGTYLCGAISLAPKAQIKESLRAELRVTERRAEVPTAHPSPS PRPAGQFQTLVVGVVGGLLGSLVLLVWVLAVICSRAARGTIGARRTGQPLKED PSAVPVFSVDYGELDFQWREKTPEPPVPCVPEQTEYATIVFPSGMGTSSPARR GSADGPRSAQPLRPEDGHCSWPL |
| 2 | Q9NZQ7\|PD-1L1_HUMAN Programmed cell death 1 ligand 1 (PD-L1) | MRIFAVFIFMTYWHLLNAFTVTVPKDLYVVEYGSNMTIECKFPVEKQLDLAAL IVYWEMEDKNIIQFVHGEEDLKVQHSSYRQRARLLKDQLSLGNAALQITDVKL QDAGVYRCMISYGGADYKRITVKVNAPYNKINQRILVVDPVTSEHELTCQAEG YPKAEVIWTSSDHQVLSGKTTTTNSKREEKLENVTSTLRINTTTNEIFYCTER RLDPEENHTAELVIPELPLAHPPNERTHLVILGAILLCLGVALTFIFRLRKGR MMDVKKCGIQDTNSKKQSDTHLEET |
| 3 | Q8NHL6\|LIRB1_HUMAN Leukocyte immunoglobulin-like receptor subfamily B member 1 (LILRB1) | MTPILTVLICLGLSLGPRTHVQAGHLPKPTLWAEPGSVITQGSPVTLRCQGGQ ETQEYRLYREKKTALWITRIPQELVKKGQFPIPSITWEHAGRYRCYYGSDTAG RSESSDPLELVVTGAYIKPTLSAQPSPVVNSGGNVILQCDSQVAFDGFSLCKE GEDEHPQCLNSQPHARGSSRAIFSVGPVSPSRRWWYRCYAYDSNSPYEWSLPS DLLELLVLGVSKKPSLSVQPGPIVAPEETLTLQCGSDAGYNRFVLYKDGERDF LQLAGAQPQAGLSQANFTLGPVSRSYGGQYRCYGAHNLSSEWSAPSDPLDILI AGQFYDRVSLSVQPGPTVASGENVTLLCQSQGWMQTFLLTKEGAADDPWRLRS TYQSQKYQAEFPMGPVTSAHAGTYRCYGSQSSKPYLLTHPSDPLELVVSGPSG GPSSPTTGPTSTSGPEDQPLTPTGSDPQSGLGRHLGVVIGILVAVILLLLLL LLFLILRHRRQGKHWTSTQRKADFQHPAGAVGPEPTDRGLQWRSSPAADAQEE NLYAAVKHTQPEDGVEMDTRSPHDEDPQAVTYAEVKHSRPRREMASPPSPLSG EFLDTKDRQAEEDRQMDTEAAASEAPQDVTYAQLHSLTLRREATEPPPSQEGP SPAVPSIYATLAIH |
| 4 | Q8NHL6-2\|LIRB1_HUMAN Isoform 2 of Leukocyte immunoglobulin-like receptor subfamily B member 1 OS = Homo sapiens OX = 9606 GN = LILRB1 | MTPILTVLICLGLSLGPRTHVQAGHLPKPTLWAEPGSVITQGSPVTLRCQGGQ ETQEYRLYREKKTALWITRIPQELVKKGQFPIPSITWEHAGRYRCYYGSDTAG RSESSDPLELVVTGAYIKPTLSAQPSPVVNSGGNVILQCDSQVAFDGESLCKE GEDEHPQCLNSQPHARGSSRAIFSVGPVSPSRRWWYRCYAYDSNSPYEWSLPS DLLELLVLGVSKKPSLSVQPGPIVAPEETLTLQCGSDAGYNRFVLYKDGERDF LQLAGAQPQAGLSQANFTLGPVSRSYGGQYRCYGAHNLSSEWSAPSDPLDILI AGQFYDRVSLSVQPGPTVASGENVTLLCQSQGWMQTELLTKE GAADDPWRLRSTYQSQKYQAEFPMGPVTSAHAGTYRCYGSQSSKPYLLTHPSD PLELVVSGPSGGPSSPTTGPTSTSAGPEDQPLTPTGSDPQSGLGRHLGVVIGI LVAVILLLLLLLLFLILRHRRQGKHWTSTQRKADFQHPAGAVGPEPTDRGLQ WRSSPAADAQEENLYAAVKHTQPEDGVEMDTRSPHDEDPQAVTYAEVKHSRPR REMASPPSPLSGEFLDTKDRQAEEDRQMDTEAAASEAPQDVTYAQLHSLTLRR EATEPPPSQEGPSPAVPSIYATLAIH |
| 5 | Q8NHL6-3\|LIRB1_HUMAN Isoform 3 of Leukocyte immunoglobulin-like receptor subfamily B member 1 OS = Homo sapiens OX = 9606 GN = LILRB1 | MTPILTVLICLGLSLGPRTHVQAGHLPKPTLWAEPGSVITQGSPVTLRCQGGQ ETQEYRLYREKKTALWITRIPQELVKKGQFPIPSITWEHAGRYRCYYGSDTAG RSESSDPLELVVTGAYIKPTLSAQPSPVVNSGGNVILQCDSQVAFDGESLCKE GEDEHPQCLNSQPHARGSSRAIFSVGPVSPSRRWWYRCYAYDSNSPYEWSLPS DLLELLVLGVSKKPSLSVQPGPIVAPEETLTLQCGSDAGYNRFVLYKDGERDF LQLAGAQPQAGLSQANFTLGPVSRSYGGQYRCYGAHNLSSEWSAPSDPLDILI AGQFYDRVSLSVQPGPTVASGENVTLLCQSQGWMQTFLLTKEGAADDPWRLRS TYQSQKYQAEFPMGPVTSAHAGTYRCYGSQSSKPYLLTHPSDPLELVVSGPSG GPSSPTTGPTSTSAGPEDQPLTPTGSDPQSGLGRHLGVVIGILVAVILLLLLL LLLFLILRHRRQGKHWTSTQRKADFQHPAGAVGPEPTDRGLQWRSSPAADAQE ENLYAAVKHTQPEDGVEMDTRSPHDEDPQAVTYAEVKHSRPRREMASPPSPL SGEFLDTKDRQAEEDRQMDTEAAASEAPQDVTYAQLHSLTLRREATEPPPSQE GPSPAVPSIYATLAIH |
| 6 | Q8NHL6-4\|LIRB1_HUMAN Isoform 4 of Leukocyte immunoglobulin-like receptor subfamily B member 1 OS = Homo sapiens | MTPILTVLICLGLSLGPRTHVQAGHLPKPTLWAEPGSVITQGSPVTLRCQGGQ ETQEYRLYREKKTALWITRIPQELVKKGQFPIPSITWEHAGRYRCYYGSDTAG RSESSDPLELVVTGAYIKPTLSAQPSPVVNSGGNVILQCDSQVAFDGFSLCKE GEDEHPQCLNSQPHARGSSRAIFSVGPVSPSRRWWYRCYAYDSNSPYEWSLPS DLLELLVLGVSKKPSLSVQPGPIVAPEETLTLQCGSDAGYNRFVLYKDGERDF LQLAGAQPQAGLSQANFTLGPVSRSYGGQYRCYGAHNLSSEWSAPSDPLDILI AGQFYDRVSLSVQPGPTVASGENVTLLCQSQGWMQTFLLTKEGAADDPWRLRS TYQSQKYQAEFPMGPVTSAHAGTYRCYGSQSSKPYLLTHPSDPLELVVSGPSG GPSSPTTGPTSTSGPEDQPLTPTGSDPQSGLGRHLGVVIGILVAVILLLLLLL |

-continued

| SEQUENCES | | |
|---|---|---|
| SEQ<br>ID | Description | sequence |
| | OX = 9606<br>GN = LILRB1 | LLFLILRHRRQGKHWTSTQRKADFQHPAGAVGPEPTDRGLQWRSSPAADAQEE<br>NLYAAVKHTQPEDGVEMDTRQSPHDEDPQAVTYAEVKHSRPRREMASPPSPLS<br>GEFLDTKDRQAEEDRQMDTEAAASEAPQDVTYAQLHSLTLRREATEPPPSQEG<br>PSPAVPSIYATLAIH |
| 7 | Q8NHL6-<br>5\|LIRB1_HUMAN<br>Isoform 5 of<br>Leukocyte<br>immunoglobulin-<br>like receptor<br>subfamily B<br>member 1<br>OS = Homo sapiens<br>OX = 9606<br>GN = LILRB1 | MTPILTVLICLGLSLGPRTHVQAGHLPKPTLWAEPGSVITQGSPVTLRCQGGQ<br>ETQEYRLYREKKTALWITRIPQELVKKGQFPIPSITWEHAGRYRCYYGSDTAG<br>RSESSDPLELVVTGAYIKPTLSAQPSPVVNSGGNVILQCDSQVAFDGFSLCKE<br>GEDEHPQCLNSQPHARGSSRAIFSVGPVSPSRRWWYRCYAYDSNSPYEWSLPS<br>DLLELLVLGVSKKPSLSVQPGPIVAPEETLTLQCGSDAGYNRFVLYKDGERDF<br>LQLAGAQPQAGLSQANFTLGPVSRSYGGQYRCYGAHNLSSEWSAPSDPLDILI<br>AGQFYDRVSLSVQPGPTVASGENVTLLCQSQGWMQTFLLTKEGAADDPWRLRS<br>TYQSQKYQAEFPMGPVTSAHAGTYRCYGSQSSKPYLLTHPSDPLELVVSGPSG<br>GPSSPTTGPTSTSAGPEDQPLTPTGSDPQSGE |
| 8 | Q8N423\|LIRB2_HUMAN<br>Leukocyte<br>immunoglobulin-<br>like receptor<br>subfamily B<br>member 2<br>(LILRB2) | MTPIVTVLICLGLSLGPRTHVQTGTIPKPTLWAEPDSVITQGSPVTLSCQGSL<br>EAQEYRLYREKKSASWITRIRPELVKNGQFHIPSITWEHTGRYGCQYYSRARW<br>SELSDPLVLVMTGAYPKPTLSAQPSPVVTSGGRVTLQCESQVAFGGFILCKEG<br>EEEHPQCLNSQPHARGSSRAIFSVGPVSPNRRWSHRCYGYDLNSPYVWSSPSD<br>LLELLVPGVSKKPSLSVQPGPVVAPGESLTLQCVSDVGYDREVLYKEGERDLR<br>QLPGRQPQAGLSQANFTLGPVSRSYGGQYRCYGAHNLSSECSAPSDPLDILIT<br>GQIRGTPFISVQPGPTVASGENVTLLCQSWRQFHTFLLTKAGAADAPLRLRSI<br>HEYPKYQAEFPMSPVTSAHAGTYRCYGSLNSDPYLLSHPSEPLELVVSGPSMG<br>SSPPPTGPISTPAGPEDQPLTPTGSDPQSGLGRHLGVVIGILVAVVLLLLLLL<br>LLFLILRHRRQGKHWTSTQRKADFQHPAGAVGPEPTDRGLQWRSSPAADAQEE<br>NLYAAVKDTQPEDGVEMDTRAAASEAPQDVTYAQLHSLTLRRKATEPPPSQER<br>EPPAEPSIYATLAIH |
| 9 | Q8N423-<br>2\|LIRB2_HUMAN<br>Isoform 2 of<br>Leukocyte<br>immunoglobulin-<br>like receptor<br>subfamily B<br>member 2<br>OS = Homo sapiens<br>OX = 9606<br>GN = LILRB2 | MTPIVTVLICLGLSLGPRTHVQTGTIPKPTLWAEPDSVITQGSPVTLSCQGSL<br>EAQEYRLYREKKSASWITRIRPELVKNGQFHIPSITWEHTGRYGCQYYSRARW<br>SELSDPLVLVMTGAYPKPTLSAQPSPVVTSGGRVTLQCESQVAFGGFILCKEG<br>EEEHPQCLNSQPHARGSSRAIFSVGPVSPNRRWSHRCYGYDLNSPYVWSSPSD<br>LLELLVPGVSKKPSLSVQPGPVVAPGESLTLQCVSDVGYDREVLYKEGERDLR<br>QLPGRQPQAGLSQANFTLGPVSRSYGGQYRCYGAHNLSSECSAPSDPLDILIT<br>GQIRGTPFISVQPGPTVASGENVTLLCQSWRQFHTFLLTKAGAADAPLRLRSI<br>HEYPKYQAEFPMSPVTSAHAGTYRCYGSLNSDPYLLSHPSEPLELVVSGPSMG<br>SSPPPTGPISTPGPEDQPLTPTGSDPQSGLGRHLGVVIGILVAVVLLLLLLLL<br>LFLILRHRRQGKHWTSTQRKADFQHPAGAVGPEPTDRGLQWRSSPAADAQEEN<br>LYAAVKDTQPEDGVEMDTRAAASEAPQDVTYAQLHSLTLRRKATEPPPSQERE<br>PPAEPSIYATLAIH |
| 10 | Q8N423-<br>3\|LIRB2_HUMAN<br>Isoform 3 of<br>Leukocyte<br>immunoglobulin-<br>like receptor<br>subfamily B<br>member 2<br>OS = Homo sapiens<br>OX = 9606<br>GN = LILRB2 | MTPIVTVLICLGLSLGPRTHVQTGTIPKPTLWAEPDSVITQGSPVTLSCQGSL<br>EAQEYRLYREKKSASWITRIRPELVKNGQFHIPSITWEHTGRYGCQYYSRARW<br>SELSDPLVLVMTGAYPKPTLSAQPSPVVTSGGRVTLQCESQVAFGGFILCKEG<br>EEEHPQCLNSQPHARGSSRAIFSVGPVSPNRRWSHRCYGYDLNSPYVWSSPSD<br>LLELLVPGVSKKPSLSVQPGPVVAPGESLTLQCVSDVGYDREVLYKEGERDLR<br>QLPGRQPQAGLSQANFTLGPVSRSYGGQYRCYGAHNLSSECSAPSDPLDILIT<br>GQIRGTPFISVQPGPTVASGENVTLLCQSWRQFHTFLLTKAGAADAPLRLRSI<br>HEYPKYQAEFPMSPVTSAHAGTYRCYGSLNSDPYLLSHPSEPLELVVSGPSMG<br>SSPPPTGPISTPAGPEDQPLTPTGSDPQSGLGRHLGVVIGILVAVVLLLLLLL<br>LLFLILRHRRQGKHWTSSPAQLPTPRKKTSMLP |
| 11 | Q8N423-<br>4\|LIRB2_HUMAN<br>Isoform 4 of<br>Leukocyte<br>immunoglobulin-<br>like receptor<br>subfamily<br>member 2<br>OS = Homo sapiens<br>OX = 9606<br>GN = LILRB2 | MTGAYPKPTLSAQPSPVVTSGGRVTLQCESQVAFGGFILCKEGEEEHPQCLNS<br>QPHARGSSRAIFSVGPVSPNRRWSHRCYGYDLNSPYVWSSPSDLLELLVPGVS<br>KKPSLSVQPGPVVAPGESLTLQCVSDVGYDRFVLYKEGERDLRQLPGRQPQAG<br>LSQANFTLGPVSRSYGGQYRCYGAHNLSSECSAPSDPLDILITGQIRGTPFIS<br>VQPGPTVASGENVTLLCQSWRQFHTFLLTKAGAADAPLRLRSIHEYPKYQAEF<br>PMSPVTSAHAGTYRCYGSLNSDPYLLSHPSEPLELVVSGPSMGSSPPPTGPIS<br>TPAGPEDQPLTPTGSDPQSGLGRHLGVVIGILVAVVLLLLLLLLLLFLILRHRR<br>QGKHWTSTQRKADFQHPAGAVGPEPTDRGLQWRSSPAADAQEENLYAAVKDTQ<br>PEDGVEMDTRAAASEAPQDVTYAQLHSLTLRRKATEPPPSQEREPPAEPSIYA<br>TLAIH |
| 12 | P17693\|HLAG_HUMAN<br>HLA class I<br>histocompatibility<br>antigen,<br>alpha chain G | MVVMAPRTLFLLLSGALTLTETWAGSHSMRYFSAAVSRPGRGEPRFIAMGYVD<br>DTQFVRFDSDSACPRMEPRAPWVEQEGPEYWEEETRNTKAHAQTDRMNLQTLR<br>GYYNQSEASSHTLQWMIGCDLGSDGRLLRGYEQYAYDGKDYLALNEDLRSWTA<br>ADTAAQISKRKCEAANVAEQRRAYLEGTCVEWLHRYLENGKEMLQRADPPKTH<br>VTHHPVFDYEATLRCWALGFYPAEIILTWQRDGEDQTQDVELVETRPAGDGTF<br>QKWAAVVVPSGEEQRYTCHVQHEGLPEPLMLRWKQSSLPTIPIMGIVAGLVVL<br>AAVVTGAAVAAVLWRKKSSD |

-continued

| SEQUENCES | | |
|---|---|---|

| SEQ ID | Description | sequence |
|---|---|---|
| 13 | P17693-2\|HLAG_HUMAN Isoform 2 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEAKPPKTHVTHHPVFDYEATLRCWALGFYPAEIILTWQRDGEDQTQD VELVETRPAGDGTFQKWAAVVVPSGEEQRYTCHVQHEGLPEPLMLRWKQSSLP TIPIMGIVAGLVVLAAVVTGAAVAAVLWRKKSSD |
| 14 | P17693-3\|HLAG_HUMAN Isoform 3 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEAKQSSLPTIPIMGIVAGLVVLAAVVTGAAVAAVLWRKKSSD |
| 15 | P17693-4\|HLAG_HUMAN Isoform 4 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEASSHTLQWMIGCDLGSDGRLLRGYEQYAYDGKDYLALNEDLRSWTA ADTAAQISKRKCEAANVAEQRRAYLEGTCVEWLHRYLENGKEMLQRAKQSSLP TIPIMGIVAGLVVLAAVVTGAAVAAVLWRKKSSD |
| 16 | P17693-5\|HLAG_HUMAN Isoform 5 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEASSHTLQWMIGCDLGSDGRLLRGYEQYAYDGKDYLALNEDLRSWTA ADTAAQISKRKCEAANVAEQRRAYLEGTCVEWLHRYLENGKEMLQRADPPKTH VTHHPVFDYEATLRCWALGFYPAEIILTWQRDGEDQTQDVELVETRPAGDGTF QKWAAVVVPSGEEQRYTCHVQHEGLPEPLMLRWSKEGDGGIMSVRESRSLSED L |
| 17 | P17693-6\|HLAG_HUMAN Isoform 6 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEAKPPKTHVTHHPVFDYEATLRCWALGFYPAEIILTWQRDGEDQTQD VELVETRPAGDGTFQKWAAVVVPSGEEQRYTCHVQHEGLPEPLMLRWSKEGDG GIMSVRESRSLSEDL |
| 18 | P17693-7\|HLAG_HUMAN Isoform 7 of HLA class I histocompatibil ity antigen, alpha chain G OS = Homo sapiens OX = 9606 GN = HLA-G | MVVMAPRTLFLLLSGALTLTETWAGSHSMRYFSAAVSRPGRGEPRFIAMGYVD DTQFVRFDSDSACPRMEPRAPWVEQEGPEYWEEETRNTKAHAQTDRMNLQTLR GYYNQSEASE |
| 19 | 20C1 HC CDR1 | SYDMS |
| 20 | 20C1 HC CDR2 | LISGGGSQTYYAESVKG |
| 21 | 20C1 HC CDR3 | PSGHYFYAMDV |
| 22 | 20C1 LC CDR1 | RASQGISNWLA |

-continued

| SEQUENCES | | |
|---|---|---|
| SEQ ID | Description | sequence |
| 23 | 20C1 LC CDR2 | AASSLQS |
| 24 | 20C1 LC CDR3 | QQAESFPHT |
| 25 | 20C1 HC VARIABLE | EVQLLESGGGLVQPGGSLRLSCAASGFTFSSYDMSWVRQAPGKGLEWVSLISG GGSQTYYAESVKGRFTISRDNSKNTLYLQMNSLRAEDTAVYFCASPSGHYFYA MDVWGQGTTVTVSS |
| 26 | 20C1 LC VARIABLE | DIQMTQSPSSVSASVGDRVTITCRASQGISNWLAWYQQKPGKAPKLLIFAASS LQSGVPSRFSGSGSGTDFTLTISSLQPEDFATYYCQQAESFPHTFGGGTKVEI K |
| 27 | 20C1 HC FULL LENGTH | MDMRVPAQLLGLLLLWLRGARCEVQLLESGGGLVQPGGSLRLSCAASGFTESS YDMSWVRQAPGKGLEWVSLISGGGSQTYYAESVKGRFTISRDNSKNTLYLQMN SLRAEDTAVYFCASPSGHYFYAMDVWGQGTTVTVSSASTKGPSVFPLAPSSKS TSGGTAALGCLVKDYFPEPVTVSWNSGALTSGVHTFPAVLQSSGLYSLSSVVT VPSSSLGTQTYICNVNHKPSNTKVDKKV EPKSCDKTHTCPPCPAPELLGGPSVFLFPPKPKDTLMISRTPEVTCVVVDVSH EDPEVKFNWYVDGVEVHNAKTKPCEEQYGSTYRCVSVLTVLHQDWLNGKEYKC KVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSV MHEALHNHYTQKSLSLSPGK |
| 28 | 20C1 LC FULL LENGTH | MDMRVPAQLLGLLLLWLRGARCDIQMTQSPSSVSASVGDRVTITCRASQGISN WLAWYQQKPGKAPKLLIFAASSLQSGVPSRFSGSGSGTDFTLTISSLQPEDFA TYYCQQAESFPHTFGGGTKVEIKRTVAAPSVFIFPPSDEQLKSGTASVVCLLN NFYPREAKVQWKVDNALQSGNSQESVTEQDSKDSTYSLSSTLTLSKADYEKHK VYACEVTHQGLSSPVTKSENRGEC |
| 29 | 20C1 Heavy chain constant region | ASTKGPSVFPLAPSSKSTSGGTAALGCLVKDYFPEPVTVSWNSGALTGVHTFP AVLQSSGLYSLSSVVTVPSSSLGTQTYICNVNHKPSNTKVDKKVEPKSCDKTH TCPPCPAPELLGGPSVFLFPPKPKDTLMISRTPEVTCVVVDVSHEDPEVKENW YVDGVEVHNAKTKPREEQYNSTYRVVSVLTVLHQDWLNGKEYKCKVSNKALPA PIEKTISKAKGQPREPQVYTLPPSREE MTKNQVSLTCLVKGFYPSDIAVEWESNGQPENNYKTTPPVLDSDGSFFLYSKL TVDKSRWQQGNVFSCSVMHEALHNHYTQKSLSLSPGK |
| 30 | 20C1 Light chain constant region | RTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSENRGE C |
| 31 | siRNA targeting HLA-G | GGCUGAACAAAGGAGAtt |
| 32 | Primer for transgenic mouse | AACCCACCTGACTTGGATCA |
| 33 | Primer for transgenic mouse | TGAGGTATATGCAATCGTCAAAA |
| 34 | Primer for transgenic mouse | CTGGAACTGGTGGTGACAGA |
| 35 | Primer for transgenic mouse | TCTCCTCTAGGTGGTCAGCC |
| 36 | 3C1 HC CDR1 | DYDMH |
| 37 | 3C1 HC CDR2 | TIDTAGDTYYPDSVRG |
| 38 | 3C1 HC CDR3 | DVPGTGFDH |
| 39 | 3C1 LC CDR1 | QGDSLRSYYES |
| 40 | 3C1 LC CDR2 | GKNNRPS |
| 41 | 3C1 LC CDR3 | NSRDNSGDHWV |
| 42 | 3C1 HC VARIABLE | EVQLVESGGGLVQPGGSLRLSCAASGFTFSDYDMHWVRQATGKGLEWVATIDT |

-continued

| SEQUENCES | | |
|---|---|---|
| SEQ ID | Description | sequence |

|  |  |  |
|---|---|---|
|  |  | AGDTYYPDSVRGRFTISRENAKNSLSLQMNSLRAGDTAVYFCARDVPGTGFDH WGQGTLVTVSS |
| 43 | 3C1 LC VARIABLE | SSELTQDPAVSVALGQTVRITCQGDSLRSYYESWYQQKPGQAPVLVIYGKNNR PSGIPDRFSGSISGNTASLTITGTQAEDEADYYCNSRDNSGDHWVFGGGTRLT VL |
| 44 | 3C1 HC FULL LENGTH | MDMRVPAQLLGLLLLWLRGARCEVQLVESGGGLVQPGGSLRLSCAASGFTFSD YDMHWVRQATGKGLEWVATIDTAGDTYYPDSVRGRFTISRENAKNSLSLQMNS LRAGDTAVYFCARDVPGTGFDHWGQGTLVTVSSASTKGPSVFPLAPCSRSTSE STAALGCLVKDYFPEPVTVSWNSGALTSGVHTFPAVLQSSGLYSLSSVVTVPS SSLGTKTYTCNVDHKPSNTKVDKRVESKYGPPCPSCPAPEFLGGPSVFLFPPK PKDTLMISRTPEVTCVVVDVSQEDPEVQFNWYVDGVEVHNAKTKPREEQENST YRVVSVLTVLHQDWLNGKEYKCKVSNKGLPSSIEKTISKAKGQPREPQVYTLP PSQEEMTKNQVSLTCLVKGFYPSDIAVEWESNGQPENNYKTTPPVLDSDGSFF LYSRLTVDKSRWQEGNVFSCSVMHEALHNHYTQKSLSLSLGK |
| 45 | 3C1 LC FULL LENGTH | MDMRVPAQLLGLLLLWLRGARCSSELTQDPAVSVALGQTVRITCQGDSLRSYY ESWYQQKPGQAPVLVIYGKNNRPSGIPDRESGSISGNTASLTITGTQAEDEAD YYCNSRDNSGDHWVFGGGTRLTVLGQPKAAPSVTLFPPSSEELQANKATLVCL ISDFYPGAVTVAWKADSSPVKAGVETTTPSKQSNNKYAASSYLSLTPEQWKSH RSYSCQVTHEGSTVEKTVAPTECS |
| 46 | 3C1 Heavy chain constant region | ASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPC PSCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGK |
| 47 | 3C9 light chain constant region | GQPKAAPSVTLFPPSSEELQANKATLVCLISDFYPGAVTVAWKADSSPVKAGV ETTTPSKQSNNKYAASSYLSLTPEQWKSHRSYSCQVTHEGSTVEKTVAPTECS |
| 48 | 30A10 HC CDR1 | SYAMH |
| 49 | 30A10 HC CDR2 | IIWFDGSQRYYADSVKG |
| 50 | 30A10 HC CDR3 | DELTGFDY |
| 51 | 30A10 LC CDR1 | RASQNIINFLN |
| 52 | 30A10 LC CDR2 | AASSLRS |
| 53 | 30A10 LC CDR3 | QQSFSTPLT |
| 54 | 30A10 HC VARIABLE | QVQLVESGGGVVQPGRSLRLSCAASGFTFSSYAMHWVRQAPGKGLEWVAIIWF DGSQRYYADSVKGRFTISRDNSRDTLYLQMNSLRAEDTAVYYCARDELTGFDY WGQGTLVTVSS |
| 55 | 30A10 LC VARIABLE | DIQMTQSPSSLSASVGDRVTISCRASQNIINFLNWYQQKPGKAPKVLIDAASS LRSGVPSRFSGSGSETDESLTISSLQPEDFATYYCQQSFSTPLTFGGGTKVEI R |
| 56 | 30A10 HC FULL LENGTH | MDMRVPAQLLGLLLLWLRGARCQVQLVESGGGVVQPGRSLRLSCAASGFTESS YAMHWVRQAPGKGLEWVAIIWFDGSQRYYADSVKGRFTISRDNSRDTLYLQMN SLRAEDTAVYYCARDELTGFDYWGQGTLVTVSSASTKGPSVFPLAPCSRSTSE STAALGCLVKDYFPEPVTVSWNSGALTSGVHTFPAVLQSSGLYSLSSVVTVPS SSLGTKTYTCNVDHKPSNTKVDKRVESKYGPPCPSCPAPEFLGGPSVFLFPPK PKDTLMISRTPEVTCVVVDVSQEDPEVQFNWYVDGVEVHNAKTKPREEQENST YRVVSVLTVLHQDWLNGKEYKCKVSNKGLPSSIEKTISKAKGQPREPQVYTLP PSQEEMTKNQVSLTCLVKGFYPSDIAVEWESNGQPENNYKTTPPVLDSDGSFF LYSRLTVDKSRWQEGNVFSCSVMHEALHNHYTQKSLSLSLGK |
| 57 | 30A10 LC FULL LENGTH | MDMRVPAQLLGLLLLWLRGARCDIQMTQSPSSLSASVGDRVTISCRASQNIIN FLNWYQQKPGKAPKVLIDAASSLRSGVPSRFSGSGSETDESLTISSLQPEDFA TYYCQQSFSTPLTFGGGTKVEIRRTVAAPSVFIFPPSDEQLKSGTASVVCLLN NFYPREAKVQWKVDNALQSGNSQESVTEQDSKDSTYSLSSTLTLSKADYEKHK VYACEVTHQGLSSPVTKSENRGEC |
| 46 | 30A10 Heavy chain constant region | same as SEQ ID NO: 46 ASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPC PSCPAPEFLGGPSVFLFPPKPKDTLMISRTPEVTCVVVDVSQEDPEVQFNWYV |

-continued

| | | |
|---|---|---|
| | SEQUENCES | |
| SEQ ID | Description | sequence |
| | | DGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALHNHYTQ<br>KSLSLSLGK |
| 30 | 30A10 light chain constant region | same as SEQ ID NO: 30<br>RTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSENRGE<br>C |
| 58 | 19D6 HC CDR1 | DYDMH |
| 59 | 19D6 HC CDR2 | AIDTAGDTYYLGPVKG |
| 60 | 19D6 HC CDR3 | DSGSSFDY |
| 61 | 19D6 LC CDR1 | QGDSLRNYYES |
| 62 | 19D6 LC CDR2 | GKNNRPS |
| 63 | 19D6 LC CDR3 | MSRDSSGNHWV |
| 64 | 19D6 HC VARIABLE | EVQLVESGGGLVQPGESLRLSCAASGFTFSDYDMHWVRQATGKGLEWVSAIDT<br>AGDTYYLGPVKGRFTISRENAKNSLFLHMNSLRVGDTAVYYCIRDSGSSFDYW<br>GQGTLVTVSS |
| 65 | 19D6 LC VARIABLE | TSELTQDPAVSVALGQTVRITCQGDSLRNYYESWYQQKPGQAPVLVIYGKNNR<br>PSGIPDRFSGSSSGNTASLIITGTQAEDEADYYCMSRDSSGNHWVFGGGTKVT<br>VL |
| 66 | 19D6 HC FULL LENGTH | MDMRVPAQLLGLLLLWLRGARCEVQLVESGGGLVQPGESLRLSCAASGFTFSD<br>YDMHWVRQATGKGLEWVSAIDTAGDTYYLGPVKGRFTISRENAKNSLFLHMNS<br>LRVGDTAVYYCIRDSGSSFDYWGQGTLVTVSSASTKGPSVFPLAPCSRSTSES<br>TAALGCLVKDYFPEPVTVSWNSGALTSGVHTFPAVLQSSGLYSLSSVVTVPSS<br>SLGTKTYTCNVDHKPSNTKVDKRVESKYGPPCPSCPAPEFLGGPSVFLFPPKP<br>KDTLMISRTPEVTCVVVDVSQEDPEVQFNWYVDGVEVHNAKTKPREEQFNSTY<br>RVVSVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGSFFL<br>YSRLTVDKSRWQEGNVFSCSVMHEALHNHYTQKSLSLSLGK |
| 67 | 19D6 LC FULL LENGTH | MDMRVPAQLLGLLLLWLRGARCTSELTQDPAVSVALGQTVRITCQGDSLRNYY<br>ESWYQQKPGQAPVLVIYGKNNRPSGIPDRESGSSSGNTASLIITGTQAEDEAD<br>YYCMSRDSSGNHWVFGGGTKVTVLGQPKAAPSVTLFPPSSEELQANKATLVCL<br>ISDFYPGAVTVAWKADSSPVKAGVETTTPSKQSNNKYAASSYLSLTPEQWKSH<br>RSYSCQVTHEGSTVEKTVAPTECS |
| 46 | 19D6 Heavy chain constant region | same as SEQ ID NO: 46<br>ASTKGPSVFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVESKYGPPC<br>PSCPAPEFLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALHNHYTQ<br>KSLSLSLGK |
| 47 | 19D6 light chain constant region | same as SEQ ID NO: 47<br>GQPKAAPSVTLFPPSSEELQANKATLVCLISDFYPGAVTVAWKADSSPVKAGV<br>ETTTPSKQSNNKYAASSYLSLTPEQWKSHRSYSCQVTHEGSTVEKTVAPTECS |
| 68 | Immunoglobulin heavy constant gamma 1 | ASTKGPSVFPLAPSSKSTSGGTAALGCLVKDYFPEPVTVSWNSGALTSGVHTF<br>PAVLQSSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNH<br>YTQKSLSLSPGK |
| 69 | Immunoglobulin heavy constant gamma 2 | ASTKGPSVFPLAPCSRSTSESTAALGCLVKDYFPEPVTVSWNSGALTSGVHTF<br>PAVLQSSGLYSLSSVVTVPSSNFGTQTYTCNVDHKPSNTKVDKTVERKCCVEC<br>PPCPAPPVAGPSVFLFPPKPKDTLMISRTPEVTCVVVDVSHEDPEVQFNWYVD<br>GVEVHNAKTKPREEQFNSTFRVVSVLTVVHQDWLNGKEYKCKVSNKGLPAPIE<br>KTISKTKGQPREPQVYTLPPSREEMTKNQVSLTCLVKGFYPSDISVEWESNGQ<br>PENNYKTTPPMLDSDGSFFLYSKLTVDKSRWQQGNVFSCSVMHEALHNHYTQK<br>SLSLSPGK |

-continued

| SEQUENCES | | |
|---|---|---|
| SEQ ID | Description | sequence |
| 70 | Immunoglobulin heavy constant gamma 3 | ASTKGPSVFPLAPCSRSTSGGTAALGCLVKDYFPEPVTVSWNSGALTSGVHTF PAVLQSSGLYSLSSVVTVPSSSLGTQTYTCNVNHKPSNTKVDKRVELKTPLGD TTHTCPRCPEPKSCDTPPPCPRCPEPKSCDTPPPCPRCPEPKSCDTPPPCPRC PAPELLGGPSVFLFPPKPKDTLMISRTPEVTCVVVDVSHEDPEVQFKWYVDGV EVHNAKTKPREEQYNSTFRVVSVLTVLHQDWLNGKEYKCKVSNKALPAPIEKT ISKTKGQPREPQVYTLPPSREEMTKNQVSLTCLVKGFYPSDIAVEWESSGQPE NNYNTTPPMLDSDGSFFLYSKLTVDKSRWQQGNIFSCSVMHEALHNRFTQKSL SLSPGK |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A method for increasing Interferon-gamma (IFN-γ) expression level in a subject that has cancer, as compared to a control, comprising administering to the subject a therapeutically effective amount of (i) a first antibody, or antigen-binding fragment thereof, that binds Programmed death-1 (PD-1) or Programmed death-ligand 1 (PD-L1); and (ii) a second antibody, or antigen-binding fragment thereof, that binds leukocyte immunoglobulin-like receptor B1 (LILRB1), wherein said first antibody, or antigen-binding fragment thereof is selected from the group consisting of: pembrolizumab, nivolumab, atezolizumab, durvalumab, avelumab, anti-PD1 antibody clone 20C1, and an antigen-binding fragment of any of the foregoing; and wherein said second antibody, or antigen-binding fragment thereof, binds LILRB1 and comprises:

(i) a heavy chain variable region (VH) that comprises: a CDR-H1 comprising the amino acid sequence of SEQ ID NO: 36, a CDR-H2 comprising the amino acid sequence of SEQ ID NO: 37; and a CDR-H3 comprising the amino acid sequence of SEQ ID NO: 38; and a light chain variable region (VL) that comprises: a CDR-L1 comprising the amino acid sequence of SEQ ID NO: 39, a CDR-L2 comprising the amino acid sequence of SEQ ID NO: 40; and a CDR-L3 comprising the amino acid sequence of SEQ ID NO: 41; or (ii) a heavy chain variable region (VH) that comprises: a CDR-H1 comprising the amino acid sequence of SEQ ID NO: 48, a CDR-H2 comprising the amino acid sequence of SEQ ID NO: 49; and a CDR-H3 comprising the amino acid sequence of SEQ ID NO: 50; and a light chain variable region (VL) that comprises: a CDR-L1 comprising the amino acid sequence of SEQ ID NO: 51, a CDR-L2 comprising the amino acid sequence of SEQ ID NO: 52; and a CDR-L3 comprising the amino acid sequence of SEQ ID NO: 53; or (iii) a heavy chain variable region (VH) that comprises: a CDR-H1 comprising the amino acid sequence of SEQ ID NO: 58, a CDR-H2 comprising the amino acid sequence of SEQ ID NO: 59; and a CDR-H3 comprising the amino acid sequence of SEQ ID NO: 60; and a light chain variable region (VL) that comprises: a CDR-L1 comprising the amino acid sequence of SEQ ID NO: 61, a CDR-L2 comprising the amino acid sequence of SEQ ID NO: 62; and a CDR-L3 comprising the amino acid sequence of SEQ ID NO: 63.

2. The method of claim 1, wherein said first antibody, or antigen-binding fragment thereof, binds PD-1 and comprises:

a heavy chain variable region (VH) that comprises: a CDR-H1 comprising the amino acid sequence of SEQ ID NO: 19, a CDR-H2 comprising the amino acid sequence of SEQ ID NO: 20; and a CDR-H3 comprising the amino acid sequence of SEQ ID NO: 21; and a light chain variable region (VL) that comprises: CDR-L1 comprising the amino acid sequence of SEQ ID NO: 22, a CDR-L2 comprising the amino acid sequence of SEQ ID NO: 23; and a CDR-L3 comprising the amino acid sequence of SEQ ID NO: 24.

3. A method for increasing CD8+ T-cell mediated cytotoxicity in a subject that has cancer, as compared to a control, comprising administering to the subject a therapeutically effective amount of (i) a first antibody, or antigen-binding fragment thereof, that binds PD-1 or PD-L1; and (ii) a second antibody, or antigen-binding fragment thereof, that binds LILRB1, wherein said first antibody, or antigen-binding fragment thereof is selected from the group consisting of: pembrolizumab, nivolumab, atezolizumab, durvalumab, avelumab, anti-PD1 antibody clone 20C1, and an antigen-binding fragment of any of the foregoing; and wherein said second antibody, or antigen-binding fragment thereof, binds LILRB1 and comprises:

(i) a heavy chain variable region (VH) that comprises: a CDR-H1 comprising the amino acid sequence of SEQ ID NO: 36, a CDR-H2 comprising the amino acid sequence of SEQ ID NO: 37; and a CDR-H3 comprising the amino acid sequence of SEQ ID NO: 38; and a light chain variable region (VL) that comprises: a CDR-L1 comprising the amino acid sequence of SEQ ID NO: 39, a CDR-L2 comprising the amino acid sequence of SEQ ID NO: 40; and a CDR-L3 comprising the amino acid sequence of SEQ ID NO: 41; or (ii) a heavy chain variable region (VH) that comprises: a CDR-H1 comprising the amino acid sequence of SEQ ID NO: 48, a CDR-H2 comprising the amino acid sequence of SEQ ID NO: 49; and a CDR-H3 comprising the amino acid sequence of SEQ ID NO: 50; and a light chain variable region (VL) that comprises: a CDR-L1 comprising the amino acid sequence of SEQ ID NO: 51, a CDR-L2 comprising the amino acid sequence of SEQ ID NO: 52; and a CDR-L3 comprising the amino acid sequence of SEQ ID NO: 53; or (iii) a heavy chain variable region (VH) that comprises: a CDR-H1 comprising the amino acid sequence of SEQ ID NO: 58, a CDR-H2 comprising the amino acid sequence of SEQ ID NO: 59; and a CDR-H3 comprising the amino acid sequence of SEQ ID NO: 60; and a light chain variable region (VL) that comprises: a CDR-L1 comprising the amino acid sequence of SEQ ID NO: 61, a CDR-L2 comprising the amino acid sequence of SEQ ID NO: 62; and a CDR-L3 comprising the amino acid sequence of SEQ ID NO: 63.

4. The method of claim 3, wherein said first antibody, or antigen-binding fragment thereof, binds PD-1 and comprises:

a heavy chain variable region (VH) that comprises: a CDR-H1 comprising the amino acid sequence of SEQ ID NO: 19, a CDR-H2 comprising the amino acid sequence of SEQ ID NO: 20; and a CDR-H3 comprising the amino acid sequence of SEQ ID NO: 21; and a light chain variable region (VL) that comprises: CDR-L1 comprising the amino acid sequence of SEQ ID NO: 22, a CDR-L2 comprising the amino acid sequence of SEQ ID NO: 23; and a CDR-L3 comprising the amino acid sequence of SEQ ID NO: 24.

5. A method for treating a subject that has a tumor, wherein said subject is refractory to treatment with an anti-PD-1 antibody or antigen-binding fragment thereof, or an anti-PD-L1 antibody or antigen-binding fragment thereof, comprising:

administering to the subject a therapeutically effective amount of (i) a first antibody, or antigen-binding fragment thereof, that binds PD-1 or PD-L1; and (ii) a second antibody, or antigen-binding fragment thereof, that binds LILRB1, wherein said first antibody, or antigen-binding fragment thereof is selected from the group consisting of: pembrolizumab, nivolumab, atezolizumab, durvalumab, avelumab, anti-PD1 antibody clone 20C1, and an antigen-binding fragment of any of the foregoing; and wherein said second antibody, or antigen-binding fragment thereof, binds LILRB1 and comprises:

(i) a heavy chain variable region (VH) that comprises: a CDR-H1 comprising the amino acid sequence of SEQ ID NO: 36, a CDR-H2 comprising the amino acid sequence of SEQ ID NO: 37; and a CDR-H3 comprising the amino acid sequence of SEQ ID NO: 38; and a light chain variable region (VL) that comprises: a CDR-L1 comprising the amino acid sequence of SEQ ID NO: 39, a CDR-L2 comprising the amino acid sequence of SEQ ID NO: 40; and a CDR-L3 comprising the amino acid sequence of SEQ ID NO: 41; or (ii) a heavy chain variable region (VH) that comprises: a CDR-H1 comprising the amino acid sequence of SEQ ID NO: 48, a CDR-H2 comprising the amino acid sequence of SEQ ID NO: 49; and a CDR-H3 comprising the amino acid sequence of SEQ ID NO: 50; and a light chain variable region (VL) that comprises: a CDR-L1 comprising the amino acid sequence of SEQ ID NO: 51, a CDR-L2 comprising the amino acid sequence of SEQ ID NO: 52; and a CDR-L3 comprising the amino acid sequence of SEQ ID NO: 53; or (iii) a heavy chain variable region (VH) that comprises: a CDR-H1 comprising the amino acid sequence of SEQ ID NO: 58, a CDR-H2 comprising the amino acid sequence of SEQ ID NO: 59; and a CDR-H3 comprising the amino acid sequence of SEQ ID NO: 60; and a light chain variable region (VL) that comprises: a CDR-L1 comprising the amino acid sequence of SEQ ID NO: 61, a CDR-L2 comprising the amino acid sequence of SEQ ID NO: 62; and a CDR-L3 comprising the amino acid sequence of SEQ ID NO: 63.

6. The method of claim 5, wherein said first antibody, or antigen-binding fragment thereof, binds PD-1 and comprises:

a heavy chain variable region (VH) that comprises: a CDR-H1 comprising the amino acid sequence of SEQ ID NO: 19, a CDR-H2 comprising the amino acid sequence of SEQ ID NO: 20; and a CDR-H3 comprising the amino acid sequence of SEQ ID NO: 21; and a light chain variable region (VL) that comprises: CDR-L1 comprising the amino acid sequence of SEQ ID NO: 22, a CDR-L2 comprising the amino acid sequence of SEQ ID NO: 23; and a CDR-L3 comprising the amino acid sequence of SEQ ID NO: 24.

7. The method of claim 1, wherein said second antibody, or antigen-binding fragment thereof, binds LILRB1 and comprises:

(i) a heavy chain variable region (VH) that comprises the amino acid sequence of SEQ ID NO: 42; and a light chain variable region (VL) that comprises the amino acid sequence of SEQ ID NO: 43; or (ii) a heavy chain variable region (VH) that comprises the amino acid sequence of SEQ ID NO: 54; and a light chain variable region (VL) that comprises the amino acid sequence of SEQ ID NO: 55; or (iii) a heavy chain variable region (VH) that comprises the amino acid sequence of SEQ ID NO: 64; and a light chain variable region (VL) that comprises the amino acid sequence of SEQ ID NO: 65.

8. The method of claim 1, wherein said second antibody, or antigen-binding fragment thereof, binds LILRB1 and further comprises a human immunoglobulin G (IgG) heavy chain constant region.

9. The method of claim 8, wherein said human IgG is IgG1, IgG2, or IgG4.

10. The method of claim 1, wherein said second antibody, or antigen-binding fragment thereof, binds LILRB1 and further comprises a human immunoglobulin kappa or lambda constant domain region.

11. The method of claim 1, wherein said second antibody, or antigen-binding fragment thereof, binds LILRB1 and further comprises a heavy chain constant domain comprising the amino acid sequence of any of SEQ ID NOs: 46 and 68-70, and a light chain constant domain comprising the amino acid sequence of SEQ ID NO: 30 or SEQ ID NO: 47.

12. The method of claim 3, wherein said second antibody, or antigen-binding fragment thereof, binds LILRB1 and comprises:

(i) a heavy chain variable region (VH) that comprises the amino acid sequence of SEQ ID NO: 42; and a light chain variable region (VL) that comprises the amino acid sequence of SEQ ID NO: 43; or (ii) a heavy chain variable region (VH) that comprises the amino acid sequence of SEQ ID NO: 54; and a light chain variable region (VL) that comprises the amino acid sequence of SEQ ID NO: 55; or (iii) a heavy chain variable region (VH) that comprises the amino acid sequence of SEQ ID NO: 64; and a light chain variable region (VL) that comprises the amino acid sequence of SEQ ID NO: 65.

13. The method of claim 3, wherein said second antibody, or antigen-binding fragment thereof, binds LILRB1 and further comprises a human immunoglobulin G (IgG) heavy chain constant region.

14. The method of claim 13, wherein said human IgG is IgG1, IgG2, or IgG4.

15. The method of claim 3, wherein said second antibody, or antigen-binding fragment thereof, binds LILRB1 and further comprises a human immunoglobulin kappa or lambda constant domain region.

16. The method of claim 3, wherein said second antibody, or antigen-binding fragment thereof, binds LILRB1 and further comprises a heavy chain constant domain comprising the amino acid sequence of any of SEQ ID NOs: 46 and 68-70, and a light chain constant domain comprising the amino acid sequence of SEQ ID NO: 30 or SEQ ID NO: 47.

17. The method of claim 5, wherein said second antibody, or antigen-binding fragment thereof, binds LILRB1 and comprises:

(i) a heavy chain variable region (VH) that comprises the amino acid sequence of SEQ ID NO: 42; and a light chain variable region (VL) that comprises the amino acid sequence of SEQ ID NO: 43; or (ii) a heavy chain variable region (VH) that comprises the amino acid sequence of SEQ ID NO: 54; and a light chain variable region (VL) that comprises the amino acid sequence of SEQ ID NO: 55; or (iii) a heavy chain variable region (VH) that comprises the amino acid sequence of SEQ ID NO: 64; and a light chain variable region (VL) that comprises the amino acid sequence of SEQ ID NO: 65.

18. The method of claim 5, wherein said second antibody, or antigen-binding fragment thereof, binds LILRB1 and further comprises a human immunoglobulin G (IgG) heavy chain constant region.

19. The method of claim 18, wherein said human IgG is IgG1, IgG2, or IgG4.

20. The method of claim 5, wherein said second antibody, or antigen-binding fragment thereof, binds LILRB1 and further comprises a human immunoglobulin kappa or lambda constant domain region.

21. The method of claim 5, wherein said second antibody, or antigen-binding fragment thereof, binds LILRB1 and further comprises a heavy chain constant domain comprising the amino acid sequence of any of SEQ ID NOs: 46 and 68-70, and a light chain constant domain comprising the amino acid sequence of SEQ ID NO: 30 or SEQ ID NO: 47.

22. The method of claim 1, wherein said first antibody, or antigen-binding fragment thereof is selected from the group consisting of: pembrolizumab, nivolumab, atezolizumab, durvalumab, avelumab, and an antigen-binding fragment of any of the foregoing.

23. The method of claim 1, wherein said first antibody is selected from the group consisting of: pembrolizumab, nivolumab, atezolizumab, durvalumab, and avelumab.

24. The method of claim 3, wherein said first antibody, or antigen-binding fragment thereof is selected from the group consisting of: pembrolizumab, nivolumab, atezolizumab, durvalumab, avelumab, and an antigen-binding fragment of any of the foregoing.

25. The method of claim 3, wherein said first antibody is selected from the group consisting of: pembrolizumab, nivolumab, atezolizumab, durvalumab, and avelumab.

26. The method of claim 5, wherein said first antibody, or antigen-binding fragment thereof is selected from the group consisting of: pembrolizumab, nivolumab, atezolizumab, durvalumab, avelumab, and an antigen-binding fragment of any of the foregoing.

27. The method of claim 5, wherein said first antibody is selected from the group consisting of: pembrolizumab, nivolumab, atezolizumab, durvalumab, and avelumab.

* * * * *

SEQUENCE LISTING

<160> NUMBER OF SEQ ID NOS: 70

<210> SEQ ID NO 1
<211> LENGTH: 288
<212> TYPE: PRT
<213> ORGANISM: Homo sapiens

<400> SEQUENCE: 1

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190
```

-continued

```
Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
        275                 280                 285

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
        275                 280                 285
```

-continued

```
Glu Thr
    290

<210> SEQ ID NO 3
<211> LENGTH: 650
<212> TYPE: PRT
<213> ORGANISM: Homo sapiens

<400> SEQUENCE: 3

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Ile Leu Gln
        130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
            165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
            195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
            245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
            325                 330                 335

Ala Ser Gly Glu Asn Val Thr Leu Leu Cys Gln Ser Gln Gly Trp Met
        340                 345                 350

Gln Thr Phe Leu Leu Thr Lys Glu Gly Ala Ala Asp Asp Pro Trp Arg
```

-continued

```
             355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
                420                 425                 430

Pro Thr Ser Thr Ser Gly Pro Glu Asp Gln Pro Leu Thr Pro Thr Gly
                435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
                580                 585                 590

Ala Glu Glu Asp Arg Gln Met Asp Thr Glu Ala Ala Ala Ser Glu Ala
                595                 600                 605

Pro Gln Asp Val Thr Tyr Ala Gln Leu His Ser Leu Thr Leu Arg Arg
                610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650

<210> SEQ ID NO 4
<211> LENGTH: 651
<212> TYPE: PRT
<213> ORGANISM: Homo sapiens

<400> SEQUENCE: 4

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
                35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80
```

```
Gly Gln Phe Pro Ile Pro Ser Ile Thr Trp Glu His Ala Gly Arg Tyr
                85              90                  95

Arg Cys Tyr Tyr Gly Ser Asp Thr Ala Gly Arg Ser Glu Ser Ser Asp
                100             105             110

Pro Leu Glu Leu Val Val Thr Gly Ala Tyr Ile Lys Pro Thr Leu Ser
                115             120             125

Ala Gln Pro Ser Pro Val Val Asn Ser Gly Gly Asn Val Ile Leu Gln
    130             135             140

Cys Asp Ser Gln Val Ala Phe Asp Gly Phe Ser Leu Cys Lys Glu Gly
145             150             155             160

Glu Asp Glu His Pro Gln Cys Leu Asn Ser Gln Pro His Ala Arg Gly
                165             170             175

Ser Ser Arg Ala Ile Phe Ser Val Gly Pro Val Ser Pro Ser Arg Arg
                180             185             190

Trp Trp Tyr Arg Cys Tyr Ala Tyr Asp Ser Asn Ser Pro Tyr Glu Trp
                195             200             205

Ser Leu Pro Ser Asp Leu Leu Glu Leu Leu Val Leu Gly Val Ser Lys
    210             215             220

Lys Pro Ser Leu Ser Val Gln Pro Gly Pro Ile Val Ala Pro Glu Glu
225             230             235             240

Thr Leu Thr Leu Gln Cys Gly Ser Asp Ala Gly Tyr Asn Arg Phe Val
                245             250             255

Leu Tyr Lys Asp Gly Glu Arg Asp Phe Leu Gln Leu Ala Gly Ala Gln
                260             265             270

Pro Gln Ala Gly Leu Ser Gln Ala Asn Phe Thr Leu Gly Pro Val Ser
    275             280             285

Arg Ser Tyr Gly Gly Gln Tyr Arg Cys Tyr Gly Ala His Asn Leu Ser
    290             295             300

Ser Glu Trp Ser Ala Pro Ser Asp Pro Leu Asp Ile Leu Ile Ala Gly
305             310             315             320

Gln Phe Tyr Asp Arg Val Ser Leu Ser Val Gln Pro Gly Pro Thr Val
                325             330             335

Ala Ser Gly Glu Asn Val Thr Leu Leu Cys Gln Ser Gln Gly Trp Met
                340             345             350

Gln Thr Phe Leu Leu Thr Lys Glu Gly Ala Ala Asp Asp Pro Trp Arg
    355             360             365

Leu Arg Ser Thr Tyr Gln Ser Gln Lys Tyr Gln Ala Glu Phe Pro Met
    370             375             380

Gly Pro Val Thr Ser Ala His Ala Gly Thr Tyr Arg Cys Tyr Gly Ser
385             390             395             400

Gln Ser Ser Lys Pro Tyr Leu Leu Thr His Pro Ser Asp Pro Leu Glu
                405             410             415

Leu Val Val Ser Gly Pro Ser Gly Gly Pro Ser Ser Pro Thr Thr Gly
                420             425             430

Pro Thr Ser Thr Ser Ala Gly Pro Glu Asp Gln Pro Leu Thr Pro Thr
                435             440             445

Gly Ser Asp Pro Gln Ser Gly Leu Gly Arg His Leu Gly Val Val Ile
    450             455             460

Gly Ile Leu Val Ala Val Ile Leu Leu Leu Leu Leu Leu Leu Leu Leu
465             470             475             480

Phe Leu Ile Leu Arg His Arg Arg Gln Gly Lys His Trp Thr Ser Thr
                485             490             495

Gln Arg Lys Ala Asp Phe Gln His Pro Ala Gly Ala Val Gly Pro Glu
```

-continued

```
                500                 505                 510

Pro Thr Asp Arg Gly Leu Gln Trp Arg Ser Ser Pro Ala Ala Asp Ala
        515                 520                 525

Gln Glu Glu Asn Leu Tyr Ala Ala Val Lys His Thr Gln Pro Glu Asp
        530                 535                 540

Gly Val Glu Met Asp Thr Arg Ser Pro His Asp Glu Asp Pro Gln Ala
545                 550                 555                 560

Val Thr Tyr Ala Glu Val Lys His Ser Arg Pro Arg Arg Glu Met Ala
                565                 570                 575

Ser Pro Pro Ser Pro Leu Ser Gly Glu Phe Leu Asp Thr Lys Asp Arg
                580                 585                 590

Gln Ala Glu Glu Asp Arg Gln Met Asp Thr Glu Ala Ala Ala Ser Glu
        595                 600                 605

Ala Pro Gln Asp Val Thr Tyr Ala Gln Leu His Ser Leu Thr Leu Arg
        610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 5
<211> LENGTH: 652
<212> TYPE: PRT
<213> ORGANISM: Homo sapiens

<400> SEQUENCE: 5

Met Thr Pro Ile Leu Thr Val Leu Ile Cys Leu Gly Leu Ser Leu Gly
1                   5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
                100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
        130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
                180                 185                 190

Trp Trp Tyr Arg Cys Tyr Ala Tyr Asp Ser Asn Ser Pro Tyr Glu Trp
                195                 200                 205

Ser Leu Pro Ser Asp Leu Leu Glu Leu Leu Val Leu Gly Val Ser Lys
        210                 215                 220
```

```
Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
        290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
        370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Ala Gly Pro Glu Asp Gln Pro Leu Thr Pro Thr
            435                 440                 445

Gly Ser Asp Pro Gln Ser Gly Leu Gly Arg His Leu Gly Val Val Ile
        450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
            500                 505                 510

Pro Thr Asp Arg Gly Leu Gln Trp Arg Ser Ser Pro Ala Ala Asp Ala
            515                 520                 525

Gln Glu Glu Asn Leu Tyr Ala Ala Val Lys His Thr Gln Pro Glu Asp
        530                 535                 540

Gly Val Glu Met Asp Thr Arg Gln Ser Pro His Asp Glu Asp Pro Gln
545                 550                 555                 560

Ala Val Thr Tyr Ala Glu Val Lys His Ser Arg Pro Arg Arg Glu Met
                565                 570                 575

Ala Ser Pro Pro Ser Pro Leu Ser Gly Glu Phe Leu Asp Thr Lys Asp
            580                 585                 590

Arg Gln Ala Glu Glu Asp Arg Gln Met Asp Thr Glu Ala Ala Ala Ser
        595                 600                 605

Glu Ala Pro Gln Asp Val Thr Tyr Ala Gln Leu His Ser Leu Thr Leu
        610                 615                 620

Arg Arg Glu Ala Thr Glu Pro Pro Pro Ser Gln Glu Gly Pro Ser Pro
625                 630                 635                 640

Ala Val Pro Ser Ile Tyr Ala Thr Leu Ala Ile His
```

-continued

```
                  645                 650

<210> SEQ ID NO 6
<211> LENGTH: 651
<212> TYPE: PRT
<213> ORGANISM: Homo sapiens

<400> SEQUENCE: 6

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Ile Leu Gln
        130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
            195                 200                 205

Ser Leu Pro Ser Asp Leu Leu Glu Leu Leu Val Leu Gly Val Ser Lys
        210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
        290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
            325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365
```

-continued

```
Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
                420                 425                 430

Pro Thr Ser Thr Ser Gly Pro Glu Asp Gln Pro Leu Thr Pro Thr Gly
                435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys His Thr Gln Pro Glu Asp Gly
    530                 535                 540

Val Glu Met Asp Thr Arg Gln Ser Pro His Asp Glu Asp Pro Gln Ala
545                 550                 555                 560

Val Thr Tyr Ala Glu Val Lys His Ser Arg Pro Arg Arg Glu Met Ala
                565                 570                 575

Ser Pro Pro Ser Pro Leu Ser Gly Glu Phe Leu Asp Thr Lys Asp Arg
                580                 585                 590

Gln Ala Glu Glu Asp Arg Gln Met Asp Thr Glu Ala Ala Ala Ser Glu
                595                 600                 605

Ala Pro Gln Asp Val Thr Tyr Ala Gln Leu His Ser Leu Thr Leu Arg
                610                 615                 620

Arg Glu Ala Thr Glu Pro Pro Pro Ser Gln Glu Gly Pro Ser Pro Ala
625                 630                 635                 640

Val Pro Ser Ile Tyr Ala Thr Leu Ala Ile His
                645                 650

<210> SEQ ID NO 7
<211> LENGTH: 456
<212> TYPE: PRT
<213> ORGANISM: Homo sapiens

<400> SEQUENCE: 7

Met Thr Pro Ile Leu Thr Val Leu Ile Cys Leu Gly Leu Ser Leu Gly
1                   5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95
```

-continued

```
Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
            115                 120                 125

Ala Gln Pro Ser Pro Val Val Asn Ser Gly Gly Asn Val Ile Leu Gln
            130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
                180                 185                 190

Trp Trp Tyr Arg Cys Tyr Ala Tyr Asp Ser Asn Ser Pro Tyr Glu Trp
                195                 200                 205

Ser Leu Pro Ser Asp Leu Leu Glu Leu Leu Val Leu Gly Val Ser Lys
            210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
            275                 280                 285

Arg Ser Tyr Gly Gly Gln Tyr Arg Cys Tyr Gly Ala His Asn Leu Ser
            290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
            355                 360                 365

Leu Arg Ser Thr Tyr Gln Ser Gln Lys Tyr Gln Ala Glu Phe Pro Met
            370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
                420                 425                 430

Pro Thr Ser Thr Ser Ala Gly Pro Glu Asp Gln Pro Leu Thr Pro Thr
            435                 440                 445

Gly Ser Asp Pro Gln Ser Gly Glu
            450                 455

<210> SEQ ID NO 8
<211> LENGTH: 598
<212> TYPE: PRT
<213> ORGANISM: Homo sapiens

<400> SEQUENCE: 8

Met Thr Pro Ile Val Thr Val Leu Ile Cys Leu Gly Leu Ser Leu Gly
```

-continued

```
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
            50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
                100                 105                 110

Leu Val Leu Val Met Thr Gly Ala Tyr Pro Lys Pro Thr Leu Ser Ala
                115                 120                 125

Gln Pro Ser Pro Val Val Thr Ser Gly Gly Arg Val Thr Leu Gln Cys
            130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
                180                 185                 190

Ser His Arg Cys Tyr Gly Tyr Asp Leu Asn Ser Pro Tyr Val Trp Ser
            195                 200                 205

Ser Pro Ser Asp Leu Leu Glu Leu Leu Val Pro Gly Val Ser Lys Lys
            210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
                260                 265                 270

Gln Ala Gly Leu Ser Gln Ala Asn Phe Thr Leu Gly Pro Val Ser Arg
            275                 280                 285

Ser Tyr Gly Gly Gln Tyr Arg Cys Tyr Gly Ala His Asn Leu Ser Ser
            290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
            370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Pro Thr Gly Pro
            420                 425                 430
```

-continued

```
Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
                580                 585                 590

Ala Thr Leu Ala Ile His
        595
```

```
<210> SEQ ID NO 9
<211> LENGTH: 597
<212> TYPE: PRT
<213> ORGANISM: Homo sapiens

<400> SEQUENCE: 9

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
                100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
        130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
                180                 185                 190

Ser His Arg Cys Tyr Gly Tyr Asp Leu Asn Ser Pro Tyr Val Trp Ser
```

```
            195                    200                    205
Ser Pro Ser Asp Leu Leu Glu Leu Leu Val Pro Gly Val Ser Lys Lys
    210                    215                    220

Pro Ser Leu Ser Val Gln Pro Gly Pro Val Val Ala Pro Gly Glu Ser
225                    230                    235                    240

Leu Thr Leu Gln Cys Val Ser Asp Val Gly Tyr Asp Arg Phe Val Leu
                245                    250                    255

Tyr Lys Glu Gly Glu Arg Asp Leu Arg Gln Leu Pro Gly Arg Gln Pro
                260                    265                    270

Gln Ala Gly Leu Ser Gln Ala Asn Phe Thr Leu Gly Pro Val Ser Arg
                275                    280                    285

Ser Tyr Gly Gly Gln Tyr Arg Cys Tyr Gly Ala His Asn Leu Ser Ser
    290                    295                    300

Glu Cys Ser Ala Pro Ser Asp Pro Leu Asp Ile Leu Ile Thr Gly Gln
305                    310                    315                    320

Ile Arg Gly Thr Pro Phe Ile Ser Val Gln Pro Gly Pro Thr Val Ala
                325                    330                    335

Ser Gly Glu Asn Val Thr Leu Leu Cys Gln Ser Trp Arg Gln Phe His
                340                    345                    350

Thr Phe Leu Leu Thr Lys Ala Gly Ala Ala Asp Ala Pro Leu Arg Leu
                355                    360                    365

Arg Ser Ile His Glu Tyr Pro Lys Tyr Gln Ala Glu Phe Pro Met Ser
    370                    375                    380

Pro Val Thr Ser Ala His Ala Gly Thr Tyr Arg Cys Tyr Gly Ser Leu
385                    390                    395                    400

Asn Ser Asp Pro Tyr Leu Leu Ser His Pro Ser Glu Pro Leu Glu Leu
                405                    410                    415

Val Val Ser Gly Pro Ser Met Gly Ser Ser Pro Pro Pro Thr Gly Pro
                420                    425                    430

Ile Ser Thr Pro Gly Pro Glu Asp Gln Pro Leu Thr Pro Thr Gly Ser
                435                    440                    445

Asp Pro Gln Ser Gly Leu Gly Arg His Leu Gly Val Val Ile Gly Ile
    450                    455                    460

Leu Val Ala Val Val Leu Leu Leu Leu Leu Leu Leu Leu Phe Leu
465                    470                    475                    480

Ile Leu Arg His Arg Arg Gln Gly Lys His Trp Thr Ser Thr Gln Arg
                485                    490                    495

Lys Ala Asp Phe Gln His Pro Ala Gly Ala Val Gly Pro Glu Pro Thr
                500                    505                    510

Asp Arg Gly Leu Gln Trp Arg Ser Ser Pro Ala Ala Asp Ala Gln Glu
                515                    520                    525

Glu Asn Leu Tyr Ala Ala Val Lys Asp Thr Gln Pro Glu Asp Gly Val
    530                    535                    540

Glu Met Asp Thr Arg Ala Ala Ala Ser Glu Ala Pro Gln Asp Val Thr
545                    550                    555                    560

Tyr Ala Gln Leu His Ser Leu Thr Leu Arg Arg Lys Ala Thr Glu Pro
                565                    570                    575

Pro Pro Ser Gln Glu Arg Glu Pro Pro Ala Glu Pro Ser Ile Tyr Ala
                580                    585                    590

Thr Leu Ala Ile His
            595
```

<210> SEQ ID NO 10

```
<211> LENGTH: 510
<212> TYPE: PRT
<213> ORGANISM: Homo sapiens

<400> SEQUENCE: 10

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
        130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
        210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
        290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
        370                 375                 380

Pro Val Thr Ser Ala His Ala Gly Thr Tyr Arg Cys Tyr Gly Ser Leu
```

-continued

```
385             390             395             400

Asn Ser Asp Pro Tyr Leu Leu Ser His Pro Ser Glu Pro Leu Glu Leu
            405             410             415

Val Val Ser Gly Pro Ser Met Gly Ser Ser Pro Pro Pro Thr Gly Pro
            420             425             430

Ile Ser Thr Pro Ala Gly Pro Glu Asp Gln Pro Leu Thr Pro Thr Gly
            435             440             445

Ser Asp Pro Gln Ser Gly Leu Gly Arg His Leu Gly Val Val Ile Gly
    450             455             460

Ile Leu Val Ala Val Val Leu Leu Leu Leu Leu Leu Leu Leu Leu Phe
465             470             475             480

Leu Ile Leu Arg His Arg Arg Gln Gly Lys His Trp Thr Ser Ser Pro
            485             490             495

Ala Gln Leu Pro Thr Pro Arg Lys Lys Thr Ser Met Leu Pro
            500             505             510

<210> SEQ ID NO 11
<211> LENGTH: 482
<212> TYPE: PRT
<213> ORGANISM: Homo sapiens

<400> SEQUENCE: 11

Met Thr Gly Ala Tyr Pro Lys Pro Thr Leu Ser Ala Gln Pro Ser Pro
1               5               10              15

Val Val Thr Ser Gly Gly Arg Val Thr Leu Gln Cys Glu Ser Gln Val
            20              25              30

Ala Phe Gly Gly Phe Ile Leu Cys Lys Glu Gly Glu Glu Glu His Pro
            35              40              45

Gln Cys Leu Asn Ser Gln Pro His Ala Arg Gly Ser Ser Arg Ala Ile
    50              55              60

Phe Ser Val Gly Pro Val Ser Pro Asn Arg Arg Trp Ser His Arg Cys
65              70              75              80

Tyr Gly Tyr Asp Leu Asn Ser Pro Tyr Val Trp Ser Ser Pro Ser Asp
            85              90              95

Leu Leu Glu Leu Leu Val Pro Gly Val Ser Lys Lys Pro Ser Leu Ser
            100             105             110

Val Gln Pro Gly Pro Val Val Ala Pro Gly Glu Ser Leu Thr Leu Gln
            115             120             125

Cys Val Ser Asp Val Gly Tyr Asp Arg Phe Val Leu Tyr Lys Glu Gly
    130             135             140

Glu Arg Asp Leu Arg Gln Leu Pro Gly Arg Gln Pro Gln Ala Gly Leu
145             150             155             160

Ser Gln Ala Asn Phe Thr Leu Gly Pro Val Ser Arg Ser Tyr Gly Gly
            165             170             175

Gln Tyr Arg Cys Tyr Gly Ala His Asn Leu Ser Ser Glu Cys Ser Ala
            180             185             190

Pro Ser Asp Pro Leu Asp Ile Leu Ile Thr Gly Gln Ile Arg Gly Thr
            195             200             205

Pro Phe Ile Ser Val Gln Pro Gly Pro Thr Val Ala Ser Gly Glu Asn
    210             215             220

Val Thr Leu Leu Cys Gln Ser Trp Arg Gln Phe His Thr Phe Leu Leu
225             230             235             240

Thr Lys Ala Gly Ala Ala Asp Ala Pro Leu Arg Leu Arg Ser Ile His
            245             250             255
```

-continued

```
Glu Tyr Pro Lys Tyr Gln Ala Glu Phe Pro Met Ser Pro Val Thr Ser
            260             265             270

Ala His Ala Gly Thr Tyr Arg Cys Tyr Gly Ser Leu Asn Ser Asp Pro
            275             280             285

Tyr Leu Leu Ser His Pro Ser Glu Pro Leu Glu Leu Val Val Ser Gly
    290             295             300

Pro Ser Met Gly Ser Ser Pro Pro Pro Thr Gly Pro Ile Ser Thr Pro
305             310             315             320

Ala Gly Pro Glu Asp Gln Pro Leu Thr Pro Thr Gly Ser Asp Pro Gln
            325             330             335

Ser Gly Leu Gly Arg His Leu Gly Val Val Ile Gly Ile Leu Val Ala
            340             345             350

Val Val Leu Leu Leu Leu Leu Leu Leu Leu Leu Phe Leu Ile Leu Arg
            355             360             365

His Arg Arg Gln Gly Lys His Trp Thr Ser Thr Gln Arg Lys Ala Asp
            370             375             380

Phe Gln His Pro Ala Gly Ala Val Gly Pro Glu Pro Thr Asp Arg Gly
385             390             395             400

Leu Gln Trp Arg Ser Ser Pro Ala Ala Asp Ala Gln Glu Glu Asn Leu
                405             410             415

Tyr Ala Ala Val Lys Asp Thr Gln Pro Glu Asp Gly Val Glu Met Asp
            420             425             430

Thr Arg Ala Ala Ala Ser Glu Ala Pro Gln Asp Val Thr Tyr Ala Gln
            435             440             445

Leu His Ser Leu Thr Leu Arg Arg Lys Ala Thr Glu Pro Pro Pro Ser
    450             455             460

Gln Glu Arg Glu Pro Pro Ala Glu Pro Ser Ile Tyr Ala Thr Leu Ala
465             470             475             480

Ile His
```

```
<210> SEQ ID NO 12
<211> LENGTH: 338
<212> TYPE: PRT
<213> ORGANISM: Homo sapiens

<400> SEQUENCE: 12

Met Val Val Met Ala Pro Arg Thr Leu Phe Leu Leu Leu Ser Gly Ala
1               5               10              15

Leu Thr Leu Thr Glu Thr Trp Ala Gly Ser His Ser Met Arg Tyr Phe
            20              25              30

Ser Ala Ala Val Ser Arg Pro Gly Arg Gly Glu Pro Arg Phe Ile Ala
            35              40              45

Met Gly Tyr Val Asp Asp Thr Gln Phe Val Arg Phe Asp Ser Asp Ser
    50              55              60

Ala Cys Pro Arg Met Glu Pro Arg Ala Pro Trp Val Glu Gln Glu Gly
65              70              75              80

Pro Glu Tyr Trp Glu Glu Glu Thr Arg Asn Thr Lys Ala His Ala Gln
                85              90              95

Thr Asp Arg Met Asn Leu Gln Thr Leu Arg Gly Tyr Tyr Asn Gln Ser
            100             105             110

Glu Ala Ser Ser His Thr Leu Gln Trp Met Ile Gly Cys Asp Leu Gly
            115             120             125

Ser Asp Gly Arg Leu Leu Arg Gly Tyr Glu Gln Tyr Ala Tyr Asp Gly
    130             135             140
```

-continued

```
Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Asp Pro
                195                 200                 205

Pro Lys Thr His Val Thr His His Pro Val Phe Asp Tyr Glu Ala Thr
        210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
        290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp
```

```
<210> SEQ ID NO 13
<211> LENGTH: 246
<212> TYPE: PRT
<213> ORGANISM: Homo sapiens

<400> SEQUENCE: 13
```

```
Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
                35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110

Glu Ala Lys Pro Pro Lys Thr His Val Thr His His Pro Val Phe Asp
                115                 120                 125

Tyr Glu Ala Thr Leu Arg Cys Trp Ala Leu Gly Phe Tyr Pro Ala Glu
        130                 135                 140

Ile Ile Leu Thr Trp Gln Arg Asp Gly Glu Asp Gln Thr Gln Asp Val
145                 150                 155                 160

Glu Leu Val Glu Thr Arg Pro Ala Gly Asp Gly Thr Phe Gln Lys Trp
                165                 170                 175
```

```
Ala Ala Val Val Val Pro Ser Gly Glu Glu Gln Arg Tyr Thr Cys His
            180             185             190

Val Gln His Glu Gly Leu Pro Glu Pro Leu Met Leu Arg Trp Lys Gln
        195             200             205

Ser Ser Leu Pro Thr Ile Pro Ile Met Gly Ile Val Ala Gly Leu Val
    210             215             220

Val Leu Ala Ala Val Val Thr Gly Ala Ala Val Ala Ala Val Leu Trp
225             230             235             240

Arg Lys Lys Ser Ser Asp
                245
```

```
<210> SEQ ID NO 14
<211> LENGTH: 154
<212> TYPE: PRT
<213> ORGANISM: Homo sapiens

<400> SEQUENCE: 14
```

```
Met Val Val Met Ala Pro Arg Thr Leu Phe Leu Leu Leu Ser Gly Ala
1               5               10              15

Leu Thr Leu Thr Glu Thr Trp Ala Gly Ser His Ser Met Arg Tyr Phe
            20              25              30

Ser Ala Ala Val Ser Arg Pro Gly Arg Gly Glu Pro Arg Phe Ile Ala
        35              40              45

Met Gly Tyr Val Asp Asp Thr Gln Phe Val Arg Phe Asp Ser Asp Ser
    50              55              60

Ala Cys Pro Arg Met Glu Pro Arg Ala Pro Trp Val Glu Gln Glu Gly
65              70              75              80

Pro Glu Tyr Trp Glu Glu Glu Thr Arg Asn Thr Lys Ala His Ala Gln
            85              90              95

Thr Asp Arg Met Asn Leu Gln Thr Leu Arg Gly Tyr Tyr Asn Gln Ser
            100             105             110

Glu Ala Lys Gln Ser Ser Leu Pro Thr Ile Pro Ile Met Gly Ile Val
        115             120             125

Ala Gly Leu Val Val Leu Ala Ala Val Val Thr Gly Ala Ala Val Ala
    130             135             140

Ala Val Leu Trp Arg Lys Lys Ser Ser Asp
145             150
```

```
<210> SEQ ID NO 15
<211> LENGTH: 246
<212> TYPE: PRT
<213> ORGANISM: Homo sapiens

<400> SEQUENCE: 15
```

```
Met Val Val Met Ala Pro Arg Thr Leu Phe Leu Leu Leu Ser Gly Ala
1               5               10              15

Leu Thr Leu Thr Glu Thr Trp Ala Gly Ser His Ser Met Arg Tyr Phe
            20              25              30

Ser Ala Ala Val Ser Arg Pro Gly Arg Gly Glu Pro Arg Phe Ile Ala
        35              40              45

Met Gly Tyr Val Asp Asp Thr Gln Phe Val Arg Phe Asp Ser Asp Ser
    50              55              60

Ala Cys Pro Arg Met Glu Pro Arg Ala Pro Trp Val Glu Gln Glu Gly
65              70              75              80

Pro Glu Tyr Trp Glu Glu Glu Thr Arg Asn Thr Lys Ala His Ala Gln
            85              90              95
```

```
Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
            130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Lys Gln
            195                 200                 205

Ser Ser Leu Pro Thr Ile Pro Ile Met Gly Ile Val Ala Gly Leu Val
            210                 215                 220

Val Leu Ala Ala Val Val Thr Gly Ala Ala Val Ala Ala Val Leu Trp
225                 230                 235                 240

Arg Lys Lys Ser Ser Asp
                245

<210> SEQ ID NO 16
<211> LENGTH: 319
<212> TYPE: PRT
<213> ORGANISM: Homo sapiens

<400> SEQUENCE: 16

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
            50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
            130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
            210                 215                 220
```

-continued

```
Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Glu Pro Leu Met Leu Arg Trp Ser Lys Glu Gly Asp Gly
            290                 295                 300

Gly Ile Met Ser Val Arg Glu Ser Arg Ser Leu Ser Glu Asp Leu
305                 310                 315

<210> SEQ ID NO 17
<211> LENGTH: 227
<212> TYPE: PRT
<213> ORGANISM: Homo sapiens

<400> SEQUENCE: 17

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Lys Pro Pro Lys Thr His Val Thr His His Pro Val Phe Asp
        115                 120                 125

Tyr Glu Ala Thr Leu Arg Cys Trp Ala Leu Gly Phe Tyr Pro Ala Glu
        130                 135                 140

Ile Ile Leu Thr Trp Gln Arg Asp Gly Glu Asp Gln Thr Gln Asp Val
145                 150                 155                 160

Glu Leu Val Glu Thr Arg Pro Ala Gly Asp Gly Thr Phe Gln Lys Trp
                165                 170                 175

Ala Ala Val Val Val Pro Ser Gly Glu Glu Gln Arg Tyr Thr Cys His
            180                 185                 190

Val Gln His Glu Gly Leu Pro Glu Pro Leu Met Leu Arg Trp Ser Lys
        195                 200                 205

Glu Gly Asp Gly Gly Ile Met Ser Val Arg Glu Ser Arg Ser Leu Ser
        210                 215                 220

Glu Asp Leu
225

<210> SEQ ID NO 18
<211> LENGTH: 116
<212> TYPE: PRT
<213> ORGANISM: Homo sapiens

<400> SEQUENCE: 18
```

```
Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Glu
        115
```

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Tyr Asp Met Ser
1               5
```

```
<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ile Ser Gly Gly Gly Ser Gln Thr Tyr Tyr Ala Glu Ser Val Lys
1               5                   10                  15

Gly
```

```
<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Ser Gly His Tyr Phe Tyr Ala Met Asp Val
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

```
Arg Ala Ser Gln Gly Ile Ser Asn Trp Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Ser Leu Gln Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Ala Glu Ser Phe Pro His Thr
1               5

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Gly Gly Gly Ser Gln Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Ser Pro Ser Gly His Tyr Phe Tyr Ala Met Asp Val Trp Gly Gln
            100                 105                 110

Gly Thr Thr Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Val Ser Ala Ser Val Gly
```

-continued

```
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
            35                  40                  45

Phe Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Glu Ser Phe Pro His
                85                  90                  95

Thr Phe Gly Gly Gly Thr Lys Val Glu Ile Lys
            100                 105
```

```
<210> SEQ ID NO 27
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
            35                  40                  45

Phe Thr Phe Ser Ser Tyr Asp Met Ser Trp Val Arg Gln Ala Pro Gly
        50                  55                  60

Lys Gly Leu Glu Trp Val Ser Leu Ile Ser Gly Gly Gly Ser Gln Thr
65                  70                  75                  80

Tyr Tyr Ala Glu Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Ser Pro Ser Gly His Tyr Phe Tyr Ala
            115                 120                 125

Met Asp Val Trp Gly Gln Gly Thr Thr Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
            210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255
```

```
Pro Glu Leu Leu Gly Gly Pro Ser Val Phe Leu Phe Pro Pro Lys Pro
            260             265             270

Lys Asp Thr Leu Met Ile Ser Arg Thr Pro Glu Val Thr Cys Val Val
        275             280             285

Val Asp Val Ser His Glu Asp Pro Glu Val Lys Phe Asn Trp Tyr Val
    290             295             300

Asp Gly Val Glu Val His Asn Ala Lys Thr Lys Pro Cys Glu Glu Gln
305             310             315             320

Tyr Gly Ser Thr Tyr Arg Cys Val Ser Val Leu Thr Val Leu His Gln
            325             330             335

Asp Trp Leu Asn Gly Lys Glu Tyr Lys Cys Lys Val Ser Asn Lys Ala
        340             345             350

Leu Pro Ala Pro Ile Glu Lys Thr Ile Ser Lys Ala Lys Gly Gln Pro
        355             360             365

Arg Glu Pro Gln Val Tyr Thr Leu Pro Pro Ser Arg Glu Glu Met Thr
    370             375             380

Lys Asn Gln Val Ser Leu Thr Cys Leu Val Lys Gly Phe Tyr Pro Ser
385             390             395             400

Asp Ile Ala Val Glu Trp Glu Ser Asn Gly Gln Pro Glu Asn Asn Tyr
            405             410             415

Lys Thr Thr Pro Pro Val Leu Asp Ser Asp Gly Ser Phe Phe Leu Tyr
            420             425             430

Ser Lys Leu Thr Val Asp Lys Ser Arg Trp Gln Gln Gly Asn Val Phe
        435             440             445

Ser Cys Ser Val Met His Glu Ala Leu His Asn His Tyr Thr Gln Lys
    450             455             460

Ser Leu Ser Leu Ser Pro Gly Lys
465             470

<210> SEQ ID NO 28
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Met Arg Val Pro Ala Gln Leu Leu Gly Leu Leu Leu Leu Trp
1               5               10              15

Leu Arg Gly Ala Arg Cys Asp Ile Gln Met Thr Gln Ser Pro Ser Ser
            20              25              30

Val Ser Ala Ser Val Gly Asp Arg Val Thr Ile Thr Cys Arg Ala Ser
        35              40              45

Gln Gly Ile Ser Asn Trp Leu Ala Trp Tyr Gln Gln Lys Pro Gly Lys
    50              55              60

Ala Pro Lys Leu Leu Ile Phe Ala Ala Ser Ser Leu Gln Ser Gly Val
65              70              75              80

Pro Ser Arg Phe Ser Gly Ser Gly Ser Gly Thr Asp Phe Thr Leu Thr
            85              90              95

Ile Ser Ser Leu Gln Pro Glu Asp Phe Ala Thr Tyr Tyr Cys Gln Gln
            100             105             110

Ala Glu Ser Phe Pro His Thr Phe Gly Gly Gly Thr Lys Val Glu Ile
        115             120             125

Lys Arg Thr Val Ala Ala Pro Ser Val Phe Ile Phe Pro Pro Ser Asp
    130             135             140
```

-continued

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 29
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Gly
        35                  40                  45

Val His Thr Phe Pro Ala Val Leu Gln Ser Ser Gly Leu Tyr Ser Leu
        50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
```

-continued

```
                260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
ggcugaacaa aggagatt                                                   18

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aacccacctg acttggatca                                                 20

<210> SEQ ID NO 33
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 33
tgaggtatat gcaatcgtca aaa                                                 23

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctggaactgg tggtgacaga                                                     20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctcctctag gtggtcagcc                                                     20

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Tyr Asp Met His
1               5

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ile Asp Thr Ala Gly Asp Thr Tyr Tyr Pro Asp Ser Val Arg Gly
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Val Pro Gly Thr Gly Phe Asp His
1               5

<210> SEQ ID NO 39
```

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gly Asp Ser Leu Arg Ser Tyr Tyr Glu Ser
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Lys Asn Asn Arg Pro Ser
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Ser Arg Asp Asn Ser Gly Asp His Trp Val
1               5                   10

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Asp Met His Trp Val Arg Gln Ala Thr Gly Lys Gly Leu Glu Trp Val
            35                  40                  45

Ala Thr Ile Asp Thr Ala Gly Asp Thr Tyr Tyr Pro Asp Ser Val Arg
        50                  55                  60

Gly Arg Phe Thr Ile Ser Arg Glu Asn Ala Lys Asn Ser Leu Ser Leu
65                  70                  75                  80

Gln Met Asn Ser Leu Arg Ala Gly Asp Thr Ala Val Tyr Phe Cys Ala
                85                  90                  95

Arg Asp Val Pro Gly Thr Gly Phe Asp His Trp Gly Gln Gly Thr Leu
            100                 105                 110

Val Thr Val Ser Ser
        115

<210> SEQ ID NO 43
<211> LENGTH: 108
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Glu
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ile Ser Gly Asn Thr Ala Ser Leu Thr Ile Thr Gly Thr Gln Ala Glu
65                  70                  75                  80

Asp Glu Ala Asp Tyr Tyr Cys Asn Ser Arg Asp Asn Ser Gly Asp His
            85                  90                  95

Trp Val Phe Gly Gly Gly Thr Arg Leu Thr Val Leu
            100                 105

<210> SEQ ID NO 44
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asp Tyr Asp Met His Trp Val Arg Gln Ala Thr Gly
    50                  55                  60

Lys Gly Leu Glu Trp Val Ala Thr Ile Asp Thr Ala Gly Asp Thr Tyr
65                  70                  75                  80

Tyr Pro Asp Ser Val Arg Gly Arg Phe Thr Ile Ser Arg Glu Asn Ala
            85                  90                  95

Lys Asn Ser Leu Ser Leu Gln Met Asn Ser Leu Arg Ala Gly Asp Thr
            100                 105                 110

Ala Val Tyr Phe Cys Ala Arg Asp Val Pro Gly Thr Gly Phe Asp His
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
```

```
                210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
            450                 455                 460

Gly Lys
465

<210> SEQ ID NO 45
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Met Arg Val Pro Ala Gln Leu Leu Gly Leu Leu Leu Leu Trp
1               5                   10                  15

Leu Arg Gly Ala Arg Cys Ser Ser Glu Leu Thr Gln Asp Pro Ala Val
                20                  25                  30

Ser Val Ala Leu Gly Gln Thr Val Arg Ile Thr Cys Gln Gly Asp Ser
            35                  40                  45

Leu Arg Ser Tyr Tyr Glu Ser Trp Tyr Gln Gln Lys Pro Gly Gln Ala
        50                  55                  60

Pro Val Leu Val Ile Tyr Gly Lys Asn Asn Arg Pro Ser Gly Ile Pro
65                  70                  75                  80

Asp Arg Phe Ser Gly Ser Ile Ser Gly Asn Thr Ala Ser Leu Thr Ile
                85                  90                  95
```

```
Thr Gly Thr Gln Ala Glu Asp Glu Ala Asp Tyr Tyr Cys Asn Ser Arg
            100                 105                 110

Asp Asn Ser Gly Asp His Trp Val Phe Gly Gly Gly Thr Arg Leu Thr
            115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 46
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 47
<211> LENGTH: 106
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 47

```
Gly Gln Pro Lys Ala Ala Pro Ser Val Thr Leu Phe Pro Pro Ser Ser
1                 5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 48

```
Ser Tyr Ala Met His
1               5
```

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 49

```
Ile Ile Trp Phe Asp Gly Ser Gln Arg Tyr Tyr Ala Asp Ser Val Lys
1               5                   10                  15

Gly

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Glu Leu Thr Gly Phe Asp Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Asn Ile Ile Asn Phe Leu Asn
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ala Ser Ser Leu Arg Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Ser Phe Ser Thr Pro Leu Thr
1               5

<210> SEQ ID NO 54
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
```

-continued

```
        35                    40                    45
Ala Ile Ile Trp Phe Asp Gly Ser Gln Arg Tyr Tyr Ala Asp Ser Val
    50                    55                    60

Lys Gly Arg Phe Thr Ile Ser Arg Asp Asn Ser Arg Asp Thr Leu Tyr
65                    70                    75                    80

Leu Gln Met Asn Ser Leu Arg Ala Glu Asp Thr Ala Val Tyr Tyr Cys
                85                    90                    95

Ala Arg Asp Glu Leu Thr Gly Phe Asp Tyr Trp Gly Gln Gly Thr Leu
            100                    105                    110

Val Thr Val Ser Ser
            115

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1                    5                    10                    15

Asp Arg Val Thr Ile Ser Cys Arg Ala Ser Gln Asn Ile Ile Asn Phe
                20                    25                    30

Leu Asn Trp Tyr Gln Gln Lys Pro Gly Lys Ala Pro Lys Val Leu Ile
        35                    40                    45

Asp Ala Ala Ser Ser Leu Arg Ser Gly Val Pro Ser Arg Phe Ser Gly
    50                    55                    60

Ser Gly Ser Glu Thr Asp Phe Ser Leu Thr Ile Ser Ser Leu Gln Pro
65                    70                    75                    80

Glu Asp Phe Ala Thr Tyr Tyr Cys Gln Gln Ser Phe Ser Thr Pro Leu
                85                    90                    95

Thr Phe Gly Gly Gly Thr Lys Val Glu Ile Arg
            100                    105

<210> SEQ ID NO 56
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Asp Met Arg Val Pro Ala Gln Leu Leu Gly Leu Leu Leu Leu Trp
1                    5                    10                    15

Leu Arg Gly Ala Arg Cys Gln Val Gln Leu Val Glu Ser Gly Gly Gly
                20                    25                    30

Val Val Gln Pro Gly Arg Ser Leu Arg Leu Ser Cys Ala Ala Ser Gly
            35                    40                    45

Phe Thr Phe Ser Ser Tyr Ala Met His Trp Val Arg Gln Ala Pro Gly
        50                    55                    60

Lys Gly Leu Glu Trp Val Ala Ile Ile Trp Phe Asp Gly Ser Gln Arg
65                    70                    75                    80

Tyr Tyr Ala Asp Ser Val Lys Gly Arg Phe Thr Ile Ser Arg Asp Asn
                85                    90                    95

Ser Arg Asp Thr Leu Tyr Leu Gln Met Asn Ser Leu Arg Ala Glu Asp
```

-continued

```
                100                 105                 110
Thr Ala Val Tyr Tyr Cys Ala Arg Asp Glu Leu Thr Gly Phe Asp Tyr
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
    275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
    450                 455                 460

Gly Lys
465
```

<210> SEQ ID NO 57
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 57

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Ser Cys Arg Ala Ser
        35                  40                  45

Gln Asn Ile Ile Asn Phe Leu Asn Trp Tyr Gln Gln Lys Pro Gly Lys
    50                  55                  60

Ala Pro Lys Val Leu Ile Asp Ala Ala Ser Ser Leu Arg Ser Gly Val
65                  70                  75                  80

Pro Ser Arg Phe Ser Gly Ser Gly Ser Glu Thr Asp Phe Ser Leu Thr
                85                  90                  95

Ile Ser Ser Leu Gln Pro Glu Asp Phe Ala Thr Tyr Tyr Cys Gln Gln
            100                 105                 110

Ser Phe Ser Thr Pro Leu Thr Phe Gly Gly Gly Thr Lys Val Glu Ile
        115                 120                 125

Arg Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Asp Tyr Asp Met His
1               5
```

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Ala Ile Asp Thr Ala Gly Asp Thr Tyr Tyr Leu Gly Pro Val Lys Gly
1               5                   10                  15
```

<210> SEQ ID NO 60
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ser Gly Ser Ser Phe Asp Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gly Asp Ser Leu Arg Asn Tyr Tyr Glu Ser
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Lys Asn Asn Arg Pro Ser
1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Ser Arg Asp Ser Ser Gly Asn His Trp Val
1               5                   10

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Ser Asp Tyr
            20                  25                  30

Asp Met His Trp Val Arg Gln Ala Thr Gly Lys Gly Leu Glu Trp Val
        35                  40                  45

Ser Ala Ile Asp Thr Ala Gly Asp Thr Tyr Tyr Leu Gly Pro Val Lys
    50                  55                  60

Gly Arg Phe Thr Ile Ser Arg Glu Asn Ala Lys Asn Ser Leu Phe Leu
65                  70                  75                  80
```

```
His Met Asn Ser Leu Arg Val Gly Asp Thr Ala Val Tyr Tyr Cys Ile
                85                  90                  95

Arg Asp Ser Gly Ser Ser Phe Asp Tyr Trp Gly Gln Gly Thr Leu Val
            100                 105                 110

Thr Val Ser Ser
        115

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Thr Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Glu
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Ile Ile Thr Gly Thr Gln Ala Glu
65                  70                  75                  80

Asp Glu Ala Asp Tyr Tyr Cys Met Ser Arg Asp Ser Ser Gly Asn His
                85                  90                  95

Trp Val Phe Gly Gly Gly Thr Lys Val Thr Val Leu
            100                 105

<210> SEQ ID NO 66
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Glu Ser Leu Arg Leu Ser Cys Ala Ala Ser Gly
        35                  40                  45

Phe Thr Phe Ser Asp Tyr Asp Met His Trp Val Arg Gln Ala Thr Gly
    50                  55                  60

Lys Gly Leu Glu Trp Val Ser Ala Ile Asp Thr Ala Gly Asp Thr Tyr
65                  70                  75                  80

Tyr Leu Gly Pro Val Lys Gly Arg Phe Thr Ile Ser Arg Glu Asn Ala
                85                  90                  95

Lys Asn Ser Leu Phe Leu His Met Asn Ser Leu Arg Val Gly Asp Thr
            100                 105                 110

Ala Val Tyr Tyr Cys Ile Arg Asp Ser Gly Ser Ser Phe Asp Tyr Trp
        115                 120                 125

Gly Gln Gly Thr Leu Val Thr Val Ser Ser Ala Ser Thr Lys Gly Pro
    130                 135                 140
```

-continued

```
Ser Val Phe Pro Leu Ala Pro Cys Ser Arg Ser Thr Ser Glu Ser Thr
145             150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
                420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
    450                 455                 460

Lys
465
```

```
<210> SEQ ID NO 67
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Met Arg Val Pro Ala Gln Leu Leu Gly Leu Leu Leu Leu Trp
1               5                   10                  15

Leu Arg Gly Ala Arg Cys Thr Ser Glu Leu Thr Gln Asp Pro Ala Val
                20                  25                  30
```

```
Ser Val Ala Leu Gly Gln Thr Val Arg Ile Thr Cys Gln Gly Asp Ser
        35                  40                  45

Leu Arg Asn Tyr Tyr Glu Ser Trp Tyr Gln Gln Lys Pro Gly Gln Ala
    50                  55                  60

Pro Val Leu Val Ile Tyr Gly Lys Asn Asn Arg Pro Ser Gly Ile Pro
65                  70                  75                  80

Asp Arg Phe Ser Gly Ser Ser Ser Gly Asn Thr Ala Ser Leu Ile Ile
                85                  90                  95

Thr Gly Thr Gln Ala Glu Asp Glu Ala Asp Tyr Tyr Cys Met Ser Arg
                100                 105                 110

Asp Ser Ser Gly Asn His Trp Val Phe Gly Gly Gly Thr Lys Val Thr
                115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
                180                 185                 190

Asn Asn Lys Tyr Ala Ala Ser Ser Tyr Leu Ser Leu Thr Pro Glu Gln
                195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

```
<210> SEQ ID NO 68
<211> LENGTH: 330
<212> TYPE: PRT
<213> ORGANISM: Homo sapiens

<400> SEQUENCE: 68
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                   165              170              175
Glu Gln Tyr Asn Ser Thr Tyr Arg Val Val Ser Val Leu Thr Val Leu
            180              185              190
His Gln Asp Trp Leu Asn Gly Lys Glu Tyr Lys Cys Lys Val Ser Asn
            195              200              205
Lys Ala Leu Pro Ala Pro Ile Glu Lys Thr Ile Ser Lys Ala Lys Gly
        210              215              220
Gln Pro Arg Glu Pro Gln Val Tyr Thr Leu Pro Pro Ser Arg Asp Glu
225              230              235              240
Leu Thr Lys Asn Gln Val Ser Leu Thr Cys Leu Val Lys Gly Phe Tyr
                245              250              255
Pro Ser Asp Ile Ala Val Glu Trp Glu Ser Asn Gly Gln Pro Glu Asn
            260              265              270
Asn Tyr Lys Thr Thr Pro Pro Val Leu Asp Ser Asp Gly Ser Phe Phe
            275              280              285
Leu Tyr Ser Lys Leu Thr Val Asp Lys Ser Arg Trp Gln Gln Gly Asn
        290              295              300
Val Phe Ser Cys Ser Val Met His Glu Ala Leu His Asn His Tyr Thr
305              310              315              320
Gln Lys Ser Leu Ser Leu Ser Pro Gly Lys
                325              330
```

<210> SEQ ID NO 69
<211> LENGTH: 326
<212> TYPE: PRT
<213> ORGANISM: Homo sapiens

<400> SEQUENCE: 69

```
Ala Ser Thr Lys Gly Pro Ser Val Phe Pro Leu Ala Pro Cys Ser Arg
1               5               10              15
Ser Thr Ser Glu Ser Thr Ala Ala Leu Gly Cys Leu Val Lys Asp Tyr
            20              25              30
Phe Pro Glu Pro Val Thr Val Ser Trp Asn Ser Gly Ala Leu Thr Ser
        35              40              45
Gly Val His Thr Phe Pro Ala Val Leu Gln Ser Ser Gly Leu Tyr Ser
    50              55              60
Leu Ser Ser Val Val Thr Val Pro Ser Ser Asn Phe Gly Thr Gln Thr
65              70              75              80
Tyr Thr Cys Asn Val Asp His Lys Pro Ser Asn Thr Lys Val Asp Lys
                85              90              95
Thr Val Glu Arg Lys Cys Cys Val Glu Cys Pro Pro Cys Pro Ala Pro
            100             105             110
Pro Val Ala Gly Pro Ser Val Phe Leu Phe Pro Pro Lys Pro Lys Asp
            115             120             125
Thr Leu Met Ile Ser Arg Thr Pro Glu Val Thr Cys Val Val Val Asp
        130             135             140
Val Ser His Glu Asp Pro Glu Val Gln Phe Asn Trp Tyr Val Asp Gly
145             150             155             160
Val Glu Val His Asn Ala Lys Thr Lys Pro Arg Glu Glu Gln Phe Asn
                165             170             175
Ser Thr Phe Arg Val Val Ser Val Leu Thr Val Val His Gln Asp Trp
            180             185             190
Leu Asn Gly Lys Glu Tyr Lys Cys Lys Val Ser Asn Lys Gly Leu Pro
            195             200             205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 70
<211> LENGTH: 377
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

-continued

```
Ala Leu Pro Ala Pro Ile Glu Lys Thr Ile Ser Lys Thr Lys Gly Gln
            260             265             270

Pro Arg Glu Pro Gln Val Tyr Thr Leu Pro Pro Ser Arg Glu Glu Met
            275             280             285

Thr Lys Asn Gln Val Ser Leu Thr Cys Leu Val Lys Gly Phe Tyr Pro
    290             295             300

Ser Asp Ile Ala Val Glu Trp Glu Ser Ser Gly Gln Pro Glu Asn Asn
305             310             315             320

Tyr Asn Thr Thr Pro Pro Met Leu Asp Ser Asp Gly Ser Phe Phe Leu
            325             330             335

Tyr Ser Lys Leu Thr Val Asp Lys Ser Arg Trp Gln Gln Gly Asn Ile
            340             345             350

Phe Ser Cys Ser Val Met His Glu Ala Leu His Asn Arg Phe Thr Gln
            355             360             365

Lys Ser Leu Ser Leu Ser Pro Gly Lys
    370             375
```